US008932217B2

(12) United States Patent
Gibson et al.

(10) Patent No.: US 8,932,217 B2
(45) Date of Patent: Jan. 13, 2015

(54) VITAL SIGNS MONITOR

(75) Inventors: Grant S. Gibson, Portland, OR (US);
Cory R. Gondek, Tigard, OR (US);
Richard A. Sunderland, Aloha, OR
(US); Steven D. Baker, Beaverton, OR
(US); Robert T. Lewis, Beaverton, OR
(US); Braxton L. Lathrop, Lake
Oswego, OR (US); **Christopher L.
Dunn, Lake Oswego, OR (US); Omer
Kotzer**, Portland, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1700 days.

(21) Appl. No.: 11/795,301

(22) PCT Filed: Jan. 13, 2006

(86) PCT No.: PCT/US2006/001093
§ 371 (c)(1),
(2), (4) Date: Apr. 10, 2008

(87) PCT Pub. No.: WO2006/076498
PCT Pub. Date: Jul. 20, 2006

(65) Prior Publication Data
US 2008/0281168 A1 Nov. 13, 2008

Related U.S. Application Data

(60) Provisional application No. 60/643,636, filed on Jan. 13, 2005.

(51) Int. Cl.
*G06F 19/00* (2011.01)
*A61B 5/00* (2006.01)
*A61B 5/024* (2006.01)
*A61B 5/0205* (2006.01)
*A61B 5/0424* (2006.01)
*A61B 5/1455* (2006.01)

(52) U.S. Cl.
CPC ........ *A61B 5/02438* (2013.01); *G06F 19/3406* (2013.01); *A61B 5/7275* (2013.01); *A61B 5/746* (2013.01); *A61B 5/0205* (2013.01); *A61B 5/0424* (2013.01); *A61B 5/14551* (2013.01); *A61B 5/6843* (2013.01); *A61B 5/6887* (2013.01); *A61B 5/742* (2013.01); *A61B 5/7475* (2013.01); *A61B 5/002* (2013.01); *A61B 5/0022* (2013.01); *A61B 2560/0276* (2013.01); *A61B 2560/0456* (2013.01)
USPC .......................................... 600/301; 600/300

(58) Field of Classification Search
None
See application file for complete search history.

(56) References Cited

U.S. PATENT DOCUMENTS

| 3,996,928 A | 12/1976 | Marx |
| 4,026,278 A | 5/1977 | Ricketts et al. |
| 4,051,522 A | 9/1977 | Healy et al. |
| 4,090,505 A | 5/1978 | Mortara |
| 4,121,574 A | 10/1978 | Lester |
| 4,129,125 A | 12/1978 | Lester et al. |

(Continued)

FOREIGN PATENT DOCUMENTS

WO WO9625877 A1 * 8/1996 ........... A61B 5/0404

OTHER PUBLICATIONS

Extended European Search Report for EP Application No. 06 718 193.3; Mailed Jul. 29, 2009; 8 pages.

*Primary Examiner* — William Thomson
*Assistant Examiner* — Davin K Sands
(74) *Attorney, Agent, or Firm* — Hiscock & Barclay, LLP

(57) ABSTRACT

A multi-parametric vital signs monitoring device configured for use as an ambulatory and a bedside monitor wherein the device can be patient-wearable and is battery powered. The monitoring device can be used with a charging cradle to provide power to the device in lieu of the battery as a power source for bedside applications, in which the cradle further serves as an intermediary device to enable a data link with a PC or other peripheral device. The monitoring device can include a wireless radio to enable bi-directional transfer of patient-related data to a separate remote station.

18 Claims, 35 Drawing Sheets

(56) References Cited

U.S. PATENT DOCUMENTS

| | | |
|---|---|---|
| 4,270,547 A | 6/1981 | Steffen et al. |
| 4,276,888 A | 7/1981 | Smith et al. |
| 4,308,870 A | 1/1982 | Arkans |
| 4,347,851 A | 9/1982 | Jundanian |
| 4,383,534 A | 5/1983 | Peters |
| 4,411,267 A | 10/1983 | Heyman |
| 4,494,553 A | 1/1985 | Sciarra et al. |
| 4,522,213 A | 6/1985 | Wallroth et al. |
| 4,526,176 A | 7/1985 | Bremer et al. |
| 4,583,553 A | 4/1986 | Shah et al. |
| 4,705,048 A | 11/1987 | Pfohl |
| 4,712,562 A | 12/1987 | Ohayon et al. |
| 4,715,385 A | 12/1987 | Cudahy et al. |
| 4,724,844 A | 2/1988 | Rafelson |
| 4,803,625 A | 2/1989 | Fu et al. |
| 4,827,943 A | 5/1989 | Bornn et al. |
| 4,835,372 A | 5/1989 | Gombrich et al. |
| 4,852,571 A | 8/1989 | Gadsby |
| 4,860,759 A | 8/1989 | Kahn et al. |
| 4,889,131 A | 12/1989 | Salem et al. |
| 4,889,132 A | 12/1989 | Hutcheson et al. |
| 4,889,839 A | 12/1989 | Chu et al. |
| 4,895,161 A | 1/1990 | Cudahy et al. |
| 4,909,260 A | 3/1990 | Salem et al. |
| 4,916,441 A | 4/1990 | Gombrich |
| 4,951,678 A | 8/1990 | Joseph et al. |
| 4,958,636 A | 9/1990 | Blandino et al. |
| 4,958,638 A | 9/1990 | Sharpe et al. |
| 4,981,139 A | 1/1991 | Pfohl |
| 5,003,984 A | 4/1991 | Muraki et al. |
| 5,010,890 A | 4/1991 | Pfohl et al. |
| 5,022,404 A | 6/1991 | Hafner |
| 5,025,808 A | 6/1991 | Hafner |
| 5,036,869 A | 8/1991 | Inahara |
| 5,038,800 A | 8/1991 | Oba |
| 5,131,399 A | 7/1992 | Sciarra |
| D328,645 S | 8/1992 | Rogler et al. |
| 5,140,519 A | 8/1992 | Friesdorf et al. |
| 5,181,521 A | 1/1993 | Lemelson |
| 5,187,641 A | 2/1993 | Muskatello et al. |
| 5,188,108 A | 2/1993 | Secker et al. |
| 5,205,294 A | 4/1993 | Flach et al. |
| 5,215,087 A | 6/1993 | Anderson et al. |
| 5,285,783 A | 2/1994 | Secker et al. |
| 5,285,784 A | 2/1994 | Seeker |
| 5,285,792 A | 2/1994 | Sjoquist et al. |
| 5,309,908 A | 5/1994 | Friedman et al. |
| 5,319,363 A | 6/1994 | Welch et al. |
| 5,331,549 A | 7/1994 | Crawford, Jr. |
| 5,333,617 A | 8/1994 | Hafner |
| 5,339,810 A | 8/1994 | Ivers et al. |
| 5,343,869 A | 9/1994 | Pross et al. |
| 5,355,893 A | 10/1994 | Mick et al. |
| 5,361,755 A | 11/1994 | Schraag et al. |
| 5,375,604 A | 12/1994 | Kelly et al. |
| 5,396,224 A | 3/1995 | Dukes et al. |
| 5,410,471 A | 4/1995 | Alyfuku et al. |
| D357,982 S | 5/1995 | Dahl et al. |
| 5,413,099 A | 5/1995 | Schmidt et al. |
| 5,413,102 A | 5/1995 | Schmidt et al. |
| 5,417,222 A | 5/1995 | Dempsey et al. |
| 5,446,548 A | 8/1995 | Gerig et al. |
| 5,456,261 A | 10/1995 | Luczyk |
| 5,458,123 A | 10/1995 | Unger |
| 5,458,124 A | 10/1995 | Stanko et al. |
| 5,469,844 A | 11/1995 | Rogler |
| 5,473,536 A | 12/1995 | Wimmer |
| 5,494,051 A | 2/1996 | Schneider, Sr. |
| 5,513,406 A | 5/1996 | Foster et al. |
| 5,526,287 A | 6/1996 | French |
| 5,529,073 A | 6/1996 | Kielbasiewicz |
| 5,537,289 A | 7/1996 | Dahl |
| 5,544,661 A | 8/1996 | Davis et al. |
| 5,553,113 A | 9/1996 | Weedon |
| 5,558,638 A | 9/1996 | Evers et al. |
| 5,566,676 A | 10/1996 | Rosenfeldt et al. |
| 5,573,012 A | 11/1996 | McEwan et al. |
| 5,579,001 A | 11/1996 | Dempsey et al. |
| 5,579,775 A * | 12/1996 | Dempsey et al. ............ 600/483 |
| 5,594,786 A | 1/1997 | Chaco et al. |
| 5,600,108 A | 2/1997 | Newham |
| 5,614,887 A | 3/1997 | Buchbinder |
| 5,633,910 A | 5/1997 | Cohen |
| 5,640,953 A | 6/1997 | Bishop et al. |
| 5,649,535 A | 7/1997 | Voith |
| 5,650,770 A | 7/1997 | Schlager et al. |
| 5,662,105 A | 9/1997 | Tien |
| 5,664,270 A | 9/1997 | Bell et al. |
| 5,666,958 A | 9/1997 | Rothenberg et al. |
| 5,685,314 A | 11/1997 | Geheb et al. |
| 5,687,717 A | 11/1997 | Halpern et al. |
| 5,687,734 A | 11/1997 | Dempsey et al. |
| 5,689,229 A | 11/1997 | Chaco et al. |
| 5,689,242 A | 11/1997 | Sims et al. |
| 5,704,364 A | 1/1998 | Saltzstein et al. |
| 5,713,350 A | 2/1998 | Yokota et al. |
| 5,715,451 A | 2/1998 | Marlin |
| D393,072 S | 3/1998 | Rogler |
| 5,724,025 A | 3/1998 | Tavori |
| 5,732,074 A | 3/1998 | Spaur et al. |
| 5,740,001 A | 4/1998 | Flachslaender et al. |
| 5,746,697 A * | 5/1998 | Swedlow et al. ............ 600/323 |
| 5,748,103 A | 5/1998 | Flach et al. |
| 5,749,374 A | 5/1998 | Schneider, Sr. |
| 5,749,907 A | 5/1998 | Mann |
| 5,752,917 A | 5/1998 | Fuchs |
| 5,766,208 A | 6/1998 | McEwan |
| 5,767,791 A | 6/1998 | Stoop et al. |
| 5,785,650 A | 7/1998 | Akasaka et al. |
| 5,788,644 A * | 8/1998 | Donehoo et al. ............ 600/509 |
| 5,801,755 A | 9/1998 | Echerer |
| 5,819,741 A | 10/1998 | Karlsson et al. |
| 5,822,544 A | 10/1998 | Chaco et al. |
| 5,827,180 A | 10/1998 | Goodman |
| 5,832,448 A | 11/1998 | Brown |
| 5,840,036 A | 11/1998 | Voith |
| 5,855,550 A | 1/1999 | Lai et al. |
| 5,860,176 A | 1/1999 | Norberg |
| 5,865,733 A | 2/1999 | Malinouskas |
| 5,867,688 A | 2/1999 | Simmon et al. |
| 5,882,300 A | 3/1999 | Malinouskas et al. |
| 5,902,234 A | 5/1999 | Webb |
| 5,907,291 A | 5/1999 | Chen et al. |
| 5,919,141 A | 7/1999 | Money et al. |
| 5,924,074 A | 7/1999 | Evans |
| 5,924,979 A | 7/1999 | Swedlow et al. |
| 5,931,791 A | 8/1999 | Saltzstein et al. |
| 5,936,539 A | 8/1999 | Fuchs |
| 5,944,659 A | 8/1999 | Flach et al. |
| 5,947,907 A | 9/1999 | Duich |
| 5,959,611 A | 9/1999 | Smailagic et al. |
| 5,961,446 A | 10/1999 | Beller et al. |
| 5,967,993 A | 10/1999 | Maruyama et al. |
| 6,004,312 A | 12/1999 | Finneran et al. |
| 6,005,658 A * | 12/1999 | Kaluza et al. ............ 356/39 |
| 6,011,989 A | 1/2000 | Sugo et al. |
| 6,016,445 A | 1/2000 | Baura |
| 6,021,351 A | 2/2000 | Kadhiresan et al. |
| 6,049,731 A | 4/2000 | Ochiai et al. |
| 6,057,758 A | 5/2000 | Dempsey et al. |
| 6,062,902 A | 5/2000 | Buckles et al. |
| 6,067,462 A | 5/2000 | Diab et al. |
| 6,077,082 A | 6/2000 | Gibson et al. |
| 6,083,156 A | 7/2000 | Lisiecki |
| 6,083,171 A | 7/2000 | Ono et al. |
| 6,093,146 A | 7/2000 | Filangeri |
| 6,102,856 A | 8/2000 | Groff et al. |
| 6,104,941 A | 8/2000 | Huey et al. |
| 6,106,457 A | 8/2000 | Perkins et al. |
| 6,122,543 A | 9/2000 | Ochiai et al. |
| 6,150,951 A | 11/2000 | Olejniczak |
| 6,157,855 A | 12/2000 | Sjöholm |
| 6,157,935 A | 12/2000 | Tran et al. |
| 6,160,478 A | 12/2000 | Jacobsen et al. |

(56) References Cited

U.S. PATENT DOCUMENTS

| | | | |
|---|---|---|---|
| 6,161,036 A | 12/2000 | Matsumura et al. | |
| 6,167,258 A | 12/2000 | Schmidt et al. | |
| 6,171,237 B1 | 1/2001 | Avitall et al. | |
| 6,176,826 B1 | 1/2001 | Shimura et al. | |
| 6,183,417 B1 | 2/2001 | Geheb et al. | |
| 6,185,454 B1 | 2/2001 | Thompson | |
| 6,185,460 B1 | 2/2001 | Thompson | |
| 6,188,407 B1 | 2/2001 | Smith et al. | |
| 6,198,390 B1 | 3/2001 | Schlager et al. | |
| 6,198,394 B1 | 3/2001 | Jacobsen et al. | |
| 6,206,829 B1 | 3/2001 | Iliff | |
| 6,210,301 B1 | 4/2001 | Abraham-Fuchs et al. | |
| 6,213,942 B1 | 4/2001 | Flach et al. | |
| 6,221,012 B1 * | 4/2001 | Maschke et al. | 600/301 |
| 6,223,080 B1 | 4/2001 | Thompson | |
| 6,224,549 B1 | 5/2001 | Drongelen | |
| 6,234,964 B1 | 5/2001 | Iliff | |
| 6,241,682 B1 | 6/2001 | Ochiai et al. | |
| 6,246,992 B1 | 6/2001 | Brown | |
| 6,247,674 B1 | 6/2001 | Jawidzik | |
| 6,248,064 B1 | 6/2001 | Gopinathan et al. | |
| 6,252,531 B1 | 6/2001 | Gordon et al. | |
| 6,259,355 B1 | 7/2001 | Chaco et al. | |
| 6,259,944 B1 | 7/2001 | Margulis et al. | |
| 6,263,222 B1 | 7/2001 | Diab et al. | |
| 6,263,235 B1 | 7/2001 | Kaiser et al. | |
| 6,267,722 B1 | 7/2001 | Anderson et al. | |
| 6,267,723 B1 | 7/2001 | Matsumura et al. | |
| 6,282,440 B1 | 8/2001 | Brodnick et al. | |
| 6,287,252 B1 | 9/2001 | Lugo | |
| 6,309,342 B1 | 10/2001 | Blazey et al. | |
| 6,319,200 B1 | 11/2001 | Lai et al. | |
| 6,322,502 B1 | 11/2001 | Schoenberg et al. | |
| 6,336,900 B1 | 1/2002 | Alleckson et al. | |
| 6,339,715 B1 | 1/2002 | Bahr et al. | |
| 6,352,504 B1 | 3/2002 | Ise et al. | |
| 6,353,445 B1 | 3/2002 | Babula et al. | |
| 6,364,834 B1 | 4/2002 | Reuss et al. | |
| 6,370,423 B1 | 4/2002 | Guerrero et al. | |
| 6,375,614 B1 | 4/2002 | Braun et al. | |
| 6,377,223 B1 | 4/2002 | Clapp et al. | |
| 6,389,308 B1 | 5/2002 | Shusterman | |
| 6,394,952 B1 | 5/2002 | Anderson et al. | |
| 6,398,727 B1 | 6/2002 | Bui et al. | |
| 6,401,138 B1 | 6/2002 | Judge et al. | |
| 6,402,691 B1 | 6/2002 | Peddicord et al. | |
| 6,405,076 B1 | 6/2002 | Taylor et al. | |
| 6,405,083 B1 | 6/2002 | Rockwell et al. | |
| 6,406,426 B1 | 6/2002 | Reuss et al. | |
| 6,407,335 B1 | 6/2002 | Franklin-Lees et al. | |
| 6,409,659 B1 | 6/2002 | Warner et al. | |
| 6,409,662 B1 | 6/2002 | Lloyd et al. | |
| 6,412,980 B1 | 7/2002 | Lounsberry et al. | |
| 6,416,471 B1 | 7/2002 | Kumar et al. | |
| 6,418,346 B1 | 7/2002 | Nelson et al. | |
| 6,434,572 B2 | 8/2002 | Derzay et al. | |
| RE37,852 E | 9/2002 | Aso et al. | |
| 6,454,708 B1 | 9/2002 | Ferguson et al. | |
| 6,454,718 B1 | 9/2002 | Clift | |
| 6,471,087 B1 | 10/2002 | Shusterman | |
| 6,491,647 B1 | 12/2002 | Bridger et al. | |
| 6,493,220 B1 | 12/2002 | Clark et al. | |
| 6,493,568 B1 | 12/2002 | Bell et al. | |
| 6,505,067 B1 | 1/2003 | Lee et al. | |
| 6,516,073 B1 | 2/2003 | Schulz et al. | |
| 6,520,073 B1 | 2/2003 | Sorensen | |
| 6,524,240 B1 | 2/2003 | Thede | |
| 6,537,214 B1 | 3/2003 | Hood et al. | |
| 6,537,225 B1 | 3/2003 | Mills | |
| 6,539,249 B1 | 3/2003 | Kadhiresan et al. | |
| 6,540,673 B2 | 4/2003 | Gopinathan | |
| 6,544,173 B2 | 4/2003 | West et al. | |
| 6,544,174 B2 | 4/2003 | West et al. | |
| 6,547,740 B2 | 4/2003 | Sugo et al. | |
| 6,551,243 B2 | 4/2003 | Bocionek et al. | |
| 6,551,252 B2 | 4/2003 | Sackner et al. | |
| 6,556,630 B1 | 4/2003 | Brinsfield et al. | |
| 6,558,321 B1 | 5/2003 | Burd et al. | |
| 6,572,545 B2 | 6/2003 | Knobbe et al. | |
| 6,575,905 B2 | 6/2003 | Knobbe et al. | |
| 6,577,901 B2 | 6/2003 | Thompson | |
| 6,579,231 B1 | 6/2003 | Phipps | |
| 6,579,232 B2 | 6/2003 | Sakamaki et al. | |
| 6,579,242 B2 | 6/2003 | Bui et al. | |
| 6,584,336 B1 | 6/2003 | Ali et al. | |
| 6,585,645 B2 | 7/2003 | Hutchinson | |
| 6,589,170 B1 | 7/2003 | Flach et al. | |
| 6,591,135 B2 | 7/2003 | Palmer et al. | |
| 6,593,528 B2 | 7/2003 | Franklin-Lees et al. | |
| 6,594,146 B2 | 7/2003 | Frangesch et al. | |
| 6,595,918 B2 | 7/2003 | Gopinathan et al. | |
| 6,595,929 B2 | 7/2003 | Stivoric et al. | |
| 6,600,421 B2 | 7/2003 | Freeman | |
| 6,602,191 B2 | 8/2003 | Quy | |
| 6,610,010 B2 | 8/2003 | Sjöqvist | |
| 6,611,705 B2 | 8/2003 | Hopman et al. | |
| 6,616,598 B2 | 9/2003 | Kaushansky et al. | |
| 6,616,606 B1 | 9/2003 | Petersen et al. | |
| 6,616,613 B1 | 9/2003 | Goodman | |
| 6,629,937 B2 | 10/2003 | Watrous | |
| 6,631,281 B1 | 10/2003 | Kästle | |
| 6,638,218 B2 | 10/2003 | Bulat | |
| 6,640,145 B2 | 10/2003 | Hoffberg et al. | |
| 6,641,533 B2 * | 11/2003 | Causey et al. | 600/300 |
| 6,647,280 B2 | 11/2003 | Bahr et al. | |
| 6,647,287 B1 | 11/2003 | Peel, III et al. | |
| 6,648,820 B1 | 11/2003 | Screl | |
| 6,656,125 B2 | 12/2003 | Misczynski et al. | |
| 6,657,976 B1 | 12/2003 | Larghi | |
| 6,661,379 B2 | 12/2003 | Stilp et al. | |
| 6,669,630 B1 | 12/2003 | Joliat et al. | |
| 6,671,563 B1 | 12/2003 | Engelson et al. | |
| 6,676,600 B1 | 1/2004 | Conero et al. | |
| 6,705,990 B1 | 3/2004 | Gallant et al. | |
| 6,716,165 B1 | 4/2004 | Flanders et al. | |
| 6,721,178 B1 | 4/2004 | Clark et al. | |
| 6,723,045 B2 | 4/2004 | Cosentino et al. | |
| 6,726,634 B2 | 4/2004 | Freeman | |
| 6,731,989 B2 | 5/2004 | Engleson et al. | |
| 6,733,447 B2 | 5/2004 | Lai et al. | |
| 6,733,464 B2 | 5/2004 | Olbrich et al. | |
| 6,738,798 B1 | 5/2004 | Ploetz et al. | |
| 6,740,033 B1 | 5/2004 | Olejniczak et al. | |
| 6,741,887 B1 | 5/2004 | Gleeson | |
| 6,745,036 B1 | 6/2004 | Dunne et al. | |
| 6,746,403 B2 | 6/2004 | Kolluri et al. | |
| 6,749,566 B2 | 6/2004 | Russ | |
| 6,751,650 B1 | 6/2004 | Finch, II et al. | |
| 6,755,795 B2 | 6/2004 | Marmaropoulos et al. | |
| 6,763,260 B2 | 7/2004 | Kohls | |
| 6,770,028 B1 * | 8/2004 | Ali et al. | 600/300 |
| 6,773,396 B2 | 8/2004 | Flach et al. | |
| 6,783,501 B2 | 8/2004 | Takahashi et al. | |
| 6,790,178 B1 | 9/2004 | Mault et al. | |
| 6,792,396 B2 | 9/2004 | Inda et al. | |
| 6,795,688 B1 | 9/2004 | Plasson et al. | |
| 6,801,802 B2 | 10/2004 | Sitzman et al. | |
| 6,816,266 B2 | 11/2004 | Varshneya et al. | |
| 6,826,419 B2 | 11/2004 | Diab et al. | |
| 6,870,484 B1 | 3/2005 | Brinsfield et al. | |
| 6,896,661 B2 | 5/2005 | Dekker | |
| 6,907,283 B2 | 6/2005 | Carter et al. | |
| 7,130,671 B2 * | 10/2006 | Baker et al. | 600/310 |
| 2002/0013518 A1 * | 1/2002 | West et al. | 600/300 |
| 2002/0072660 A1 * | 6/2002 | Diab et al. | 600/323 |
| 2002/0137995 A1 * | 9/2002 | Heckel | 600/323 |
| 2003/0055309 A1 | 3/2003 | Kaushansky et al. | |
| 2003/0139656 A1 * | 7/2003 | Kiani et al. | 600/322 |
| 2003/0236100 A1 * | 12/2003 | Fujieda et al. | 455/550.1 |
| 2004/0147818 A1 * | 7/2004 | Levy et al. | 600/300 |
| 2004/0186357 A1 | 9/2004 | Soderberg et al. | |
| 2005/0065417 A1 * | 3/2005 | Ali et al. | 600/323 |
| 2005/0197586 A1 * | 9/2005 | Pearlman | 600/509 |

\* cited by examiner

420(a):

```
Welch Allyn Propaq 802LTRN
   SERIAL#F82C0DD5  V1.00.00

Portland Westside
Emergency Department
PtIdWstsdED10Jun05.mnt
Ann Jones, MD
503-530-0101 X9999
Patient Mode Adult        Snapshots none saved
Wireless Communications Enabled

| Start New Patient | Info | Demo |
```

420(b):

```
Welch Allyn Propaq 802LTON
   SERIAL#AB72383-1  V1.00.00

Portland Westside
Emergency Department
PtIdWstsdED10Jun05.mnt
Ann Jones, MD
503-530-0101 X9999
Patient Mode Adult        Snapshots 14 of 20 saved
Wireless Communications Disabled

| Start New Patient | Continue Patient | Info | Demo |
```

FIG. 26

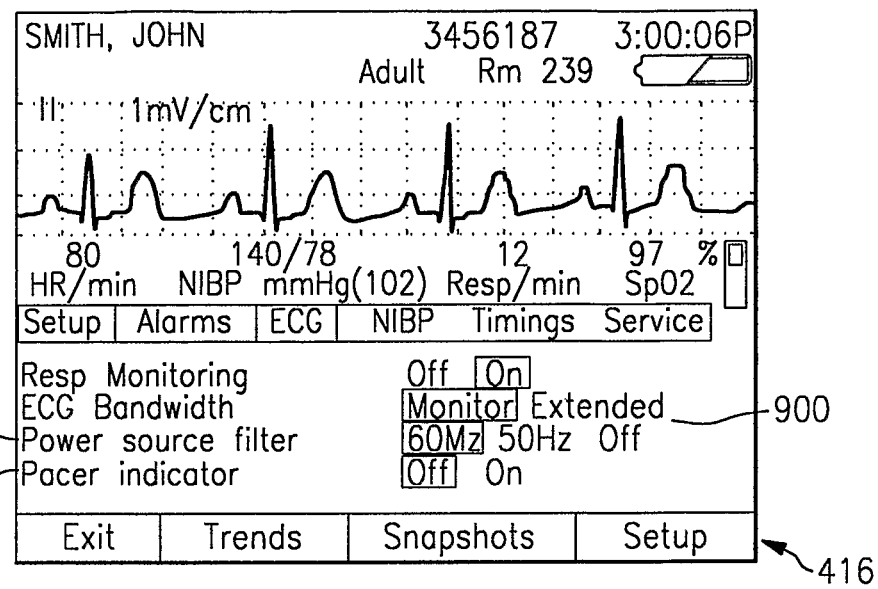
FIG.36
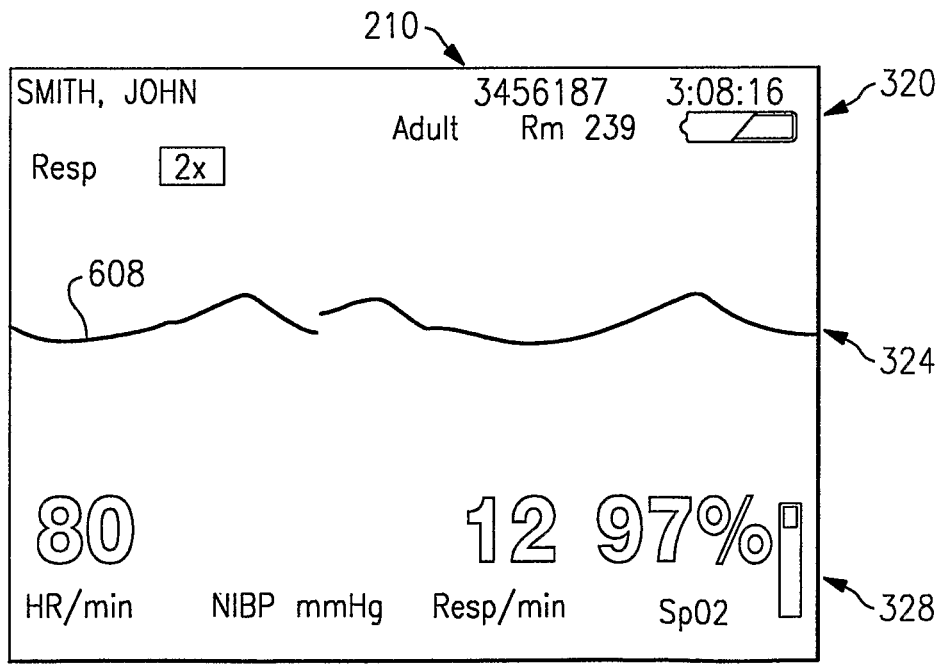
FIG.37
FIG.38

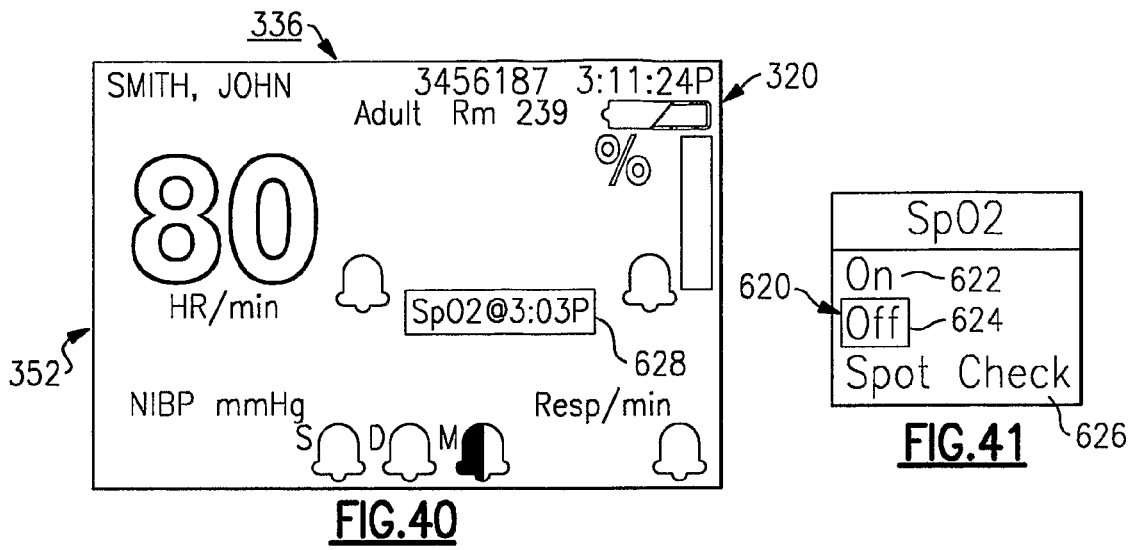
FIG.40
FIG.41
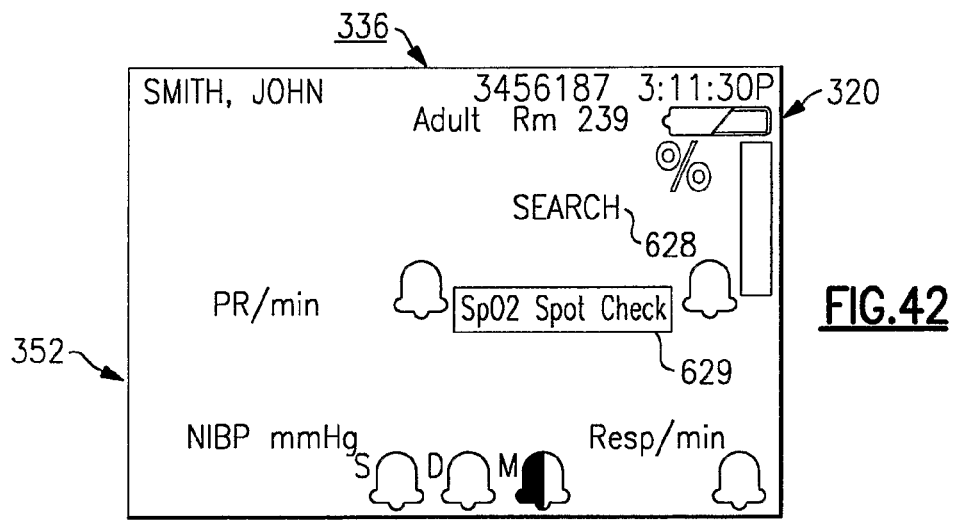
FIG.42
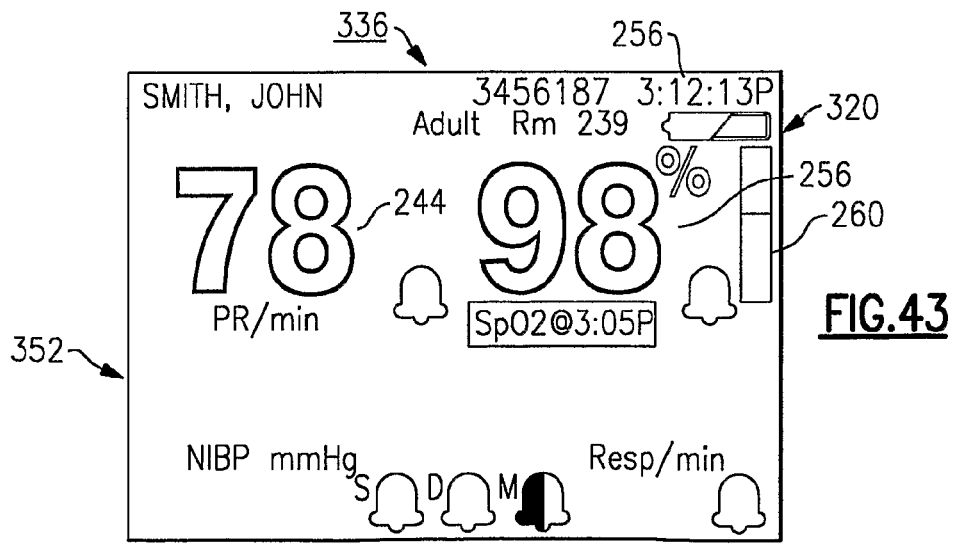
FIG.43

FIG.54

| Time | HR/Min | NIBPmmHg | Resp/min | SpO2 |
|---|---|---|---|---|
| | 59 | 120/72(88) | 14 | 98 |
| 4:42P | 60 | 121/73(89) | 14 | 99 |
| 4:41P | 58 | 119/72(88) | 13 | 98 |
| 4:40P | 📷 59 | 120/72(88) | 14 | 98 |
| 4:40P | 59 | 120/72(88) | 14 | 99 |
| 4:39P | 📷 60 | 118/71(87) | 13 | 98 |
| 4:39P | 60 | 118/71(87) | 14 | 98 |
| 4:38P | 59 | 120/71(88) | 14 | 98 |
| 4:37P | 60 | 119/71(87) | 14 | 99 |
| 4:36P | 60 | 117/70(86) | 13 | 98 |
| 4:35P | 📷 60 | 120/72(88) | 14 | 98 |
| 4:35P | 60 | 120/72(88) | 13 | 99 |
| 4:34P | 59 | 119/72(88) | 13 | 98 |

SMITH, JOHN — 7762940 — 04:45:10P — Adult Rm 263 — Tabular

FIG.55

View Interval:
- 1 min
- 5 min
- 10 min
- 15 min
- 30 min
- 60 min

| Time | HR/Min | NIBPmmHg | Resp/min | SpO2 |
|---|---|---|---|---|
| | 59 | 120/72(88) | 14 | 98 |
| | | 121/73(89) | 14 | 99 |
| | | 119/72(88) | 13 | 98 |
| | | 120/72(88) | 14 | 98 |
| | | 120/72(88) | 14 | 99 |
| | | 118/71(87) | 13 | 98 |
| | | 118/71(87) | 14 | 98 |
| 4:38P | 59 | 120/71(88) | 14 | 98 |
| 4:37P | 60 | 119/71(87) | 14 | 99 |
| 4:36P | 60 | 117/70(86) | 13 | 98 |
| 4:35P | 📷 60 | 120/72(88) | 14 | 98 |
| 4:35P | 60 | 120/72(88) | 13 | 99 |
| 4:34P | 59 | 119/72(88) | 13 | 98 |

SMITH, JOHN — 7762940 — 04:45:12P — Adult Rm 263 — Tabular

| PARAMETER | | ALARMING LEVEL | ALARM LIMIT (PARAMSET =5%) | ALARM LIMIT (PARAMSET =10%) | ALARM LIMIT (PARAMSET =15%) | ALARM LIMIT (PARAMSET =20%) | ALARM LIMIT (PARAMSET =25%) |
|---|---|---|---|---|---|---|---|
| HR/PR | UPPER | 90 | 94 | 99 | 104 | 108 | 113 |
| | LOWER | 60 | 57 | 54 | 51 | 48 | 45 |
| NIBP SYSTOLIC | UPPER | 140 | 147 | 154 | 161 | 168 | 175 |
| | LOWER | 100 | 95 | 90 | 85 | 80 | 75 |
| NIBP DIASTOLIC | UPPER | 90 | 94 | 99 | 104 | 108 | 113 |
| | LOWER | 60 | 57 | 54 | 51 | 48 | 45 |
| NIBP MAP | UPPER | 107 | 112 | 118 | 123 | 128 | 134 |
| | LOWER | 73 | 69 | 66 | 62 | 58 | 55 |
| SpO2 | UPPER | 100 | 100 | 100 | 100 | 100 | 100 |
| | LOWER | 90 | 86 | 81 | 77 | 72 | 68 |
| RESP | UPPER | 20 | 21 | 22 | 23 | 24 | 25 |
| | LOWER | 12 | 11 | 11 | 10 | 10 | 9 |

198

8.1 ParamSet Enable

Do you want to enable ParamSet?

197 — ☑ (Yes)
☐ (No)

Note If you select ☐ (No), disregards the rest of the ParamSet settings.

8.2 ParamSet % for Upper HR/PR

ParamSet increases the Upper HP/PR limit ___%. (5, 10, 15, 20, 25)

8.3 ParamSet % for Lower HR/PR — 199

ParamSet decreases the Lower HP/PR limit ___%. (5, 10, 15, 20, 25)

8.4 ParamSet % for Upper NIBP Systolic

ParamSet increases the Upper NIBP Systolic limit by ___%. (5, 10, 15, 20, 25)

8.5 ParamSet % for Lower NIBP Systolic

ParamSet decreases the Lower NIBP Systolic limit by ___%. (5, 10, 15, 20, 25)

8.6 ParamSet % for Lower NIBP Diastolic

ParamSet increases the Upper NIBP Diastolic limit by ___%. (5, 10, 15, 20, 25)

8.7 ParamSet % for Lower NIBP Diastolic

ParamSet decreases the Lower NIBP Diastolic limit by ___%. (5, 10, 15, 20, 25)

8.8 ParamSet % for Upper NIBP Mean

ParamSet increases the Upper NIBP Mean limit by ___%. (5,10,15)

8.9 ParamSet % for Lower NIBP Mean

ParamSet decreases the Lower NIBP Mean limit by ___%. (5,10,15)

8.10 ParamSet % for Upper SpO$_2$

ParamSet increases the Upper SpO$_2$ limit by ___%. (5, 10)

8.11 ParamSet % for Lower SpO$_2$

ParamSet decreases the Lower SpO$_2$ limit by ___%. (5, 10)

8.12 ParamSet % for Upper Resp

ParamSet increases the Upper Resp limit by ___%. (5, 10, 15, 20, 25)

8.13 ParamSet % for Lower Resp

ParamSet decreases the Lower Resp limit by ___%. (5, 10, 15, 20, 25)

FIG.64

VITAL SIGNS MONITOR

CROSS REFERENCE TO RELATED APPLICATIONS

The following patent application is a national stage application based upon PCT/US/2006/001093, entitled: Vital Signs Monitor, filed Jan. 13, 2006, claiming priority of U.S. Ser. No. 60/643,636, filed Jan. 13, 2005, the entire contents of each above noted application being herein incorporated by reference in its entirety.

FIELD OF THE INVENTION

The invention relates to the field of medical diagnostic instruments and in particular to a portable, battery powered, multi-parametric, vital signs monitoring device that can be used for both ambulatory and transport applications as well as bedside monitoring. The device can be used with an optional charging cradle that supplies power and charges the contained battery. The charging cradle can additionally serve to provide an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station.

BACKGROUND OF THE INVENTION

A number of vital signs monitoring devices are known that are capable of measuring multiple physiologic parameters of a patient wherein various sensor output signals are transmitted either wirelessly or by means of a wired connection to at least one remote site, such as a central monitoring station. U.S. Pat. No. 5,319,363 describes a wired version of such a device and network, while U.S. Pat. Nos. 6,544,173 and 6,544,174 each describe a multi-parametric vital signs monitoring device that is linked by means of a bi-directional wireless communications network with at least one central monitoring station, usually located at a nurse's station on a hospital floor or Intensive Care Unit (ICU). Such monitoring systems have dramatically improved the manner in which patients can be monitored during a hospital stay. However, there is a perceived need in the field to provide a patient monitoring device that is truly versatile, such that the device can be selectively used for bedside as well as ambulatory applications in order to more effectively cover the varied number of situations a monitored patient may encounter, but without a loss in device (e.g., monitoring) connection with that patient or in obtaining required physiologic data.

There are additional concerns that exist in the field of patient vital signs monitoring. For example, the nature of monitoring devices that continuously monitor $SpO_2$ (blood oxygen saturation) levels of a patient can cause false or nuisance alarms, particularly those patients who are of lower acuity or are ambulatory. Traditional continuous monitors of this type are found in ICU, OR, ED, PACU and other specialty beds, for the most part. The majority of hospital beds, on the other hand, are found in medical-surgical and/or general care areas in which non-continuous, spot-checking monitoring devices are primarily used. It is believed that present hospital healthcare dynamics, such as the general shortage of nurses, has increased pressure for regulatory compliance, rising costs, and higher acuity in patient census. The latter, it is further believed, could cause a convergence of continuous monitoring and spot-checking to the un-monitored beds of the hospital. A very large challenge or barrier to this trend is that clinical staff members on medical surgical floors are generally ill-trained or adequately skilled in the use of continuous medical monitoring devices.

There is yet another general need in the field of patient vital signs monitoring to improve the level of alarm management with regard to existing physiologic monitoring devices. Most known devices of this type include at least one visual and/or audible alarm that is produced, typically both at the monitoring device (e.g., bedside) as well as at the central monitoring station. According to one currently known monitoring system, the preset upper and lower alarm limits for all physiologic parameters can be automatically changed simultaneously a single time by a user simultaneously by a specified percentage (e.g., 20 percent). While this form of management/updating is often suitable for certain parameters, such as heart rate, it is not practicable for other parameters (e.g., $SpO_2$). Though some monitoring devices further permit manual adjustment of alarm limits, this adjustment can be a somewhat time consuming and tedious process. As a result, there is a general desire to improve alarm management over presently known patient monitoring devices.

Additionally, there are also a number of patient monitoring devices that can indicate when an electrode assembly, such as those used for ECG electrode assemblies, has already reached failure or has become detached from the patient, such as those described by U.S. Pat. No. 5,819,741 to Karlsson et al. It would be even more desirable, however, to provide a patient monitoring device that can in addition to the above features proactively detect the onset of failure in at least one leadwire/electrode such that the at least one electrode or leadwire could be retrofitted in advance of having the ECG electrode assembly fail during examination or during rounds.

It is a desirable function of any cardiac monitoring device to provide sufficient information so that a clinician can discern if an implanted cardiac pacemaker is operating properly. Basically, it is desirable to include in the ECG waveform a highly visible indication each time the pacemaker fires. As the technology for implanted pacemakers and implanted pacing electrodes has evolved, the magnitude and duration of the pulses that result at the body surface have reduced, making these pulses more difficult to detect. Furthermore, the observed pacer pulse amplitude is smaller in some ECG vectors than in others. Which ECG vectors have the strongest pacer pulse signals is dependent on body surface ECG electrode placement and the location of the implanted pacemaker electrodes, and therefore the detection issues vary from patient to patient. Making the pacer pulse detector in an ECG monitoring device be able to detect smaller amplitude, shorter duration spikes unfortunately causes the detector to trigger more often on the electrical noise spikes that often occur in the patient's vicinity. Faulty incandescent light dimmers, fluorescent lights, electronic power supplies, and other assemblies generate electromagnetic interference (EMI) and other sources of electronic noise may generate such noise spikes, these spikes occurring at a rate that is twice the frequency of the power line. If a pacer pulse detector is triggered this rapidly, it is extremely difficult for the monitoring device to calculate an accurate heart rate. The extent to which these noise spikes affect a pacer pulse detector is further affected by the contact impedance of the body surface ECG electrodes—higher impedance connections make it more likely that these noise spikes will trigger the pacer pulse detector. For each of the foregoing reasons it is therefore desirable to be able to select as an input to a monitor's pacer detector, an ECG vector that contains real pacer pulses whose amplitude is sufficiently above the detection threshold, and which also contains environmental noise spikes whose amplitudes are sufficiently below the detection threshold. To that end, it would be desirable to be able to identify localized areas or sources of electrical noise, in order to permit the clinician to move the patient and/or noise source and thereby avoid instances of premature alerts or other similar situations.

It is yet another general desire in the field of remote monitoring to provide a multiple physiologic parameter monitoring device that is more user-friendly than previous devices of this type; that is, a device that can be more easily and effectively used by staff of varying skill levels.

Still further, there is a general need to provide a more rugged and durable patient monitoring device, given that such devices are finding increased uses, for example, in military field applications, requiring devices of this type to be much more tolerant to shock and environmental loads than those found in classical hospital environments.

SUMMARY OF THE INVENTION

According to an aspect of the present invention, there is herein described a portable, lightweight and battery powered vital signs monitoring device that is capable of being used as an ambulatory or transport monitor and which is optionally patient-wearable. In spite of its lightweight design defined by a compact profile for ease of transport and handheld use, the device is defined by a rugged design that is intended to withstand shock, impact and/or other loads that could be present in literally any patient-related setting or application.

The herein-described monitoring device can also be used in connection with a charging cradle, permitting use of same as a bedside monitor, wherein the charging cradle provides power for the monitoring device in lieu of the contained battery and provides charging for same. In addition, the monitoring device and cradle further permit mounting of same, for example, to either a bed rail and/or a fluid (IV) pole, as needed, or to a large display connected as a peripheral to the device as mounted in the cradle with the cradle having a data port permitting the pass through of data.

The monitoring device further optionally includes an integrated wireless transceiver and antenna, permitting communication bi-directionally with at least one remote station, such as a central monitoring station, over a wireless network. The monitoring device can operate to transmit patient data whether the device is connected to the charging cradle or while in use as a stand-alone unit.

The charging cradle according to one aspect of the present invention further can permit a data-link connection between the monitoring device and a portable computer (PC). According to one version of the invention, the PC can be equipped with configuration utility software and used in order to custom configure the monitoring device for specified usage in a hospital or facility; for example, a neonatal ward. According to another version, the monitoring device is storing "snapshot" data and trended data to be manually or automatically transmitted for printing using the PC with the connected charging cradle acting as an intermediary or pass through device. Alternatively, the charging cradle permits the monitoring device to transmit patient data in a real-time fashion, such as to a large display via the serial connection.

The monitoring device according to another aspect of the present invention is connectable to a plurality of physiologic sensor assemblies wherein multiple patient parameters can be measured, including, for example, blood pressure, $SpO_2$, ECG, pulse/heart rate and respiration. The monitoring device includes an integrated display to indicate the status of the measured physiologic parameters, as well as a user interface, including a keypad, that permits the user to selectively display various output or display modes, including both tabular and graphical data trending of at least one monitored physiologic parameter, as well as to view status of the monitoring device, including connectivity with the wireless network, available power to operate the monitoring device, and other features.

According to yet another aspect of the present invention, the user interface of the monitoring device permits navigation using a series of embedded menus using the keypad (user interface), thereby minimizing the time required for the clinician to obtain relevant data and further permitting highly skilled as well as less skilled clinical staff to equally and effectively utilize the monitoring device. The device further includes security features wherein the buttons of the user interface and/or the display can be locked out or disabled in order to prevent any unauthorized use and power-saving features wherein the display is automatically powered down based on a lack of activity or in which certain assemblies are made inoperative (i.e., NIBP) when a low battery condition exists. In addition and in a wireless version in which the herein described monitoring device is out of range, the wireless data transmission feature can selectively be deactivated until the device is again in range of the network.

According to still another version of the present invention, the user interface is additionally configured to assist the user in terms of alarm management. According to this version of the present invention, upper and/or lower alarm settings or limits for specified measured parameters can be selectively incremented by preset percentage amounts, as needed, during the occurrence of an existing alarm. Additionally, all parameters can be similarly adjusted simultaneously, as needed.

According to yet another aspect of the present invention, the monitoring device permits continuous measurement of certain physiologic parameters, including pulse oximetry. The device, however, can be selectively configured by the user such that the remaining physiologic parameters, such as ECG, can continue to be monitored in the usual manner while $SpO_2$ readings of a patient can be selectively random or spot checked by the user of the monitoring device.

An advantage of the present invention is that a multiparametric monitoring device is provided that can be used in literally any patient setting, allowing the device to be used for monitoring a patient on hospital medical-surgical, telemetry and intermediate floors, hospital emergency departments, transport, emergency medical services and/or other healthcare applications. As such, the herein described monitoring device can be used for and/or between bedside, ambulatory, transport or other similar applications seamlessly.

Moreover, the rugged construction, compact design and adaptability between various bedside and transport applications make the herein described monitoring device extremely useful for military and other similar purposes.

Another advantage of the present invention is that the herein described monitoring device can be custom configured to enable the device to be used in a specific facility. The device can also be temporarily configured for a current patient, wherein settings can be selectively retained for the patient or deleted along with stored data upon power down of the device, thereby facilitating use between patients.

These and other aspects, features and advantages will become readily apparent from the following Detailed Description as well as the accompanying drawings.

BRIEF DESCRIPTION OF THE DRAWINGS

FIG. 26 is an exemplary set of information display windows for the vital signs monitoring device;

FIG. 36 is another example of a function performed in the ECG set-up menu of FIG. 35;

FIG. 37 is an exemplary respiration waveform as displayed by the vital signs monitoring device;

FIG. 38 depicts a portion of an exemplary display screen of the monitoring device and in particular an $SpO_2$ control menu;

FIG. 40 is an exemplary display screen of the vital signs monitoring device of the present invention, including a primary vital signs display screen with the $SpO_2$ icon highlighted after $SpO_2$ has been turned off;

FIG. 41 is a drop down pulse oximeter spot check menu accessed through the window navigation of FIG. 40;

FIG. 42 is an exemplary display screen detailing portions of the $SpO_2$ spot-check feature in accordance with the present invention;

FIG. 43 is a later version of the display screen of FIG. 42 illustrating pulse oximetry data;

FIGS. 54-56 depict various exemplary display screens of tabular trended patient data as displayed by the vital signs monitoring device of the present invention;

FIG. 57 depicts yet another example of a display screen according to yet another display mode for the vital signs monitoring device of FIGS. 1-3, showing trended graphical data;

FIG. 63 is a signal output indicating how electrical noise can be discriminated from pacer signals as detected by the device from a selected ECG vector; and FIGS. 64 and 65 depict portions of an exemplary configuration worksheet used for configuring individual alarm limit settings to predetermined percentage amounts for the monitoring device in accordance with one version of the invention.

DETAILED DESCRIPTION

The following description relates to a specific embodiment for a multi-parametric, vital signs monitoring device that can be used universally for a number of different patient-related applications, including ambulatory, bedside, transport, procedure, and handheld operations. It will be readily apparent, however, from the discussion that follows to those of sufficient skill that numerous variations and modifications are possible within the intended scope of the invention. In addition and throughout the text, a number of terms are used in order to provide a suitable frame of reference with regard to the accompanying drawings, including "top", "bottom", "front", "rear", "back", and the like. These terms are not intended to be over limiting of the present invention, except in those instances where specifically indicated.

Figure 1:
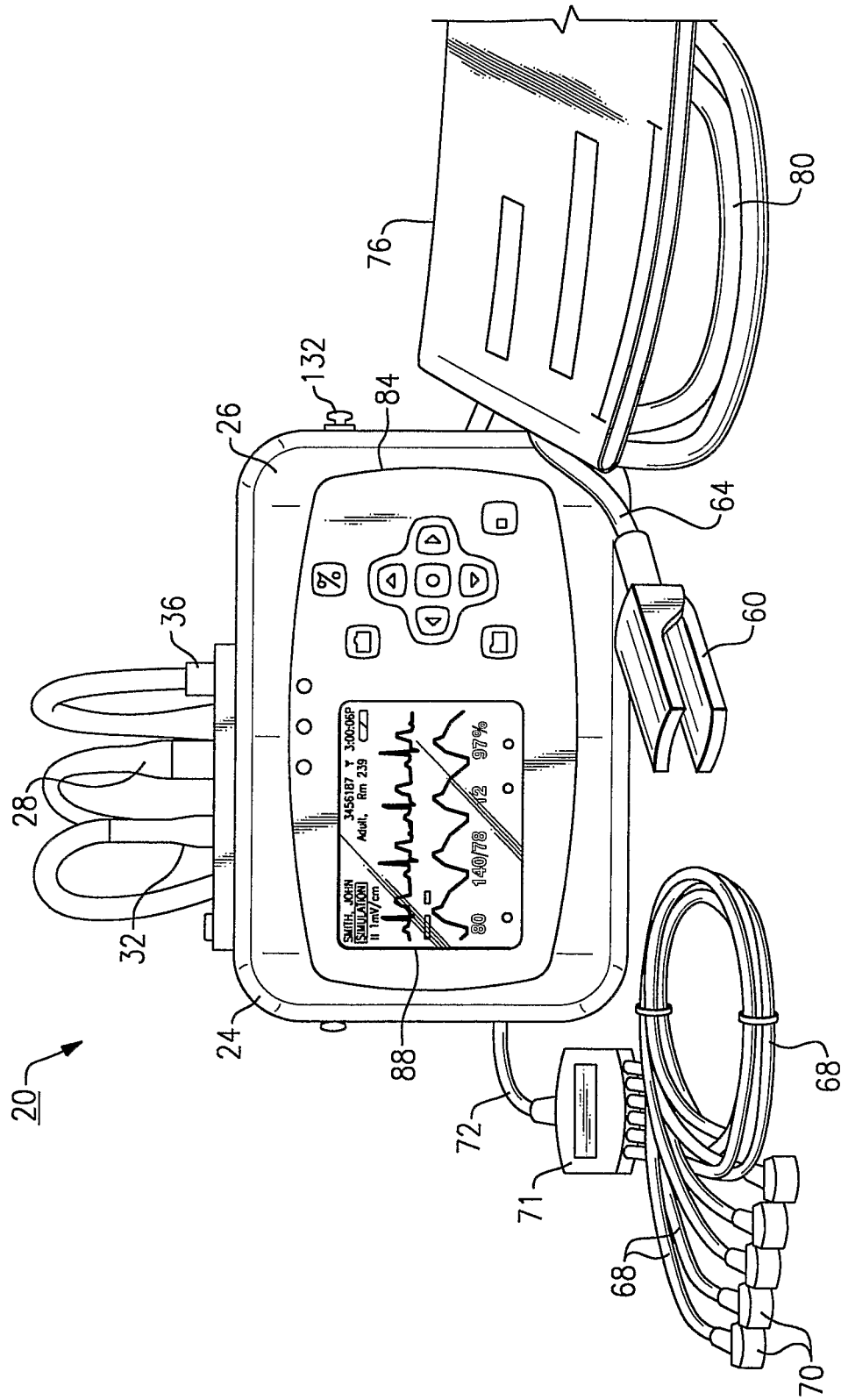
FIG. 1 is a front view of a vital signs monitoring device in accordance with an embodiment of the present invention.

Referring to FIG. 1, the herein described patient monitoring device 20 is defined by a housing 24 that receives input from a plurality of sensors, each forming part of physiologic sensor assemblies 28, 32 and 36, in this instance ECG, SpO$_2$ (pulse oximetry) and blood pressure (NIBP) assemblies. The housing 24 includes a display 88 for vital sign numerics, waveforms and other patient data, as well as a user interface 92, FIG. 2, that permits operation of the monitoring device 20.

Figure 2:
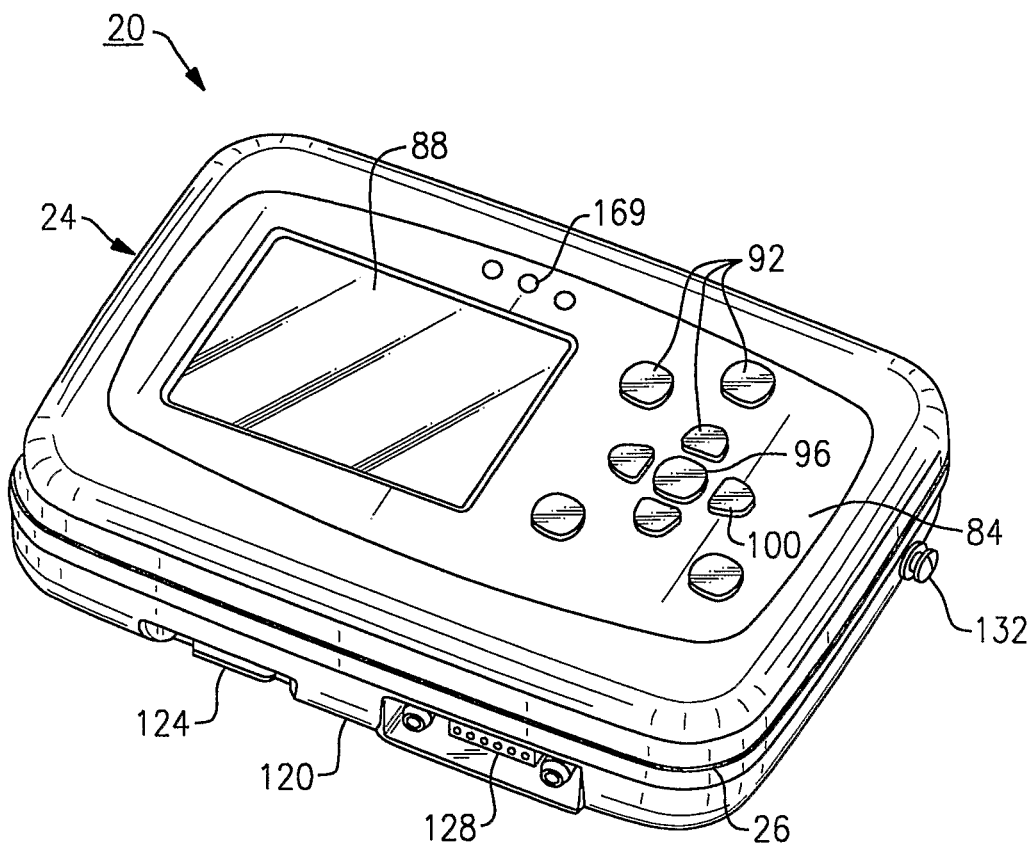
FIG. 2 is a front perspective view of the vital signs monitoring device of FIG. 1.
Figure 3:
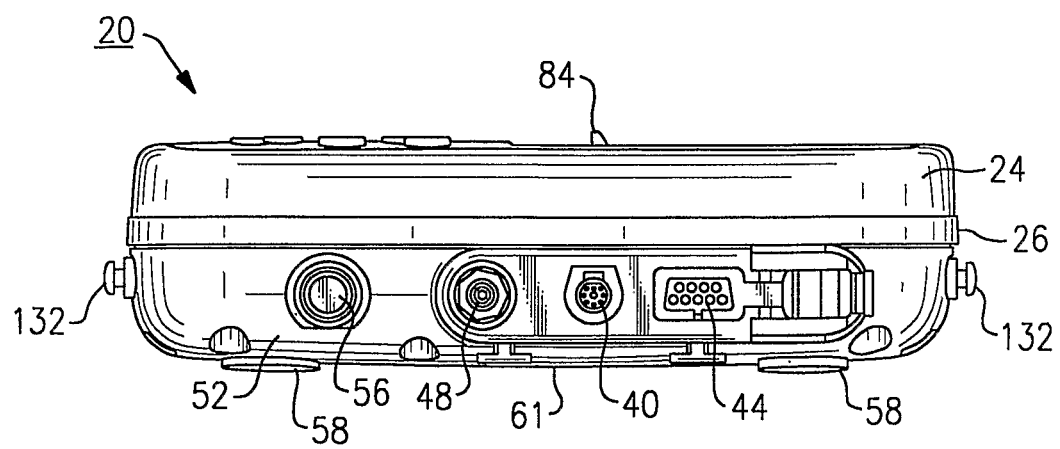
FIG. 3 is a top plan view of the vital signs monitoring device of FIGS. 1 and 2.

Referring to FIGS. 1-3, the display 88 is provided on a front facing side of the housing 24, as well as a plurality of adjacent actuable buttons defining the user interface 92. According to the present embodiment, the display 88 is a quarter (QVGA) color display, the display according to this embodiment being approximately 3.5 inches (measured diagonally). More particularly and according to this embodiment, the display 88 is an LCD having a pixel count of 240 by 320. The herein described display 88 preferably includes a backlight (not shown) to improve readability of the display under low ambient light conditions.

As to the profile of the herein described device 20, the housing 24 according to this specific embodiment is approximately 5.3 inches in height, 7.5 inches in width, and 2.0 inches in depth. In spite of the lightweight design, however, the herein described monitoring device 20 is extremely durable and rugged wherein the device is equipped to handle various loads that may be encountered in a patient-related setting. For example, the housing 24 includes a center or intermediate rubberized bladder 26 disposed between a front housing half and a rear housing half that is disposed peripherally therebetween about the device housing 24 in order to assist in cushioning the monitoring device 20 from impact or shock loads and to retain the interior of the device from dust or other contaminants. To further assist in cushioning the monitoring device 20, each of the corners of the housing 24 are curved to provide an effective contour. A battery compartment (not shown) is also formed within the housing 24, the cover of the battery compartment being essentially flush with the rear facing side 61 of the housing such the compartment does not protrude from the overall profile of the monitoring device 20. The rear facing side 61 of the housing 24 further includes a set of rubberized pads or feet 58, enabling the monitoring device 20 to be placed on a flat surface, as needed. In addition, each of the buttons comprising the user interface 92, discussed in greater detail below, are elastomerized to aid in the overall durability and ruggedness of the monitoring device 20, the buttons being positioned so as not to overly protrude from the facing surface 84 of the housing 24 and allowing the device to maintain a relatively compact profile.

Figure 8:
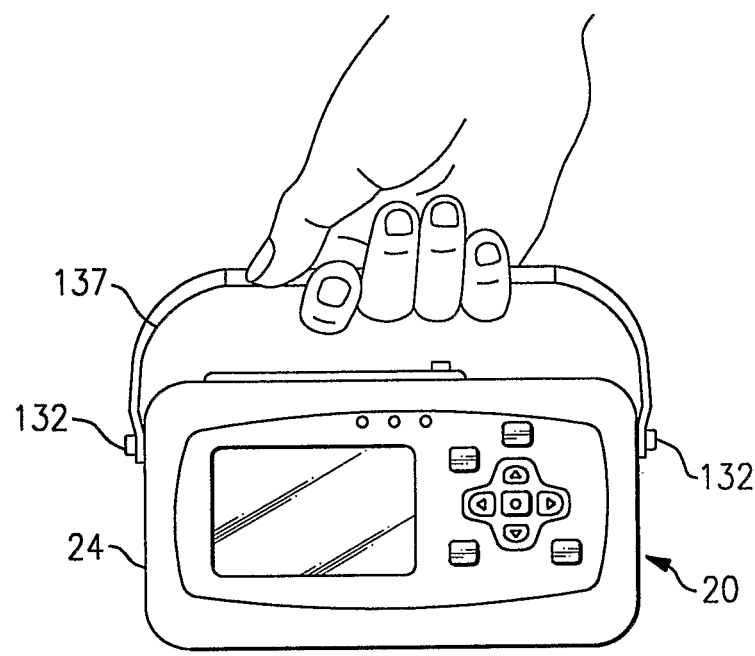
FIG. 8 is a front view of the vital signs monitoring device of FIGS. 1-3 with an attached strap permitting hand-held operation thereof.
Figure 9:
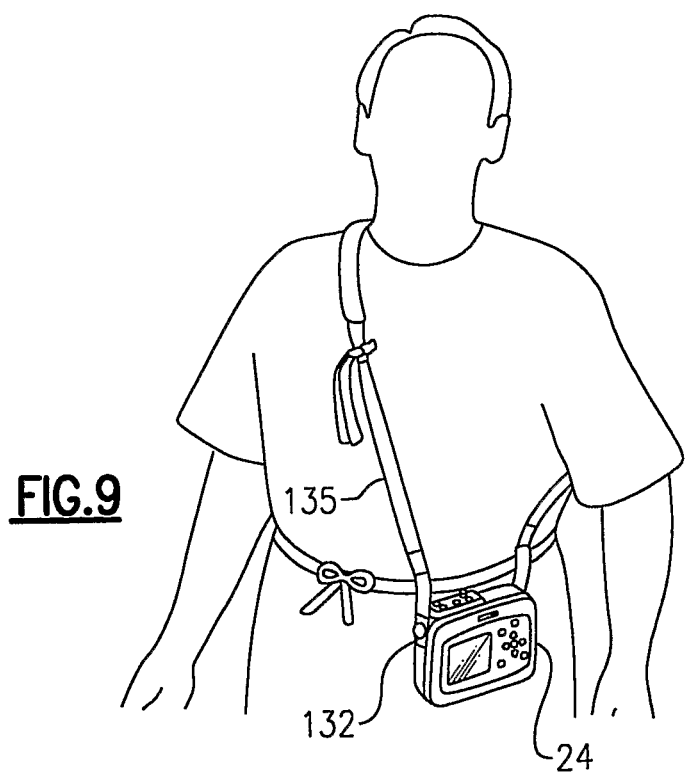
FIG. 9 is a alternative view of the vital signs monitoring device of FIGS. 1-3 using a patient-wearable harness.
Figure 10:
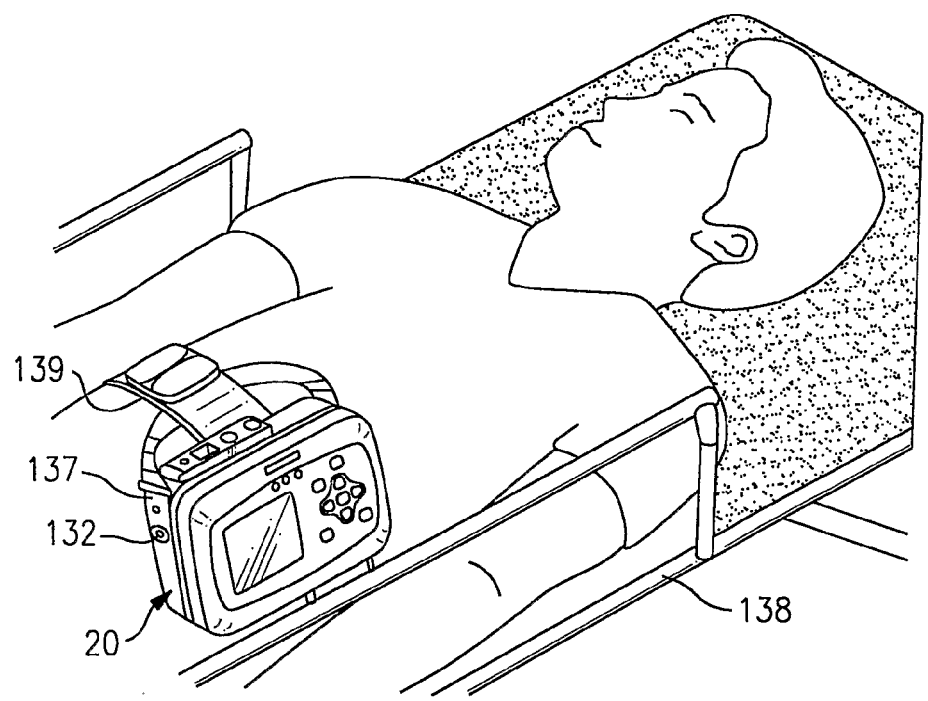
FIG. 10 depicts the vital signs monitoring device of FIGS. 1-3, as used in a patient transport application.

The compact profile of the device housing 24 enables the monitoring device 20 to be patient wearable. A pair of tabs 132, FIG. 2, provided on opposing lateral sides of the device housing 24 enable the monitoring device 20 to be secured to a patient-wearable harness 135, such as shown in FIG. 9, or alternatively a strap 137 can be attached to the side tabs 132, as shown in FIG. 8, permitting hand-held and portable operation of the monitoring device 20. The strap 137 can be used additionally for transport operations along with a transport belt 139, such as shown in FIG. 10, with respect to a gurney 138 or other transport apparatus. Otherwise and as noted above, the herein described monitoring device 20 can be suitably positioned upon a table or other flat surface using the rubberized pads 58 provided on the rear facing side 61 of the device housing 24.

In addition to being compact and durable, the herein described monitoring device 20 is extremely lightweight. The entire assemblage shown in FIG. 1 weighs approximately two pounds.

As noted above and according to this embodiment, a plurality of physiologic sensor assemblies are tethered to the housing 24, including an ECG sensor assembly 28, an SpO$_2$ sensor assembly 32 and a non-invasive blood pressure (hereinafter NIBP) sensor assembly 36, respectively, the sensor assemblies being shown in FIG. 1 only for the sake of clarity.

A brief treatment of each tethered physiologic sensor assembly 28, 32, 36 is now provided for the sake of completeness. More particularly and in brief, the SpO$_2$ sensor assembly 32 is used to noninvasively measure oxygen saturation of arteriolar hemoglobin of a peripheral measurement site of a patient, such as the wrist, a finger, a toe, forehead, earlobe or other area. Reusable or disposable sensor probes can be used. In this instance, a finger clamp 60 is shown in FIG. 1, the clamp having a light emitter and a light detector that can be used to detect pulse/heart rate as well as blood oxygen saturation through pulse oximetry. The finger clamp 60 is tethered by means of a cable 64 extending to a pinned connector that mates with a corresponding female connecting port 44, FIG. 3, that is provided on the exterior of the device housing 24.

The concepts relating to pulse oximetry in general are commonly known in the field and do not form an inventive part of the present invention.

In brief, the ECG sensor or monitoring assembly 28 includes a lead wire assembly, wherein either a three-lead or a five-lead ECG can be utilized according to the present embodiment. More particularly and by way of example, the herein pictured ECG sensor assembly 28 of FIG. 1 comprises a set of lead wires 68, each having electrodes 70 at the ends thereof to permit attachment, in a conventionally known manner, to the body of a patient, the lead wire assembly comprising a harness 71 that is attached to a connection cable 72 having a connector which is matingly attachable to the connection port 40 of the device housing 24. The ECG sensor assembly 28 is further utilized herein with respect to a respiration channel of the herein-described monitoring device 20 in order to determine the rate or absence (apnea) of respiration effort through the determination of ac impedance between selected terminals of ECG electrodes 70, thereby determining the respiration rate of a patient using impedance pneumography based upon movements of the chest wall using a designated reference lead wire. Heart rate according to the present embodiment is detected for the herein described device 20 using the ECG sensor assembly 28.

The ECG sensor assembly 32 creates a waveform (ECG vector) for each lead and further includes a QRS detector that can be adjusted depending upon the patient mode selected. The ECG sensor assembly 28 is further configured to determine heart/pulse rate, if selected, according to the present embodiment as well as mark pacer spikes in the resulting ECG waveforms by way of a pacer detection circuit. The ECG sensor assembly 28 according to the present embodiment further includes selectable notch filters of 50 Hz and 100 Hz, 60 Hz and 120 Hz, respectively.

In brief, the NIBP sensor assembly 36 according to this embodiment indirectly measures arterial pressure using an inflatable cuff or sleeve 76, which is attached to the limb (arm or leg) of a patient (not shown). The remaining end of a connected hose 80 includes an attachment end that can be screwed into a fitted air connector fitting 48 that is provided on the top facing side of the housing 24. The air connector fitting 48 is connected to a pump (not shown) disposed within the monitoring device housing 24 in order to selectively inflate and deflate the cuff 76 to a specified pressure, depending on the type of patient, using the oscillometric method. Pressure changes are detected by means of circuitry in order to determine systolic, diastolic and mean arterial pressure (MAP). The NIBP sensor assembly 36 according to this embodiment is capable of performing manual, automatic and a turbo mode of operation, as described in greater detail below. The assembly 36 can also be equipped, in this embodiment, when ECG is also being monitored, with a motion artifact filter if ECG is also being monitored. The filter according to the present embodiment employs a software algorithm that can be used to automatically synchronize the process of NIBP measurement to the occurrences of the R-wave of the ECG waveform, thereby increasing accuracy in cases of extreme artifact and diminished pulses. An example of a suitable NIBP artifact filter is described in U.S. Pat. No. 6,405,076 B1, the entire contents of which are herein incorporated by reference. Examples of NIBP and ECG sensor assemblies useful for incorporation into the herein described monitoring device 20 are manufactured by Welch Allyn Inc., of Skaneateles Falls, N.Y., among others. With regard to each, the form of sensor assembly can be varied depending on the type of patient, (i.e., adult, pediatric, neonatal) by selective attachment to the connection ports 40, 48 that are provided on the monitoring device 20. Each of the foregoing sensor assemblies according to the present embodiment further include electrosurgery interference suppression. As noted, pulse rate can be detected from either the $SpO_2$ or the NIBP channels of the monitoring device 20.

It is contemplated for purposes of the present invention, however, that other means for connecting the above-noted sensor assemblies 28, 32 to the monitoring device 20 other than through the connection ports 40, 44, including wireless means, such as for example, IR, optical, RF, and other non-tethered connections could also be employed for purposes of the present invention. It should be further noted that the number of types of physiologic sensor assemblies used with the herein described device 20 can be varied and that those shown are intended to only be exemplary of the present invention. The invention contemplates both multiple and single physiologic parameter monitoring of a patient using the monitoring device 20 and therefore such variation is purposely intended.

Figure 6:
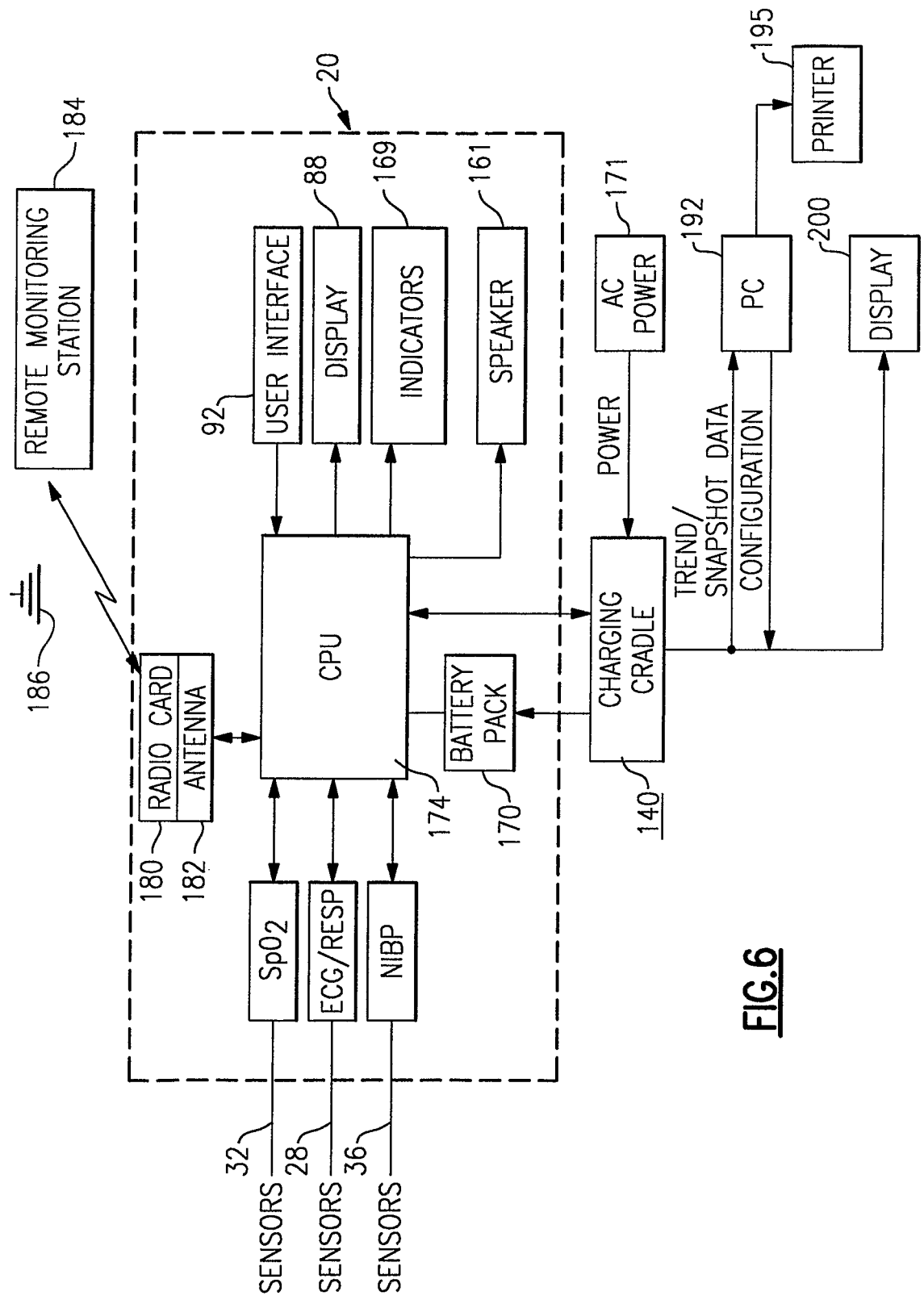
FIG. 6 is a schematic block diagram of a patient monitoring system including the vital signs monitoring device of FIGS. 1-3 and the charging cradle of FIG. 4.

Referring to FIGS. 1 and 6, each of the above physiologic sensor assemblies 28, 32, 36 according to this embodiment are internally connected electrically to a CPU 174 that is contained within the housing 24 of the monitoring device 20. According to this embodiment, signal processing for each of the physiologic sensor assemblies 28, 32, 36 is performed internally through resident processing circuitry; for example, the $SpO_2$ sensor assembly 32 of the present embodiment utilizes the Nellcor Puritan MP506 architecture while the NIBP sensor assembly 36 is based upon a design, such as those used presently in the Micropaq and Propaq vital signs monitors, including, for example, an NIBP Module, Part 007-0090-01, manufactured and sold by Welch Allyn, Inc. Though not shown in FIG. 6, the resident circuitry for each of the sensor assemblies 28, 32, 36 are all integrated into a single logic board wherein the ECG and respiration parameters utilize a common processor, such as a Motorola MPC 823 processor of the CPU 174. Despite being integrated into a single logic board, the remaining physiologic parameters ($SpO_2$ and NIBP) are implemented in a more modular fashion, as shown in FIG. 6, and utilize their own processors. It should be readily apparent, however, that the electronic packaging of the various processing elements of the physiologic sensor assemblies 28, 32, 36 of the monitoring device 20 can easily assume various configurations for purposes of the present invention and other versions could easily be contemplated.

Still referring to the schematic diagram of FIG. 6, the contained battery pack 170 is interconnected to the CPU 174, the latter including a microprocessor, memory, and resident circuitry, wherein each are connected to the tethered sensor assemblies 28, 32, 36 in order to enable processing storage and selective display of the signals provided therefrom as well as perform power conversion between the charging circuit of an optional charging cradle 140 and the contained battery pack, including circuitry to prevent overcharging of the contained battery pack 170 (i.e., 12 volts to 5 volts), as described in greater detail below. The CPU 174 according to this embodiment includes available volatile and non-volatile storage for patient data, in the form of Flash memory and SRAM, though other form as are also possible, the CPU 174 being further connected to the display 88. As noted above, the CPU 174 according to this embodiment is presented on a single logic board along with the processors for the physiologic sensor assemblies 28, 32, 36. The CPU 174 is intended to handle device-specific aspects, such as alarm limits, display generation, and enabling and disabling of certain features, wherein the physiologic sensor assemblies 28, 32, 36 predominantly only relate data for use by the CPU 174. It should be noted that portions of the processing function, for example, the ECG processing algorithms, can also reside in CPU 174, though this can be varied appropriately depending, for example, on the extent of processing power required or packaging concerns. The CPU 174, predominantly controls the operation of the device 20, including patient modes, pressures, voltages and the like, either as a factory default setting, or configured, as described below either through the user interface 92, a remote monitoring station 184, FIG. 6, and/or a connected PC 192, FIG. 6.

In addition to the preceding, the monitoring device 20 as schematically represented in FIG. 6 further optionally includes a wireless radio card/transceiver 180, enabling bi-directional wireless communication with at least one remote monitoring station 184, such as, for example, the Acuity Monitoring Station manufactured and sold by Welch Allyn Inc., using the radio card as inserted in an internal PCMCIA expansion slot (not shown). The radio card 180 according to this embodiment is an IEEE 802.11 compliant radio card that connects to an antenna 182 that is also disposed within the housing 24 of the monitoring device 20 for transmission over a 2.4 GHz frequency hopping spread spectrum (FHSS) wireless local area network (WLAN) using access points 186. Additional details relating to an exemplary wireless interconnection, including networking therewith, is provided in U.S. Pat. No. 6,544,174, the entire contents of which are herein incorporated by reference. Additional discussion of device-specific details relating to the wireless connection of the herein described monitoring device 20 is provided in a later portion of this description.

As most clearly shown in FIG. 2, a lower or bottom facing surface 120 of the device housing 24 includes a latching member 124, FIG. 2, as well as an electrical port 128, FIG. 2, each of which are used in conjunction with an optional charging cradle 140, FIG. 4, described in greater detail below. As previously noted, the battery pack 170, only shown schematically in FIG. 6, is contained in the rear of the device housing 24 within a rear compartment (not shown). The battery pack 170 provides portable power for the monitoring device 20 wherein the battery life is dependent upon certain operational modes of the device, as described below. The battery pack 170 is rechargeable by means of charging circuitry contained within the optional charging cradle 140, FIGS. 4, 5. According to this embodiment, the battery pack 170 includes at least one rechargeable lithium-ion battery, such as those manufactured by Sanyo Corporation. In this instance, the battery pack 170 includes two rechargeable batteries. According to the present embodiment, the monitoring device 20 is capable of operation in a stand-alone mode using the contained battery 170 as a power source, the battery according to this embodiment having an average runtime of up to approximately 24 hours, depending on the usage of the device.

Figure 4:
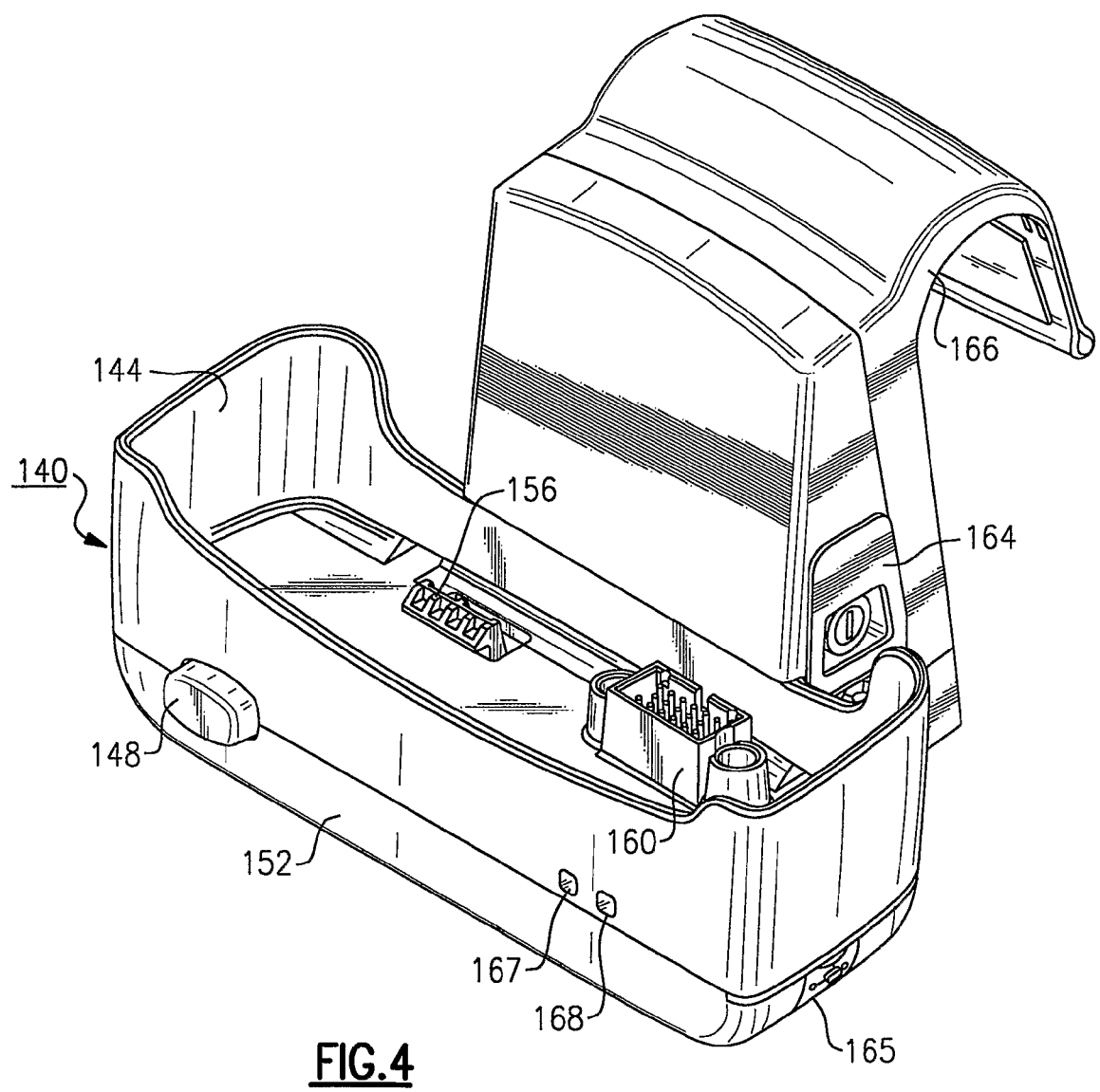
FIG. 4 is a front perspective view of a charging cradle that is used in connection with the vital signs monitoring device of FIGS. 1-3.
Figure 5:
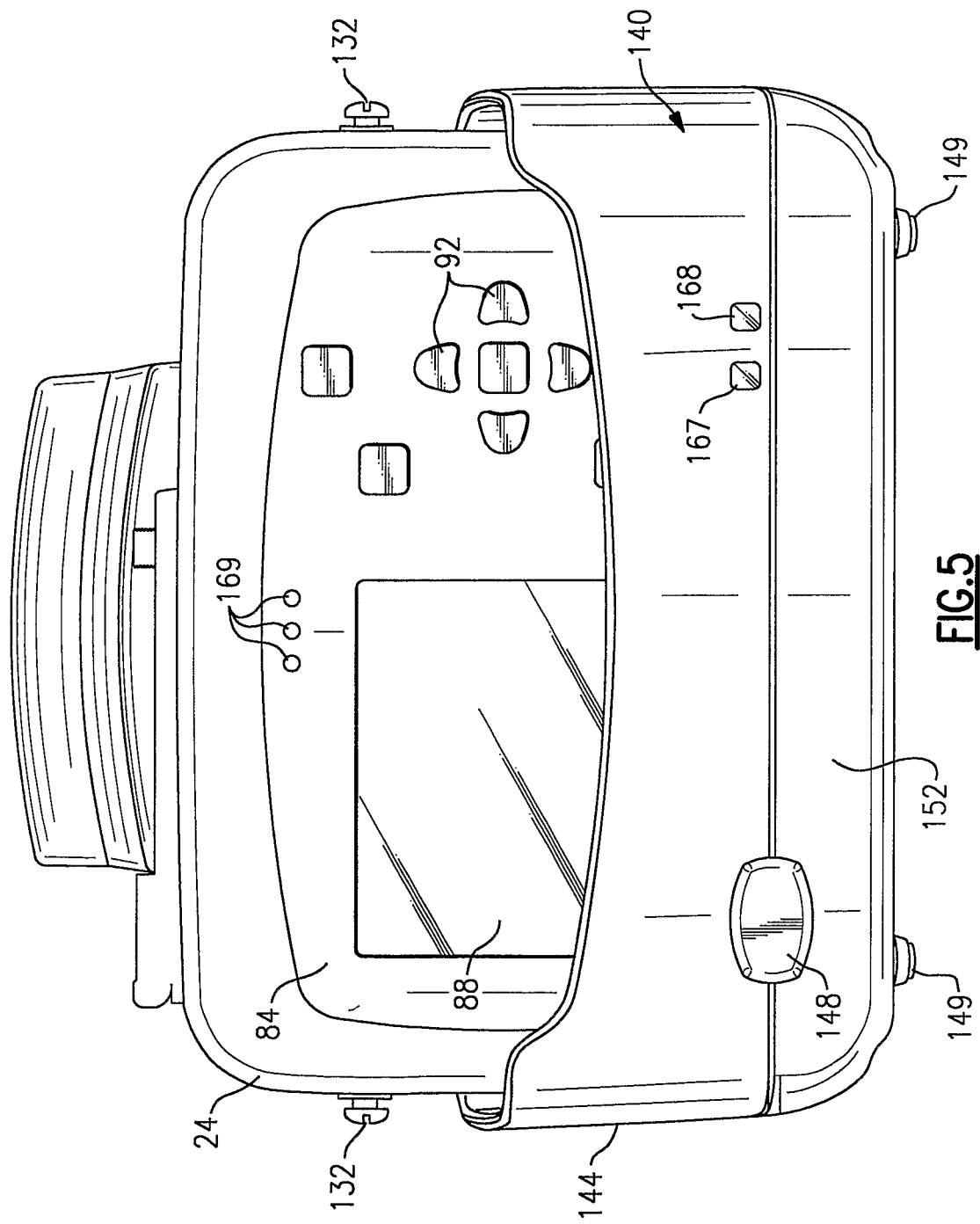
FIG. 5 is a front view of the vital signs monitoring device of FIGS. 1-3 as mounted in the charging cradle of FIG. 4.

Referring to FIGS. 4-6, details relating to the charging cradle 140 and its optional connection with the monitoring device 20 are herein described. The charging cradle 140 permits DC power from a wall adapter 171, shown only schematically in FIG. 6, or other source to be supplied to the contained rechargeable battery pack 170 through charging circuitry contained in the cradle and power conversion circuitry contained in the monitoring device. The use of the optional charging cradle 140 permits the monitoring device 20 to be operated regardless of the status of the contained battery (i.e., charged or uncharged), therefore enabling use of the monitoring device 20 as a stand-alone or networked bedside monitor. That is, the foregoing operation can permit both the internal display of patient data as well as wireless transmission of stored patient data to the central monitoring station 184.

Structurally, the charging cradle 140, according to the present embodiment, is defined by an open-topped receptacle 144 having a molded or otherwise defined internal cavity that is sized to receive the lower half of the monitoring device 20. The receptacle 144 is designed to allow operation of the monitoring device 20 via the user interface 92, as shown in the attached view of FIG. 5, when the device is attached thereto. A monitor release button 148 is provided on a front facing side 152 of the receptacle 144. The monitoring device 20 is engaged by aligning the bottom facing surface 120, FIG. 2, of the device housing 24 with the internal cavity of the receptacle 144 and more specifically aligning the latching member 124 provided thereupon with a pivotally movable locking or latching element 156 that is disposed within the bottom of the internal cavity of the receptacle 144. A pinned electrical connector 160 adjacent the latching element 156 mates with the corresponding electrical connector 128, FIG. 2, provided on the bottom facing side 120, FIG. 2, of the device housing 24, FIG. 2, and thereby provides electrical connection between the monitoring device 20 and the charging cradle 140, as schematically shown in FIG. 6. Engagement of the latching member 124 with the latching element 156 locks the monitoring device 20 in place wherein depression of the monitor release button 148 causes the latching element 156 to be pivoted out of contact with the latching member 124, allowing release of the monitoring device 20 from the charging cradle 140.

Figure 11:
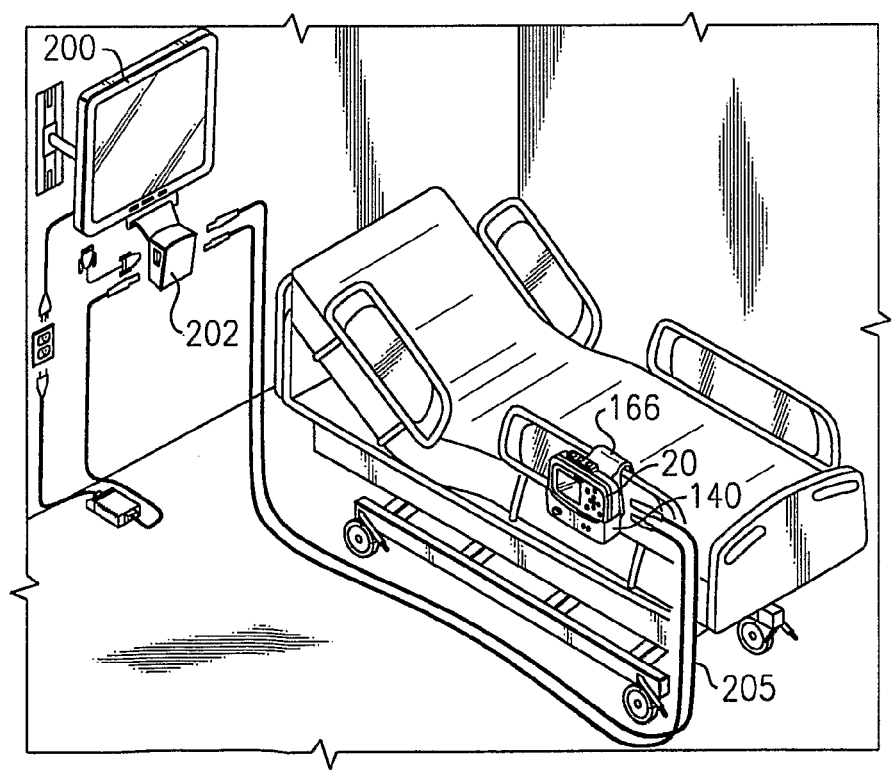
FIG. 11 depicts the vital signs monitoring device of FIGS. 1-3 as mounted to a bed rail and attached to a large display.

A rear engagement portion 164 of the charging cradle 140 includes a curved hanging bracket 166, permitting the charging cradle and attached monitoring device 20 to be attached to a bedrail, as shown, for example, in FIG. 11. Alternatively, the hanging bracket 166 can further include at least one other mount (not shown) that permits attachment to separate apparatus, such as a fluid-IV pole (not shown). In one version, the hanging bracket 166 can include both attachment modes (bedrail, IV pole). The hanging bracket 166 is separably removable by way of threaded fasteners (not shown) or other means from the rear engagement portion 164 to permit other attachment arrangements, such as those discussed below with reference to FIGS. 11-13. The bottom surface of the charging cradle 140 according to this embodiment further includes a plurality of support feet 149, FIG. 5. According to this embodiment, the support feet 149 are provided at each corner of the bottom surface in order to permit placement onto a flat surface, such as a table 203, FIG. 12.

A pair of indicators 167, 168 are provided on the front facing side 152 of the charging cradle 140 wherein according to this embodiment indicator 167 is a status indicator and indicator 168 is a power indicator. The power indicator 168, in this instance, a green LED, indicates that power is connected to the charging cradle 140. The status indicator 167, in this instance, a multi-colored LED, is used to indicate the charging status of the monitoring device 20. For example and if the monitoring device 20 is in the charging cradle 140 and power is properly connected to the charging cradle from the wall adapter 171, FIG. 6, the status indicator 167 will be illuminated (e.g., either green or yellow) or will be off. When the status indicator 167 is green, charging is proceeding normally. The status indicator 167 is turned off when the battery pack 170 reaches full charge. When the status indicator 167 is yellow, the indicator indicates that a fault has occurred and the battery pack 170 is not charging properly. Such faults may occur, for example, as those caused by a severe discharge of the battery 170, a cradle logic fault, incorrect seating of the monitoring device 20 within the charging cradle 140, improper engagement of the connectors or other similar anomaly.

In spite of most charging faults, as noted above, power will not be interrupted to the monitoring device 20. That is, the power indicator 168 may be illuminated (e.g., green), indicating power is capable of being delivered to the monitoring device 20 in spite of the fact that a charging fault (yellow) has occurred. Each time the monitoring device 20 is placed into the charging cradle 140 according to this embodiment, the cradle attempts to charge the contained battery pack 170. If the battery pack 170 is fully charged when the monitoring device 20 is inserted into the charging cradle 140, the status indicator 167 turns green momentarily and upon sensing of a full charge, the indicator is turned off. In the instance that the battery is overcharged at the device 20, however, no power for charging the battery pack 170 will be delivered to the device.

Typically, the herein described monitoring device 20 is shipped to a user/facility with a preset factory configuration for each setting and behavior of the device. It is desirable for most facilities to reconfigure any received patient monitoring device 20 to conform the device to local protocol and adapt the device to the clinical environment to which the device will be used. For example, the monitoring device 20 might be used in a neonatal unit although the factory calibration/configuration is preset for adult patients. Although the user could custom configure the monitoring device 20 upon each use to allow the device to be used for neonatal patients, as described in greater detail herein, it may be preferable to have neonatal mode installed as the default patient mode for a monitoring device.

According to the present invention, a PC 192, FIG. 6, can be used in conjunction with the charging cradle 140 to download a new configuration file to the monitoring device(s) 20 prior to use in a facility for service. According to the present embodiment, the charging cradle includes a USB data port 165, FIG. 4, provided on the exterior of the charging cradle 140 that provides an isolated serial data-link connection between the attached monitoring device 20 and the personal computer (PC) 192, FIG. 6, through a USB cable.

Using a configuration utility supplied through the data link with the PC 192, the charging cradle 140 serves as an intermediary or pass through to the monitoring device 20 to configure the monitoring device prior to use in a facility by creating a configuration file that includes a plurality of setting choices that can be completed, for example, by the bioengineer of the hospital, to adapt onto or to replace pre-existing factory settings initially provided with the device 20 that are stored or programmed within the CPU 174. According to this embodiment, the PC 192 includes utility software that enables the creation of a utility configuration worksheet into which default settings and limits can be entered. The worksheet is then converted into the new configuration file that is downloaded into the CPU 174 of the monitoring device 20 through the intermediary charging cradle 140. As many as approximately 60-70 different settings, depending on the device, can be preset using the downloaded configuration file wherein some of these features, if not enabled, cannot be controlled by the clinician/user. These settings can include, for example, the default language of the monitoring device 20, the default patient mode of device operation, forms of display available to the user and/or their ordering, the enablement of device specific features, such as, for example, lockout of the user interface 92 and display 88, time limits on alarms and alerts, data trending, and the enablement of alarm and alert tones. All or certain of the factory settings can be adjusted by appropriate entries provided on the configuration worksheet created at the PC 192 and communicated through the data link between the CPU 174 and the PC 192. Therefore, this PC configuration results in a set of revised default settings and monitoring device behaviors.

Figures 63, 65:
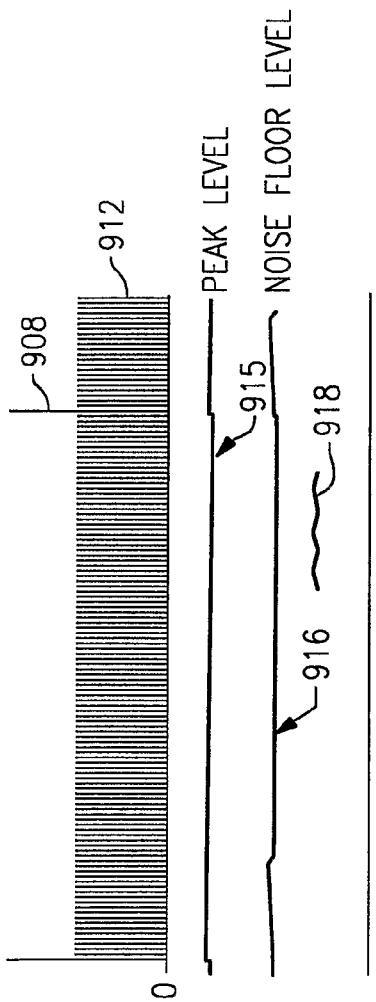

A portion of an exemplary configuration worksheet is shown in FIGS. 64 and 65 with regard to one specific feature that can be enabled with regard to alarm management. Specifics relating to this feature are described in greater detail in a later section. The worksheet 198 shown is a paper version that is completed by a user in advance to using the configuration utility, the latter providing a PC worksheet version that provides similar entries. The user completes the paper configuration worksheet 198, FIG. 64, to organize the features for configuration or can directly input selections into the utility worksheet provided at the PC 192, FIG. 6. Once all entries have been made, the configuration file is created with instructions to override the factory settings when the file is downloaded to the monitoring device 20 through the serial data link provided by the charging cradle 140.

As will be described in greater detail below, the PC 192, FIG. 6, also permits stored data to be printed automatically when the monitoring device 20 is activated and attached to the charging cradle 140, also using the associated USB data port 165, FIG. 4. In this instance and referring to FIG. 6, the PC 192 is connected to a suitable peripheral printer, in this instance, a laser printer 195, also schematically shown in FIG. 6, wherein the monitoring device 20 and PC are programmed to automatically permit data transfer to occur. According to this embodiment, the data that is stored is in the form of trended data and "snapshots", the latter term referring to numeric and waveform data covering a predetermined time period that is electively taken by a user using the snapshot button 116. Pressing the snapshots button 116, FIG. 7, located on the device housing 24, FIG. 2, causes data occurring a predetermined time period prior to pressing the button and a predetermined time period after pressing the button to be stored by the CPU 174. Details relating to stored trend and snapshot data are provided in a later portion of this description.

Figure 12:
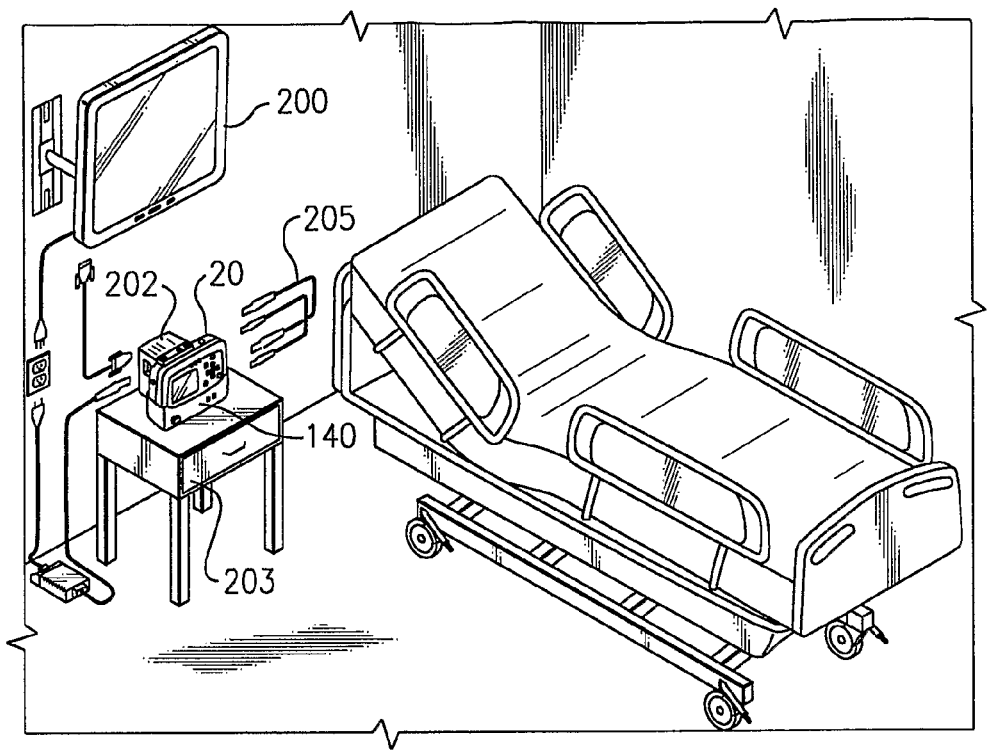
FIG. 12 depicts the vital signs monitoring device of FIG. 11 as attached to a charging cradle and an interface housing for the large display.
Figure 13:
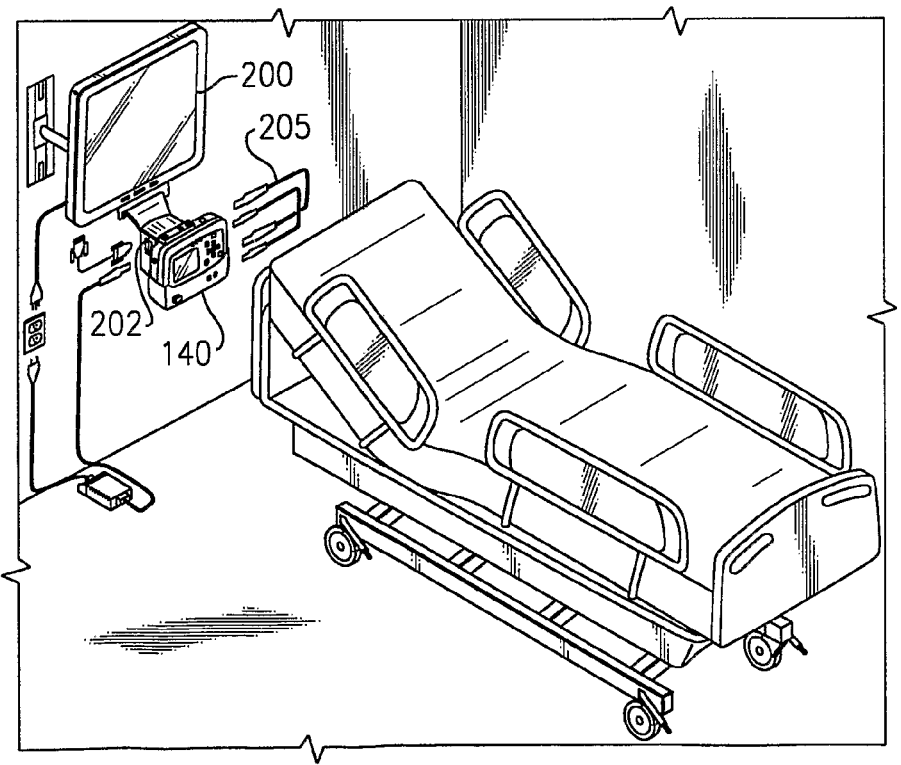
FIG. 13 depicts the vital signs monitoring device of FIGS. 11 and 12 as mounted in a charging cradle and directly attached to the large display.
Figure 14:
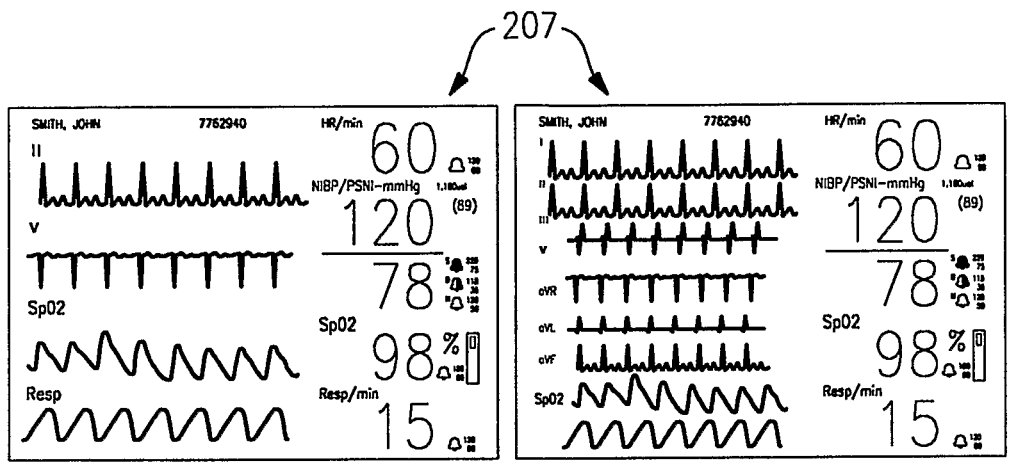
FIG. 14 illustrates two sample display screens indicative of the information that can be captured by the vital signs monitoring device of FIGS. 1-3 and displayed by the large display.

Referring to FIGS. 6 and 11-14, the charging cradle 140 can alternatively serve to provide an intermediary interconnection between the herein described monitoring device 20 and a large display 200. This form of interconnection permits all processed data in the monitoring device 20 to be transmitted in real time in order to permit viewing of the data substantially as though users were at the central monitoring station 184, as opposed to the smaller and constricted device display 88. That is, a series of waveforms can be displayed for viewing, for example, as shown in FIG. 14. The large display 200 according to this embodiment includes a VGA card and suitable attachment bracketry in the form of an interface box or housing 202. Several embodiments for interconnection of the monitoring device/charging cradle assembly to the large display 200 through the interface box 202 are illustrated in FIGS. 11-13. In each embodiment, the monitoring device 20 is already attached to the charging cradle 140 in the manner described above. According to FIG. 11, the charging cradle 140 is attached to a bedrail using the hanging bracket 166. A VGA cable 205 is then connected from the USB data port 165, FIG. 4, to connectors that are provided on the interface box 202. As such, the charging cradle 140 serves as an intermediary for data transfer from the patient monitoring device 20. As shown in FIG. 12, the curved bracket 166, FIG. 4, can be removed from the rear engagement portion 166, FIG. 4, of the charging cradle 140 and the monitoring device 20/charging cradle 140 can be placed on a table 203 adjacent the large display 200, the latter being attached in each instance to a wall. In the latter example, the interface box 202 is directly attached to the rear of the charging cradle 140. Finally and as shown in FIG. 13, the monitoring device 20 and charging cradle 140 can be attached to the interface box 202 directly on the large display 200 through the display bracketry and bracketry that is provided on the charging cradle 140, respectively. A sample data output of the large display 200 is shown in FIG. 14, this output substantially replicating that seen by the remote monitoring station 184, FIG. 6, and considerably an increased amount of data than is viewable on the integrated display 88.

It is further contemplated within the spirit and scope of the present invention that the charging cradle 140 can include additional features to provide a level of adaptability for a system incorporating the herein described monitoring device 20. For example, an additional physiologic parameter assembly could be attached to the charging cradle 140 in lieu of or in addition to the monitoring device 20 wherein physiologic data could still be uploaded to the monitoring device 20 when the device is attached to the charging cradle for wireless transmission to the central monitoring station 184, FIG. 6. Similar configurations should be readily apparent. For example, the charging cradle 140 can be equipped with at least one physiologic sensor assembly (not shown) wherein data collected by the at least one sensor assembly can be inputted to the CPU 174 of the monitoring device 20 for display and transmission.

With regard to running time available on the monitoring device 20 when the device is not mounted in the charging cradle 140, the life of the battery pack 170 is highly dependent on the use mode of the device. As noted above and according to this embodiment, about 24 hours of runtime is possible. The level of battery charge is displayed by the monitoring device 20 according to this embodiment, as described below.

Figure 7:
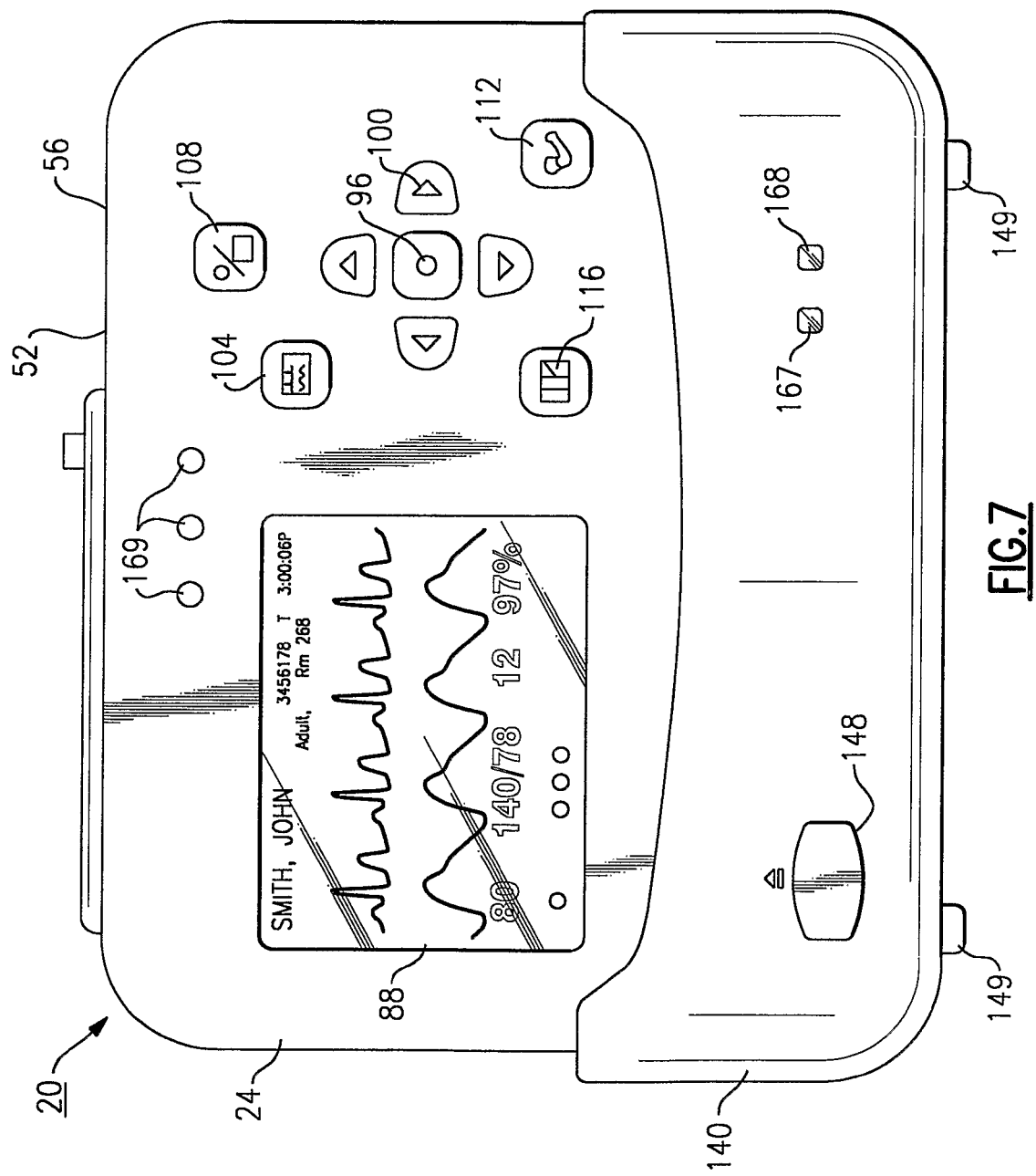
FIG. 7 is another front view of the vital signs monitoring device of FIGS. 1-3 as mounted in the charging cradle of FIGS. 4 and 5, illustrating the user interface thereof.

Referring to FIG. 7, the user interface 92, FIG. 2, according to this specific embodiment includes five (5) closely arranged buttons forming a keypad. In brief, a center button, referred to throughout as a SELECT button 96, is generally used to select a highlighted item that is displayed by the device, as discussed in greater detail below, or to confirm a choice. Four buttons 100 immediately surrounding the SELECT button 96 are generally used (up, down, left or right) in order to directionally guide a display cursor in order to highlight an item, for example, or to increase or decrease a selected parameter value. A number of additional actuable buttons are also provided, according to this embodiment, on the front facing side 84 of the housing 24, these buttons being used for specified or dedicated purposes, including a display button 104, permitting the user to cycle between a plurality of varied display formats, such as those shown in FIGS. 15-19, an alarm silence/resume button 108 permitting the user to temporarily and manually silence or resume an existing patient alert/alarm tone, an NIBP start/stop button 112 for manually starting or stopping an NIBP measurement, and finally the above referred to snapshots button 116 that automatically stores a predetermined time period of vitals-signs data in both tabular and waveform format, an exemplary snapshot display screen being shown in FIG. 50. Each of the above-described buttons further include a visual representation of their function for ease of use by the clinician; for example, the directional control buttons 100 include specific directional arrow indicators, the display button 104 includes a display icon, the NIBP start/stop button 112 includes a depiction of a blood pressure cuff, the snapshots button 116 includes a camera icon and the SELECT button 96 depicts a circle thereupon. Additional details concerning the functions defined by each of the above-listed buttons, and the implementation and operation of the user interface 92 of the herein described monitoring device 20 will be described in greater detail in a succeeding section of this description.

Referring to FIGS. 2, 5 and 7 and in addition to the above user interface 92, a series of visual status indicators are also provided on the front facing side 84 of the monitoring device 20. Three status indicators 169 are arranged in linear fashion above the display 88 at the center of the front facing side 84 of the device housing 24, and are electrically connected to the CPU 174, FIG. 6. Among the purposes of the visual status indicators 169 according to this embodiment are to apprise the user of the operational status of the monitoring device 20; that is, whether the monitoring device 20 is operating normally, confirmation of the connection of the monitoring device 20 and the proper patient being connected to a network or to a remote monitoring station 184, FIG. 6, and/or whether the herein monitoring device 20 is subject to an alarm and/or alert condition. It should be readily apparent that the number and location of these indicators can be suitably varied.

More specifically and according to the present embodiment, each of the status indicators 169 are illuminated with a specific colored light (e.g., red, yellow or amber, and green), indicating an alarm condition, an alert condition, and normal operation of the monitoring device 20, respectively. For purposes of definition herein, an "alarm" is indicative of a patient condition, such as vital signs reading(s) that is outside of acceptable limits. When an alarm condition occurs, for example, the red indicator 169 is illuminated. An "alert" condition, by comparison, is not as serious as an "alarm" condition and is typically indicative of a device-operational problem, such as a low or discharged battery or a detached lead. The yellow status indicator 169 is illuminated when this type of condition is indicated. Normal operation is signified by illumination of the green indicator 169. The status indicators 169 can further either illuminate steadily or flash in order to indicate the severity of the problem. For example and according to this embodiment, this severity can be defined between an equipment alert and an alarm condition. The monitoring device 20 further includes a speaker 161, shown only schematically in FIG. 6, for signifying audible tones, as needed, for example, that may be sounded during an alarm or alert condition. Additional details relating to alarm and alert management using the herein described monitoring device 20 are described in a later portion.

Each of the tethered sensor assemblies 28, 32, 36 provide physiologic parameter data in the form of analog signals and the like to the CPU 174 of the monitoring device 20. The herein described monitoring device 20 is capable of continuously monitoring each of the physiologic parameters (NIBP, pulse rate, 3 and 5 lead ECG, respiration, $SpO_2$) depending on the number and type of sensor assemblies that are connected therewith.

As depicted in the operational block diagram of FIG. 6 and as previously noted herein, each of the $SpO_2$ sensor assembly 32 and the blood pressure (NIBP) sensor assembly 36 according to this embodiment include their own individual processors contained within the monitoring device 20 that operate the sensor assemblies with regard to the acquisition of and processing of data (that is, each of the above sensor assemblies include appropriate algorithms and resident circuitry for processing the acquired signals). The ECG/respiration sensor assembly 28 according to this embodiment includes attendant circuitry within the CPU 174. As previously noted, any or all of the sensor assemblies can include modular processors or the processing can be carried out within a single integrated logic/CPU board. The signals then being processed are stored into the memory of the CPU 174 for display and for wireless transmission using the contained transceiver 180 and antenna 182 to the central monitoring station 184 using the communications network, as described in the previously incorporated U.S. Pat. No. 6,544,174. Additional data, such as patient demographics, can be added for storage and display by the user, as discussed below, or may alternately be uploaded to the monitoring device 20 from a list of available patients from the remote station 184. The monitoring device 20 can transmit patient information, once configured with the network, for display of all stored parametric data at the remote monitoring station 184. The monitoring device 20 is also connectable through the USB port 165, FIG. 4, of the charging cradle 140, enabling operation as a bedside monitor in which serial attachment to the PC 192 through the USB port 165 enables interconnectivity to a peripheral device, such as a printer 195, as previously described or alternatively, to the larger display 200. In the meantime, the monitoring device 20 can also transmit wirelessly to the remote monitoring station 184 using the connected radio 180 and antenna 182.

The versatility of the herein described monitoring device 20 therefore provides a number of distinct advantages. First, the herein described monitoring device 20 can be used as a transport monitor in that the device is battery powered. Second, the use of the rubberized back feet or pads 58, the rear interior loading of the battery pack 170 and general packaging and compactness of the profile of the monitoring device 20 present a lightweight and extremely versatile unit that allows for both wired and wireless connectivities enabling the device to work in either a stand-alone or a networked capacity. The charging cradle 140, FIG. 4, permits the monitoring device 20 to be used for bedside applications by providing a source of power for the contained battery pack 170 as needed and for charging same. In addition and through use of the data port, the charging cradle 140 serves as an intermediary device that enables data transfer to either a large display 200 or printing to a locally connected computer 192. The locally connected computer 192 can also be used to selectively modify factory programmed configuration settings of a monitoring device 20 through new default settings that can be downloaded to the monitoring device 20.

The following discussion relates to the operational aspects of the monitoring device 20. Reference is made throughout to numerous exemplary display screens that are generated by the CPU 174 of the herein described monitoring device 20. Each display screen is defined by a stored preformatted template consisting of a number of discrete panels with each panel including a number of elements that are defined by various combinations of textual, numeric, waveform, graphical and/or other forms of data, as described herein that are obtained from the CPU 174 and generated onto display 88.

Upon powering up the herein described monitoring device 20 using the Power On/Off button 56, an audible tone from the contained speaker 61, FIG. 6, is sounded. With each activation of the monitoring device 20 according to this embodiment, a self-diagnostic or operational test is initiated. If the self test is unsuccessful, at least one of the status indicators 169 of the monitoring device 20 is illuminated, depending on the error. In terms of a general overview and if the self test is successful and following this diagnostic, a start-up display screen 400(a), 400(b), FIG. 24, appears on the display 88, FIG. 1, with the display screen having user-selectable options to continue monitoring a patient (in the event patient data has been saved), start monitoring a new patient, obtain system information, or enter a demonstration mode.

Figure 24:
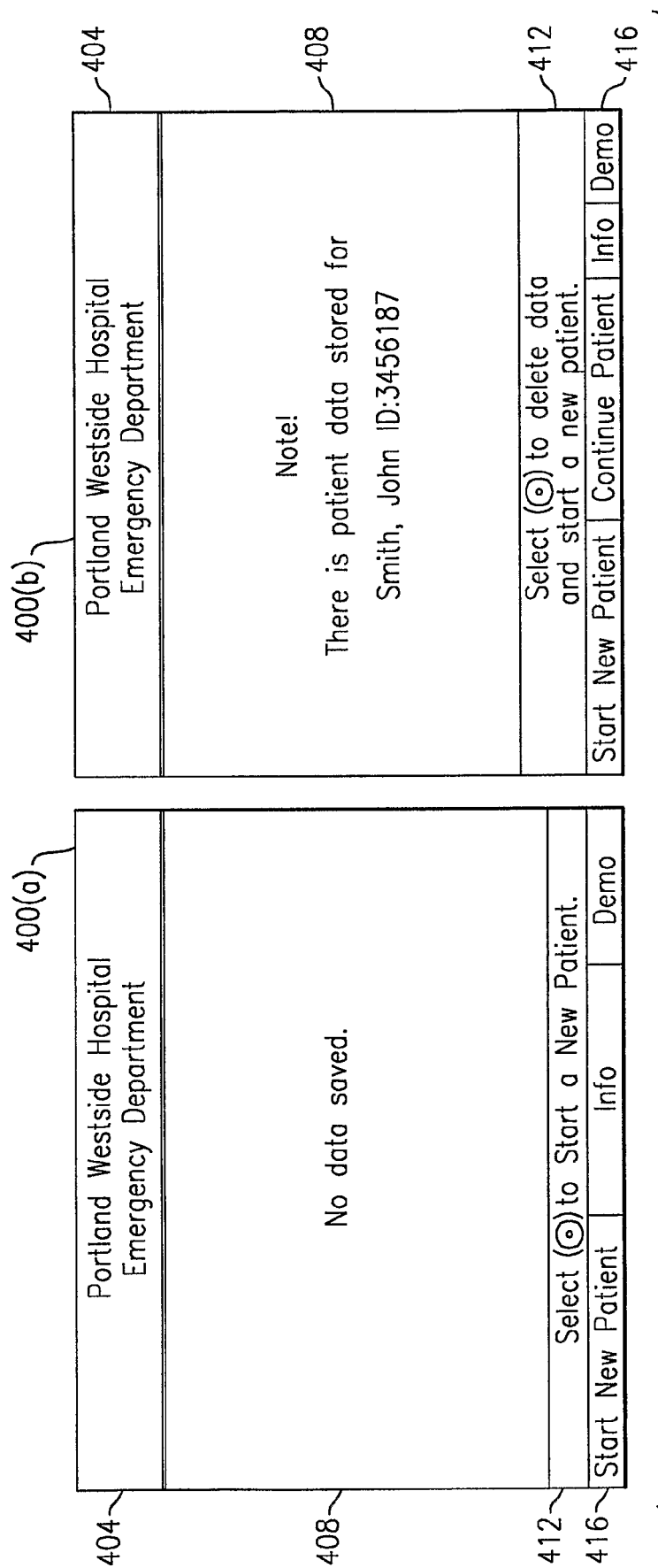
FIG. 24 depicts side by side examples of display screens presented to a user of the vital signs monitoring device upon powering up of the device, depending upon whether patient-related data and settings have been previously stored by the device.

Referring to FIG. 24, the stored template format of each of the generated start-up screens 400(a), 400(b) is similar whether or not patient data has previously been stored by the monitoring device 20. That is, each start-up display screen 400(a), 400(b) commonly includes a customer ID panel 404, a notice panel 408, a bottom message panel 412 and a context menu panel 416, respectively, as read from the top of the display screen. In the instance that no patient data has previously been saved by the monitoring device 20, the notice panel 408 of start-up display screen 400(a) indicates by way of a textual message that no data has been saved. The notice panel 408 of the other version of the display screen 400(b), on the other hand, indicates that specific patient data has been previously stored by the monitoring device 20. In the instance that a patient's data was stored prior to the time the monitoring device 20 was last turned off, monitoring can be resumed for that patient when the monitoring device 20 is powered up again. When the patient data is saved by the monitoring device 20, the settings of the monitoring device 20 are also saved into the nonvolatile memory of the CPU 174. In this instance, a decision must be made by the user as to whether the data is to be saved and monitoring will continue with the same patient or whether the stored patient data should be deleted and a new patient monitoring mode should be initiated.

The customer ID panel 404 provides information about the facility and device that have been previously entered and stored in an information screen, such as shown in FIG. 26, shown as 420(a), 420(b). The information screen 420(a), 420(b) can be accessed from the Info option of the context menu panel 416. Each of the information screens 420(a), 420(b) also include a context menu panel 416 at the bottom thereof, including the same options as the start-up screens 400(a), 400(b), respectively. Typically, this information can be added to the memory of the device 20, such as during the creation and downloading of the configuration file using PC 192, FIG. 6, as described previously.

Figure 25:
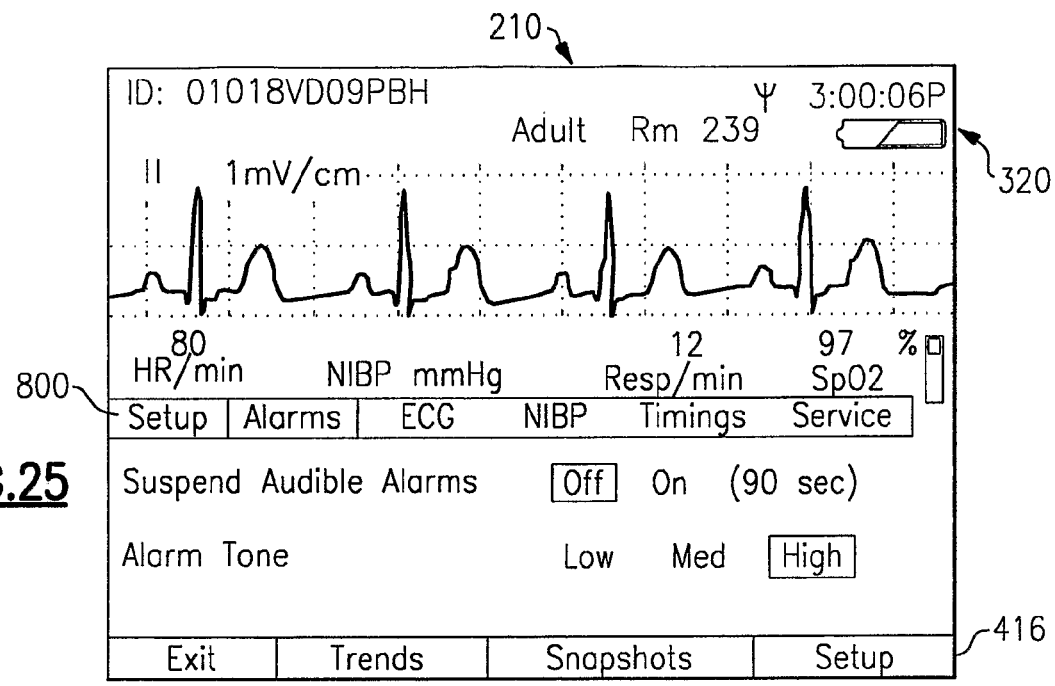
FIG. 25 is an exemplary set-up menu for the vital signs monitoring device.

In general, the context menu panels 416 provide a means for navigation between various control screens of the herein-described monitoring device 20. Each context menu contains a number of menu options disposed along the length of the panel 416. The user interface 92 and in particular, the directional buttons 100 and the SELECT button 96 are used to highlight and select a highlighted option by movement of the display cursor. To that end, selection of one of the context menu options executes a new mode of the monitoring device 20 or creates a new display screen, as described in greater detail below. The content and options available in context menus vary depending on the display screen which utilizes them. Examples of various context menus 416 that are used in the operation of the monitoring device 20 are provided in FIGS. 25, 28 and 47, each of which are detailed in a later portion of this description.

Referring back to FIG. 24, and to the specifics of the context menu panel 416 of the start-up display screens—in the instance in which no previous patient data has been stored by the monitoring device 20, the context menu panel 416 indicates the following available user-selectable options; namely, a Start New Patient option, an Info option, and a Demo option. The Start New Patient option permits the user to enter a patient monitoring mode. The Info option reverts the user to an information screen, such as either 420(a), 420(b) shown in FIG. 26, while selection of the Demo menu option provides access to a demonstration mode for the monitoring device 20.

In the instance that patient data has been saved by the monitoring device 20, the above three (3) user-selectable options are provided in the context menu panel 416 of display screen 400(b), as well as a Continue Patient option. To resume monitoring on the same patient and upon powering up the monitoring device 20, the "patient data stored" display screen, 400(b), FIG. 24, is displayed. The user then verifies that the displayed name and patient ID match that of the current patient and upon verification, and highlights the Continue Patient option in the context menu panel 416 at the bottom of the display screen 400(b). If the latter option is selected through use of the directional arrow buttons 100 and pressing the SELECT button 96, then any stored data is loaded and the monitoring device 20 is ready for monitoring, including the continued implementation of any previous custom configuration settings that are particular to the patient.

If, however, the Start New Patient option (onto which the display cursor is highlighted in the display screen 400(b)) is elected and the SELECT button 96 is pressed, then all previous data (and custom configuration settings) are deleted and a new patient monitoring mode is initiated.

Figure 27:
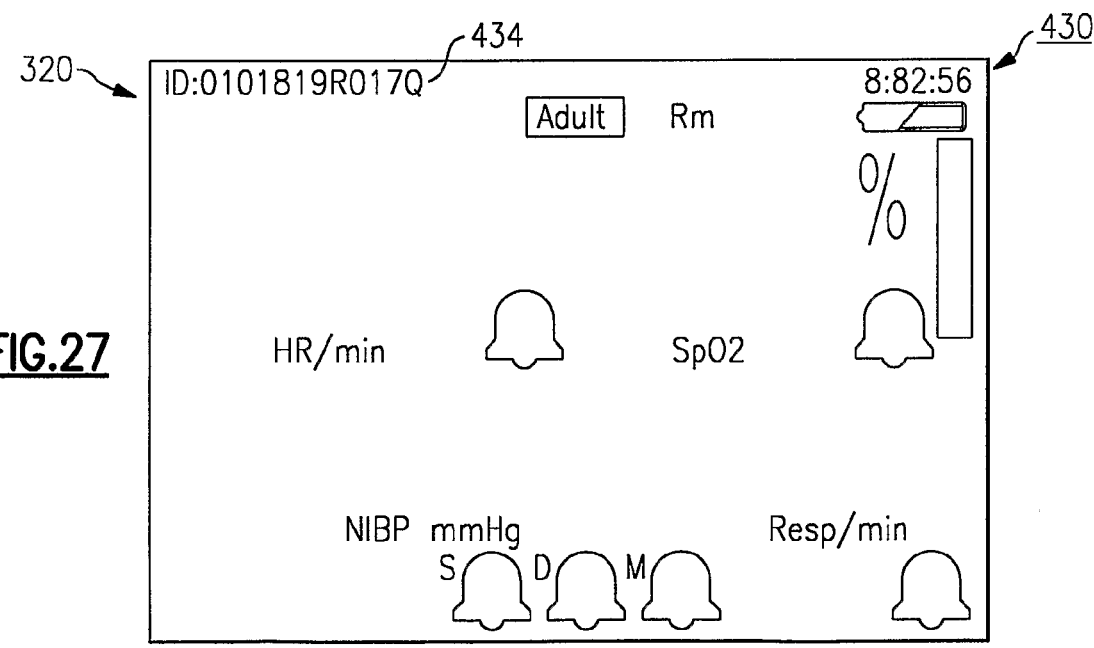
FIG. 27 is a configured data display screen of the vital signs monitoring device in which patient information is being entered.
Figure 28:
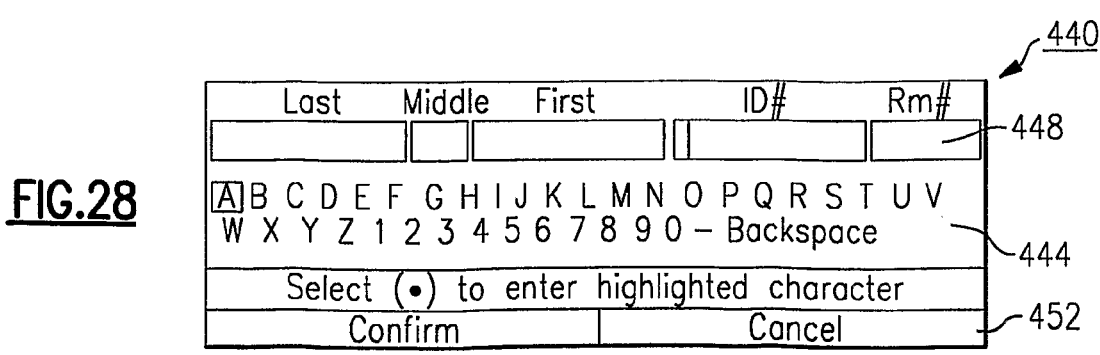
FIG. 28 is another display screen depicting a patient information entry panel of the display screen of FIG. 27.

Upon election of the Start New Patient option, a first configured data display screen 430 appears, as shown in FIG. 27. In this data display screen 430, a unique auto ID is provided in a status panel 320, and more specifically in a device ID field 434 that is highlighted using the SELECT button 96, accessing a Patient Information Entry screen 440, as shown in FIG. 28, the latter consisting of a table of alphanumeric characters 444 that can be highlighted and sequentially entered into the proper field 448 to create entries. The name of the new patient is then entered as well as the patient ID and the patient room number. Alternatively, this data can be entered using the remote monitoring station 184, FIG. 6, through an enabled wireless connection as opposed to the above-described local entry of information. When all of the above information is entered, a Confirm option provided in the context menu panel 416 of the display screen 440 is highlighted and the SELECT button 96 is pressed. All information entered is then stored into memory of the CPU 174 and is used by the device in various display screens throughout the operation of the monitoring device 20. The mode of the patient is then confirmed and the sensor assemblies 28, 32, 36 are attached to the patient and the monitoring device 20 (if not already attached to the device). The monitoring device 20 is now ready to begin monitoring wherein readings are displayed on a formatted default data display screen, such as shown in FIG. 27, in predetermined fields on a display screen adjacent to text identifiers that are preformatted on the generated screen template. The screen format shown in FIG. 27 is that of a large numerics display screen, discussed in greater detail below.

For purposes of the following discussion, it is assumed that each of the sensor assemblies 28, 32, 36 have been suitably attached to a patient (not shown) and the monitoring device 20 and that the patient has been monitored for an extended period of time by the device. A number of specifically configured display screen template formats are stored in memory of the CPU 174 and are available for viewing at the user's option, these templates including associated vital signs data in the form of either current or trended data. An exemplary default display screen 210, FIG. 15, for purposes of this discussion is enabled by way of the configuration settings of the monitoring device 20, this screen being the current display screen displayed to the user during monitoring. The format of this particular display screen 210 includes a status panel 320, a large waveform panel 324 and a parameter panel 328, respectively, as read from the top of the display screen.

Figure 15:
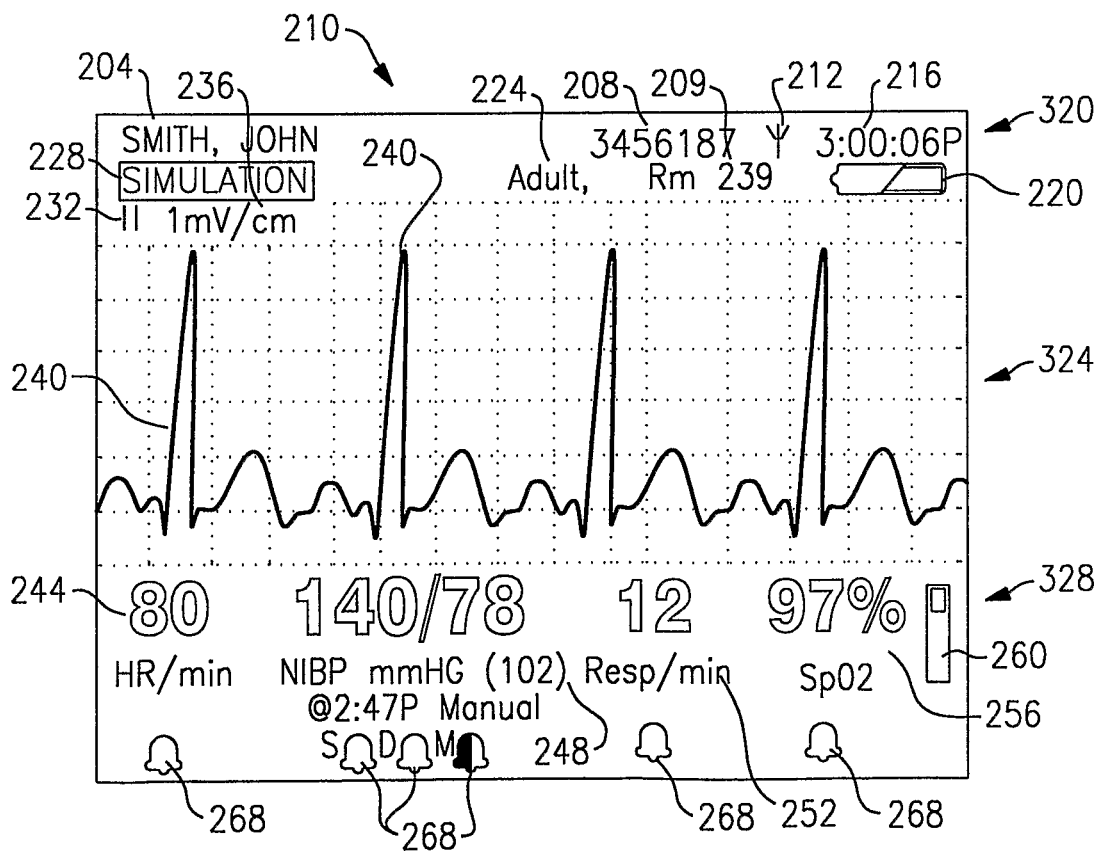
FIG. 15 illustrates an example of a display screen of the vital signs monitoring device of FIGS. 1-3 according to one display mode.

The displayed data that is shown in FIG. 15 as contained in the various fields of the status panel 320 includes the following elements: the patient's name, if available, shown as 204, the patient ID 208, and the patient room number 209. Each of the preceding elements were manually added to the internal memory of the monitoring device 20 and added at start-up as previously described above with regard to FIGS. 27 and 28 by the clinician or alternatively in the case of a network-enabled monitoring device 20, by the remote monitoring station 184, FIG. 6, prior to monitoring of the patient over a wireless communications link. In the former instance, this information as entered in the Patient Entry Information display screen 440, FIG. 28, by the CPU 174 is used to populate the status panel 320 of each display screen of the herein described monitoring device 20 for the patient currently being monitored, for so long as power is maintained to the device, unless the user elects to specifically maintain these settings prior to turning the device off, as described in greater detail below.

Referring to FIG. 15 and in addition to the patient information, the status panel 320 further includes a communication status icon 212 (if the device includes a wireless transceiver 180, FIG. 6, and antenna 182, FIG. 6) and a time display 216, as well as a battery status indicator or icon 220, the latter providing an indication of available battery power. The battery status icon 220 can provide an indication as to whether the contained battery pack 170 is full, partially full indicating that the battery is not fully charged, but not fully discharged, partially full and charging, low battery wherein the battery has approximately 30 minutes of runtime remaining, low battery and charging, very low battery wherein the battery has approximately 5 minutes of run time remaining and very low battery but charging. In the instances in which low battery is indicated by the icon 220 (as indicated by a depiction of a half-filled battery) and in addition to the icon, an alert (not shown) can be provided by the monitoring device 20. The battery status icon 220 would remain after acknowledgement of the alert. Alerts and their management are discussed in a later portion of this description.

According to this embodiment, the CPU 174 is programmed to automatically disable the NIBP sensor assembly 36 upon a low battery indication being determined wherein a status message is displayed to the user if the manual NIBP start/stop button 112 is pressed. If the monitoring device 20 is charging in the charging cradle 140 and a low battery and charging indication appears via icon 220, then the NIBP sensor assembly 36 is enabled.

In addition to the above, the mode (adult, neonatal, pediatric) of the patient 224, as well as the mode of the device 228 (simulation, monitoring) are each applied within separate fields that are provided in the status panel 320 of the display screen 210. Each of the foregoing are typically based upon default settings of the herein described monitoring device 20, unless modified by the user, as described in greater detail below.

With regard to the waveform panel 324, the depicted waveform 240 is current and can originate from a number of sources. The panel 324 further provides text identifiers relating to the specific waveform source 232 and waveform size (display scale) 236. In this example, a waveform representative of an ECG vector is represented. The waveform depicted, including its size and source as displayed, are also typically based upon a default setting of the monitoring device 20, wherein each setting may be changed locally by the user or remotely by the remote monitoring station 184, as described below.

Beneath the waveform panel 324 and in the formatted parameter numerics panel 328, current or live parameter numeric values are displayed for heart rate/pulse rate 244, respiration rate 252, and pulse oximetry 256, as well as a separate dynamic indicator for the pulse amplitude of the pulse oximeter sensor in the form of a blip bar 260. Text identifiers are also provided beneath each above-noted parameter. In addition, the most recent NIBP measurement 248 is also displayed, with a corresponding text identifier and time stamp, the pressure measurement being displayed in terms of systolic over diastolic numerics with mean pressure being expressed in parenthetical terms. Since each of these physiologic parameters, except NIBP, are continuously monitored, their numeric values will change and be updated with stored data being trended by the CPU 174, FIG. 6. Finally, a series of alarm status indicators 268 are also represented in the parameter numerics panel 328 at the bottom of the display screen 210 for each listed parameter. These alarm indicators 268, represented herein by bell icons indicate whether the upper and lower limits for each physiologic parameter are on, the upper alarm limit is on but the lower alarm limit is off, the upper limit is off but the lower limit is on, or all alarms are off through an appropriate representation of an alarm symbol, whether in blank or solid, and combinations thereof. Alarms are described in greater detail in a later portion of this description.

Figure 16:
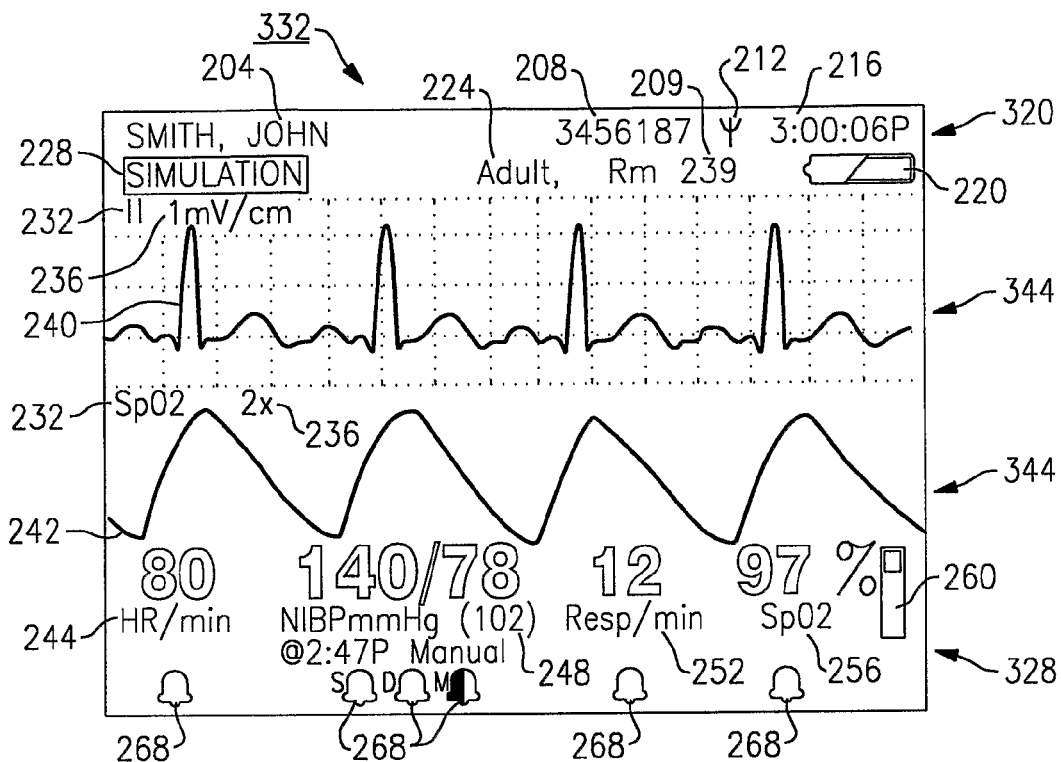
FIG. 16 depicts another example of a display screen of the vital signs monitoring device according to another display mode for the vital signs monitoring device of FIGS. 1-3.
Figure 17:
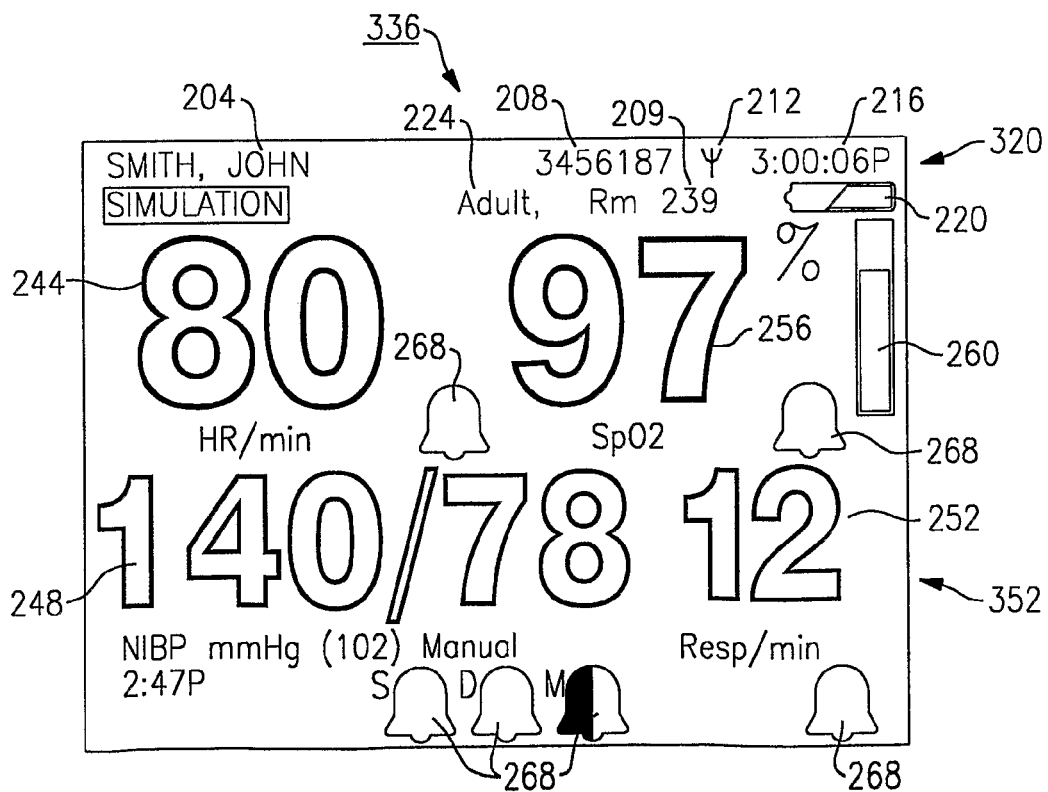
FIG. 17 depicts yet another exemplary display screen according to yet another display mode for the vital signs monitoring device of FIGS. 1-3.
Figure 18:
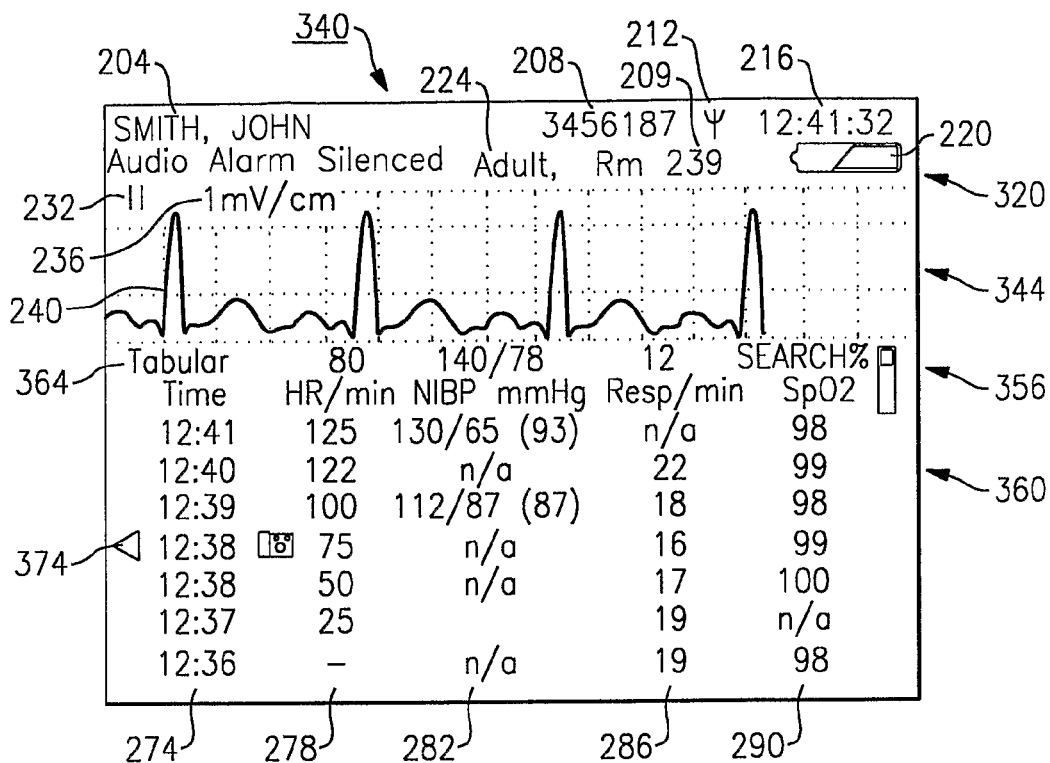
FIG. 18 depicts yet another example of a display screen according to yet another display mode for the vital signs monitoring device of FIGS. 1-3 showing trended tabular data.

Each of FIGS. 16-19 depict additional exemplary display screens that can be selectively displayed by the user in addition to the single waveform display screen 210 depicted in FIG. 15. Each of these additional display screens include a specifically defined template format that is stored into memory for generation by the CPU 174 onto the display 88. According to this specific embodiment, these additional user-selectable display screens include a dual waveform display screen 332, shown in FIG. 16, a large numeric display screen 336, shown in FIG. 17, which is similar to that shown also in FIG. 27, and a single waveform with tabular trended data display screen 340, as shown in FIG. 18. For purposes of discussion herein, each of the same reference numerals are used to label similar data and symbology herein for the sake of convenience and clarity. The above-noted display screens permit live monitoring of vital sign numerics, waveforms and/or trend information in various user-selectable formats as now described.

The dual waveforms display 332 screen of FIG. 16 is a variation upon the single waveform display screen 210 of FIG. 15. This display screen 332 provides patient and monitoring device information as well as two waveforms and available parameter numerics. To that end, the defined format of this display screen 332 includes a status panel 320 that includes each of the elements of the single waveform display screen 210 referred to above including patient name 204, patient ID 208, patient room number 209, communication status indicator 212, time display 216, battery status indicator 220, patient mode indicator 224, and display mode indicator 228. Two small waveform panels 344 are provided in lieu of the single panel of the display screen 210, FIG. 15, the display screen further including a live or current parameters numerics panel 328, similar to that of the single waveform display screen 210, FIG. 15. Each of the waveform panels 344 are smaller than that of the single waveform data display screen 210, but contain similar information including waveform source 232 and size indicia 236. The waveforms presented in the panels 344 can be from two different sources or can be provided alternatively as a cascaded waveform from one source that is presented on two adjacent waveform panels. In the example shown in FIG. 16, separate ECG and SpO$_2$ waveform 240, 242, respectively, are depicted. The live parameter numerics panel 328 like the preceding includes a heart rate/pulse rate numeric and text identifier 244, the most recently taken NIBP numeric 248 including the systolic/diastolic and mean (parentheses) numerics and text identifiers as well as a corresponding time stamp, a respiration numeric and text identifier 252, and an SpO$_2$ numeric and text identifier 256 including a dynamic blip bar 260 showing pulse amplitude. Alarm icons 268, in the forms of bell icons, are also provided for each of the preceding parameters in this panel 328.

The large numerics display screen 336 shown in FIG. 17 is similar to that depicted in FIG. 27, labeled as 430 (but without data or patient information entered). This display screen 336 is defined by a format that includes a status panel 320, also similar to that described for the display screens of FIGS. 15 and 16, and a large numerics panel 352 provided in lieu of waveform panels. The large numerics panel 352 contains the same information provided in the panel 348 discussed with regard to FIG. 16 other than that the icons and associated text identifiers are significantly larger and disposed in differently assigned fields in the display screen 336. More specifically, the live or current parameters panel for this display screen includes a large HR/PR numeric element 244 as well as a text element and an alarm icon 268, a large SpO$_2$ numeric element 256 along with an associated text element, alarm icon 268 and blip bar 260, a large NIBP numeric element 248 representative of the most recent measurement as well as a text element and time stamp of measurement and alarm icon 268 and a large respiration numeric element 252 along with an associated text element and alarm icon 268. With regard to the alarm icons 268, these provide an indication of those alarms that are currently enabled and those alarms that are currently disabled. For purposes of this discussion, the left half of each alarm icon 268 relates to the lower alarm limit and the right hand side of the icon refers to the upper alarm limit. A solid bell, shown herein as white, indicates that the alarm is enabled while a blackened portion of the bell indicates that the alarm is disabled. Alarms are provided (upper and lower limits) for each of heart rate/pulse rate, respiration, NIBP (systolic, diastolic and mean) and SpO$_2$. As seen in the depicted example, the lower limit of the mean NIBP is currently disabled while the remaining alarm limits are each currently enabled. The alarm icons 268 further permit the user to access menus, as described in greater detail below, by which the alarms can be enabled or disabled, upper and lower limits can be set, and volume controls for audible tones can be adjusted.

The herein described monitoring device 20 can not only display current or recent numerics and waveforms, but is also storing data for trend analysis. To that end, several display formats relate to trended data, wherein this data can be reproduced either graphically or tabularly. Snapshot data is also stored in addition to any periodic or randomly taken measurement data and data stored by the device 20 based upon continuous monitoring. To that end, FIG. 18 illustrates a combination waveform/tabular trend display screen 340. In this example, a waveform as well as live parameter numerics and tabular list of trend data are depicted in a generated template format on the display 88 pertaining to a monitored patient. The pre-defined format of this display screen 340 includes a status panel 320, similar to that described with regard to FIG. 15, a single waveform panel 344 including a waveform and text identifiers relating to the waveform source 232 and size 236, respectively, similar to those described in FIG. 16, a trends live numeric panel 356 and a trends data panel 360, respectively.

The trends live numerics panel 356 includes a data display header 364 relating the form of data presented (tabular, graphical, or other) followed by a linear set of current heart rate, respiration and SpO$_2$ parameter numerics and the most recent NIBP measurement, as well as text identifiers beneath each corresponding parameter numeric and the current blip bar 260 for SpO$_2$. A "Time" table heading is also provided beneath the data display header 364.

The trends data panel 360 of this display screen 340 includes a tabular (in this instance) arrangement of stored numerics arranged in a table, allowing the user to navigate through a predetermined period (e.g., 24 hours) of stored trends with entries for time, heart rate/pulse rate, NIBP, respiration and pulse oximetry provided beneath each corresponding text identifier. According to this embodiment, trend data is listed in one minute intervals for each of time, heart rate/pulse rate, respiration, and $SpO_2$, respectively, when any NIBP readings are successfully made using the NIBP start/stop button 112 or through automated mode, or when an $SpO_2$ spot check reading is made. Each of the latter features are described in a later portion herein. As will also be detailed in a later portion of this description, the time interval between trend entries is a configuration setting of the monitoring device 20 that can be selectively adjusted by the user, for example, depending on the patient.

The exemplary display screen 340 is configured to list seven (7) entries in the display panel 360 according to the present example, although this parameter can be varied. For example, and as shown in FIGS. 19 and 54-56, a twelve (12) entry table is provided on a tabular trend data display screen 470. No waveform data is provided on this screen 470, which is defined by a status panel 320, a trends live numerics panel 356, similar to that shown in FIG. 18, and a trends data panel 474. As noted, up to 24 hours or other predetermined time period of trend data can be stored into memory. A scrolling navigation icon 374 is also provided next to the time listing in order to permit the user to access any of the stored data, as needed.

Figures 56, 57:
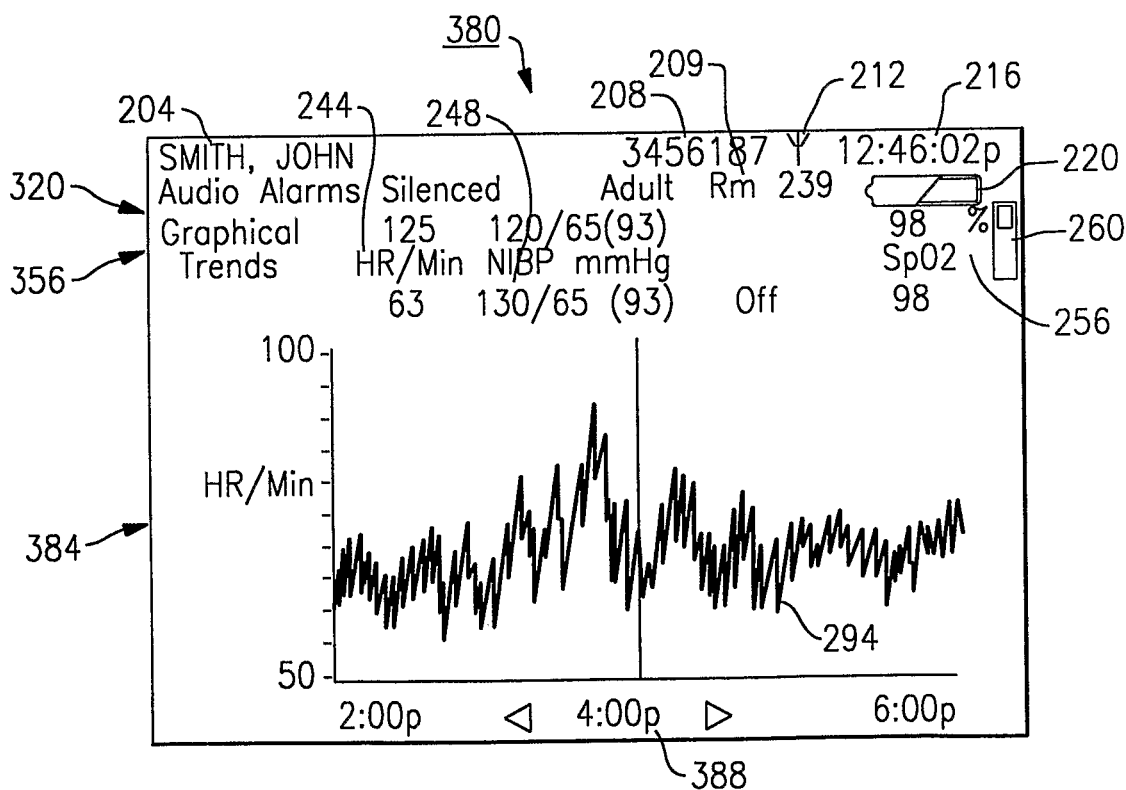

In addition to tabular data, the herein described device 20 can display trended data in a graphical form. An exemplary graphical trend data display screen 380 is shown in FIG. 57. This display screen 380 is defined by a format that includes a status panel 320, as described above, a live trends numerics panel 356, and a graphics display panel 384 with graphical trend data 294 having a time scroll 388 at the bottom thereof. The data shown pertains to a single parameter (in this example, heart rate), wherein the parameter data being displayed can be varied, as described in greater detail below.

Figure 19:
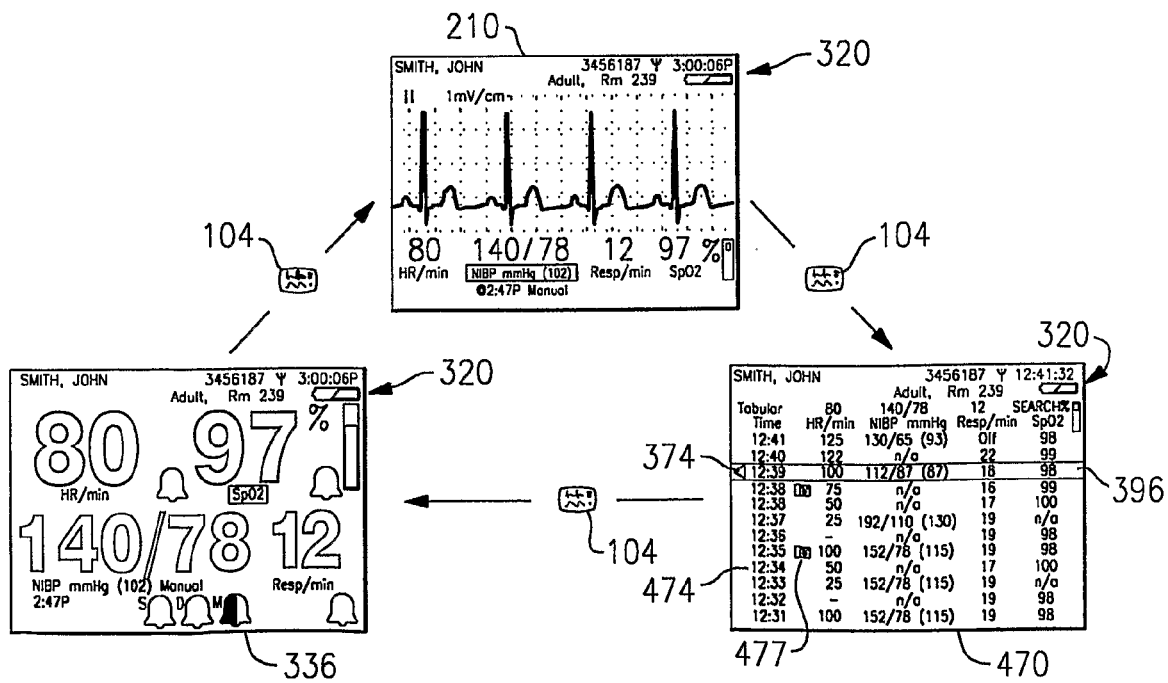
FIG. 19 depicts the toggling between various display modes using the vital signs monitoring device.
Figure 50:
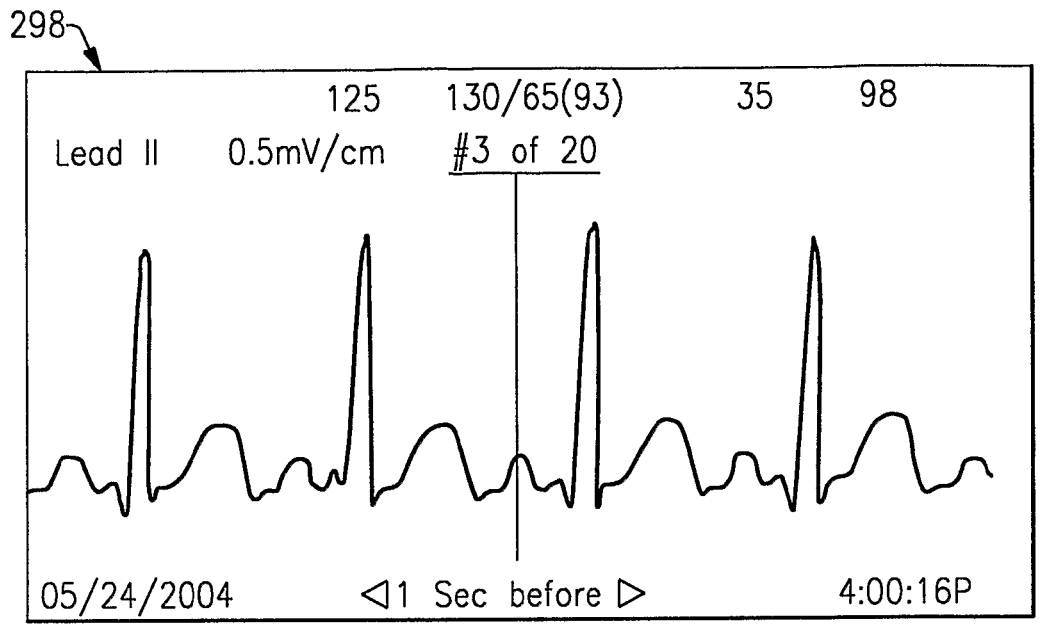
FIGS. 50-52 depict examples of an exemplary display screen according to yet another display mode for the vital signs monitoring device of FIGS. 1-3 illustrating snapshots of vitals signs data captured by the device.

Referring to FIGS. 18, 19 and 56, user-captured snapshots are identified separately in the tabular listing of trend data with a camera icon 477. A sample snapshots viewing screen 298 is shown in FIG. 50. Reviewing of snapshot data is discussed in a later portion of this description.

The display button 104 according to the herein described embodiment is used to cycle through the configured display formats. As shown in FIG. 19, the display modes can be toggled between large numeric display screens, waveform/numeric display screens, and trend data display screens. According to this example, pressing the display button 104 allows the user of the monitoring device 20 to toggle between a large numerics display screen 336, a single waveform display screen 210, and a tabular trend display screen 470, respectively. Depending on the configuration settings of the herein described monitoring device 20, the display button 104 could be used to navigate between each of the display screens shown in FIGS. 15, 17 and 18, respectively, wherein a default version of each type of display screen can be determined.

Figure 21:
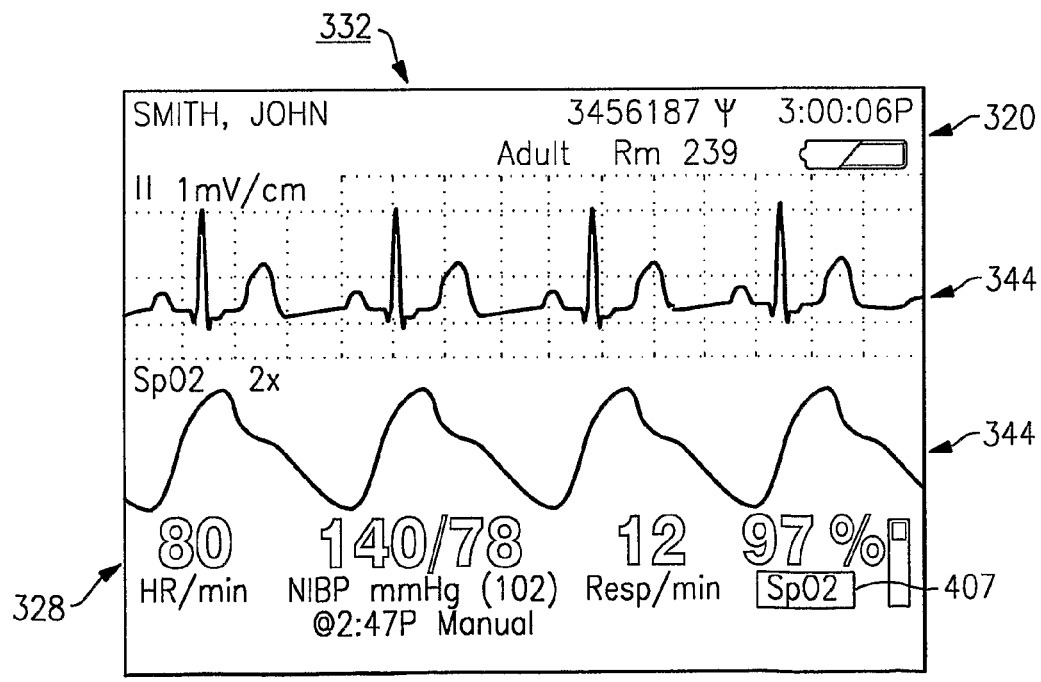
FIG. 21 illustrates another example of a display screen of the vital signs monitoring device of the present invention and illustrating how the SELECT button is used to select a highlighted item for navigation.

In terms of overall navigation with regard to any of the above primary display screens and in general according to this embodiment, the display cursor, as referred to above, is always highlighted. Referring to FIG. 21, and looking at an exemplary display screen, in this case a dual waveform display screen 332, each and every display screen according to this embodiment includes a single element—the current context—labeled herein as 407, that is shown by a first colored field (e.g., blue) in order to highlight the element.

Using the user interface 92 of the herein described monitoring device 20, pressing the SELECT button 96 causes the monitoring device 20 to replace the current display screen with another display screen that is related to the current context. By way of example, if the $SpO_2$ text identifier is highlighted in the display screen 332 of FIG. 21, and the SELECT button 96 is pressed, the monitoring device 20 is programmed to then display a $SpO_2$ control menu 402, having a specified format and shown in FIG. 22, onto the primary display screen. The directional buttons 100 can be used to scroll the display cursor in order to highlight the item to be selected by the user.

In addition, there are at least some display screens that also contain elements—parameter values—that are highlighted by a second colored field (e.g., green). In the case of the second color highlighted areas, the current values of multiple parameters are identified within a given context. For example and in the control menu display screen of FIG. 22, the current context of the $SpO_2$ monitoring menu option 403 is highlighted in the primary or first color (e.g., blue), while the current settings 404 of the $SpO_2$ parameters according to this embodiment are highlighted in the second color (e.g., green). Control menus and other menus are discussed in a later portion of this description.

In passing, other forms of indications can be provided on a display screen to a user using various colors or are provided with separate indicators in accordance with this embodiment. For example, items listed in red as shown in the display screen of FIG. 20 indicate readings 396 that exceeded a given alarm limit (either an upper or a lower limit) in addition to the current context 392, for example. Other examples are provided. For example, the trend tabular display screen 470 presented in FIG. 56 depicts a number of readings 475 that have been compared to known limits and have been suitably identified.

In addition to the display button 104, the herein described monitoring device includes a set of embedded menus that are used for at least two purposes. First, certain menus (e.g., context menus) permit the user to navigate between various modes of the monitoring device 20. Second, other menus permit adjustments to be made to the monitoring device 20. These adjustments are intended to be temporary and typically relate to the specific patient being monitored. As previously noted, device settings are typically configured through factory default settings. A technique using a configuration file using the charging cradle 140 as an intermediary relative to a portable computer 192, FIG. 6, has also been discussed as an option to permit at least some of the factory settings to be overridden. The monitoring device 20 further permits custom configuration at the user level using a variety of display menus that can be accessed through the user interface 92. For purposes of explanation herein, two (2) main types of menus can be accessed, pop-up (also referred to throughout the discussion as drop-down) menus and control menus. Each of these menus will now be described with regard to the present embodiment. Other menus assist in navigation through and between various display screens in addition to the herein described display button 112. These menus have been alluded to with regard to the start-up display screens, FIG. 24, and information screens, FIG. 27, noted above and are referred to as context menus.

First, pop-up or drop down menus are provided to allow a user to temporarily make configuration settings for the herein described monitoring device 20 as well as to vary certain formats, for example, for display. The menus also affect various modes of the device, among other features, as will now be described. In brief, the display cursor is used to highlight an item in any primary display screen 210, 332, such as shown in FIGS. 15, 16, using the directional buttons 100 of the user interface 92 and the SELECT button 96 is pressed to access a corresponding drop-down menu. As shown, for example, in FIG. 53, the resulting pop-up or drop down menu appears as an overlay onto the primary display screen 590 wherein the format of each corresponding menu includes a header text and a plurality of listed menu items or options. According to this embodiment, there are at least ten (10) drop down menus available for the herein described monitoring device 20, each of which enable certain settings of the device to be temporarily altered for a particular patient.

Figure 29:
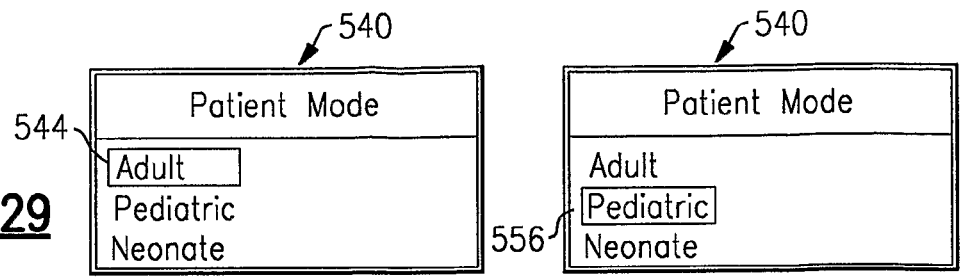
FIG. 29 depicts an exemplary change patient mode menu for the display screen of the vital signs monitoring device of FIGS. 1-3.
Figure 30:
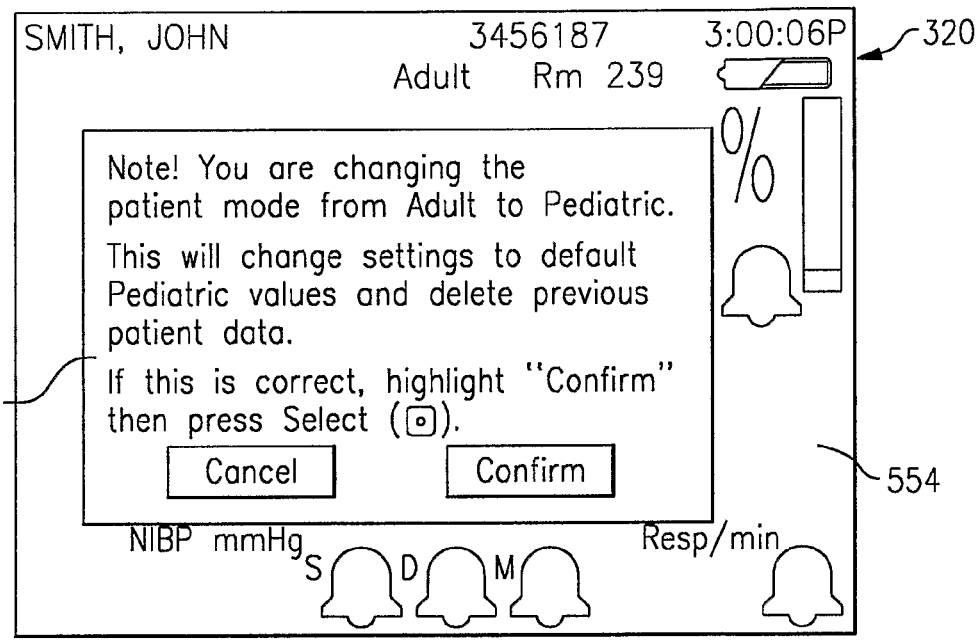
FIG. 30 depicts a confirmation display screen that is displayed by the vital signs monitoring device in accordance with the invention when a patient mode is changed by the user.

A patient mode drop down menu 540, FIG. 29, is accessible by highlighting the displayed patient mode field 224 as provided on any primary vital signs display screen 210, FIG. 15, in the status panel 320 thereof and pressing the SELECT button 96. The current or default patient mode 544, in this case, an Adult mode, is highlighted and the directional arrow buttons 100 of the user interface 92, FIG. 2, enable the mode to be changed to pediatric mode, shown as 556. When a patient mode is changed according to this embodiment, all stored vital signs data, including any snapshot and trended data, for the patient is deleted automatically from the CPU 174 and all monitoring device settings revert to the default settings for the new patient mode that is selected. Therefore and when changing a patient mode, a confirmation screen 550, see FIG. 30, appears as an overlay on the display screen, shown herein as 554, indicating that parameter values will be changed to default settings for the mode now selected and further indicating that all stored information will be lost if the patient mode is changed. Confirmation is then required before any new mode selection can be implemented by the user wherein confirmation changes the patient mode and removes the confirmation message panel 550 from the display screen 554. The resulting display screen (not shown) then indicates pediatric in the patient mode field 224 thereof.

As noted previously and referring to FIG. 6, the monitoring device 20 includes a wireless RF radio card 180 and internal antenna 182 which when enabled, automatically establishes a wireless communications link between the monitoring device 20 and the central monitoring station 184. While within the confines of a wireless LAN (Local Area Network), this connection is suitable within range of a suitable access point 186. The communication status indicator or icon 212 located on the status panel 320 of any primary display screen 210, such as those shown in FIG. 15, is configured to provide an indication of the status of the wireless connection with the remote monitoring station 184, which is limited, for example, given the distance between the monitoring device 20 and an access point 186 on the network. For example, if the status indicator 212 is blank, according to this embodiment, then the monitoring device 20 is not enabled for communication with the remote monitoring station 184. This status indicator 212 can provide certain information concerning the connection as follows according to this embodiment: If the communication status indicator 212 flashes, this is an indication that the monitoring device 20 is associated with an access point 186, but the device is not communicating with the remote monitoring station 184. If the communication status indicator 212 has a line appearing through it, the indicator being presented as shown in FIGS. 15-18 as an antenna symbol, then the monitoring device 20 is not communicating with an access point 186, FIG. 6, and is not communicating with the remote monitoring station 184. As previously noted, the communication status indicator 212 according to this embodiment is located at the upper right hand corner of the status panel 320 in any primary display screen. Similar indications can be made using the status indicator 212 when the monitoring device 20 is communicating with a PC 192 and not with the network, and whether the monitoring device is associated with the network and is communicating with the remote monitoring station 184.

Due to battery constraints it is desirable when the monitoring device 20 moves out of range of the access point 186, that the user can selectively disconnect the monitoring device 20 from the wireless network and place the device in a disconnected wireless mode. This selective disconnection is highly desirable given the considerable drain to the battery resources that occur when attempting to restore communications with the remote monitoring station 184, FIG. 6, as the device would continue to attempt to restore communications even when the device is out of range. According to one version according to the present invention, this selective disconnection is achieved through software wherein the user highlights the communications status indicator 212 of primary display screen 210, FIG. 15, or any display screen having a status panel 320 using one of the directional arrow buttons 100 pressing the SELECT button 96.

Figure 48:
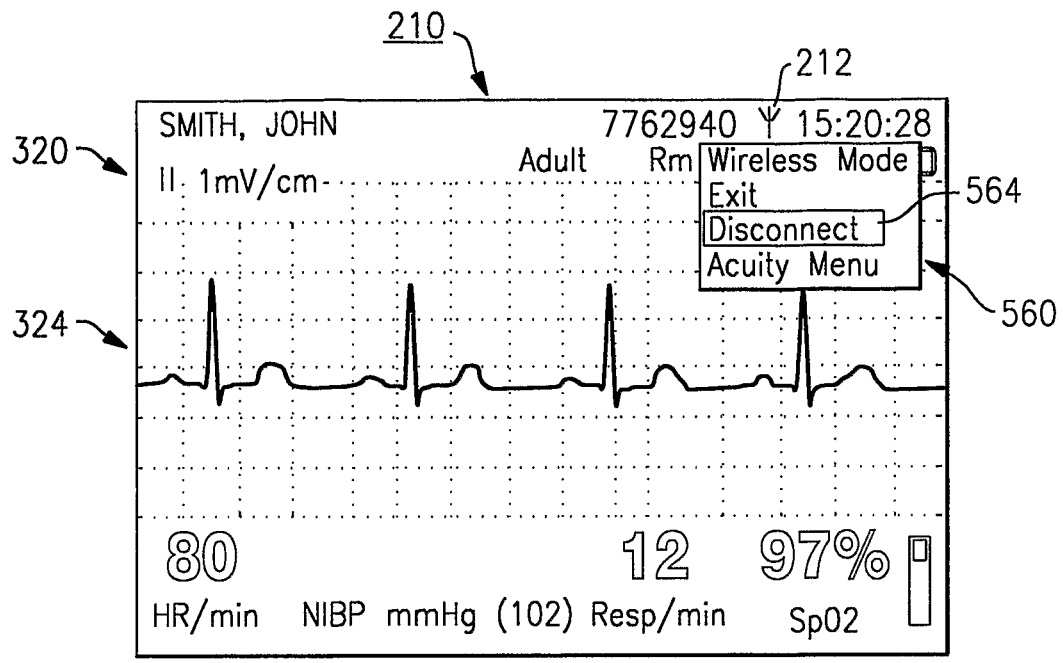
FIG. 48 is an exemplary display screen of the vital signs monitoring device depicting in part, a wireless mode drop-down menu.
Figure 49:
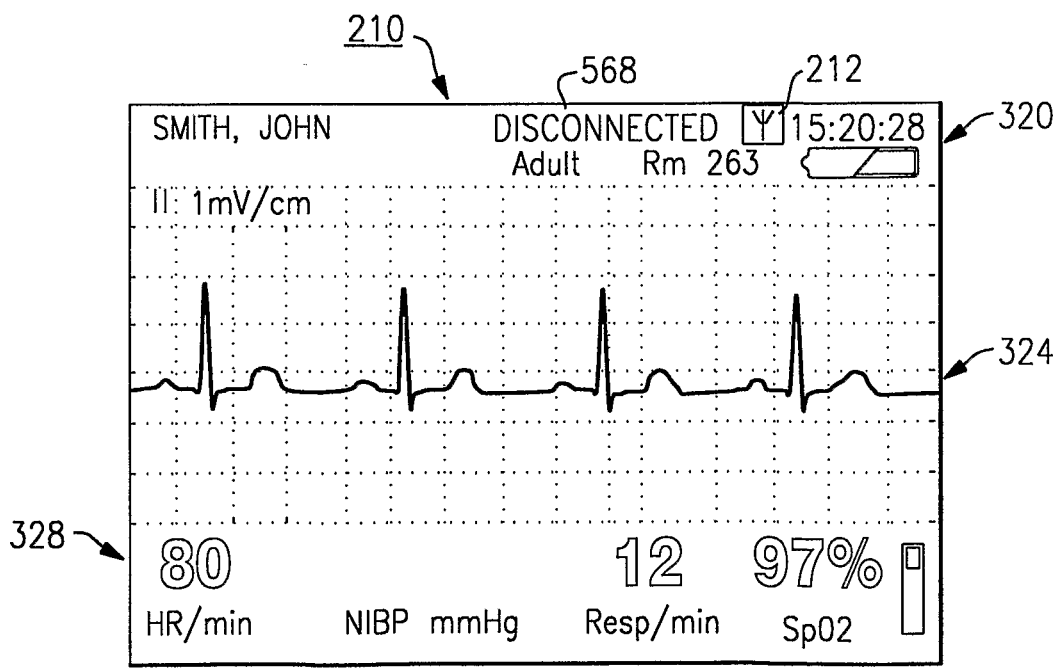
FIG. 49 is a display screen accessed and displayed by the vital signs monitoring device when the device is disconnected from the wireless network.

According to this embodiment and referring to FIGS. 48 and 49, a disconnected wireless icon popup or drop-down menu 560 (if the device is enabled with a wireless transceiver 180 and antenna 182) is accessed by which the user is permitted to selectively toggle into and out of a disconnected wireless mode.

The pop-up menu 560 includes a set of menu options, including a disconnect option 564 which the user can elect to disconnect the monitoring device 20 from the wireless network by scrolling using the appropriate directional arrow buttons 100 and highlighting the disconnect menu option. This election is further indicated to the user by one of the status indicators 169, FIG. 2, provided on the front facing side 84 of the monitoring device 20. During the time that the monitoring device 20 is disconnected from the network, the device provides only local respiration, NIBP, HR/PR and $SpO_2$ alarms or equipment alerts. During that time, a Disconnect message 568 is also displayed to the user next to the communication status indicator 212 on the display screen 210, the latter having a symbol indication of disconnection, as shown in FIG. 49. The use of the disconnect feature provides an advantage in that battery/device power is conserved while the monitoring device 20 is out of range. During the time the above wireless disconnect feature is utilized, trended vital signs data continues to be stored within the memory of the CPU 174, as per normal operation.

When the monitoring device 20 is again within range of the network, the communication status indicator 212, FIG. 15, provides a signal that the monitoring device 20 is within range and network connection can be restored by again highlighting the communication status indicator 212 to access the wireless mode menu 560, highlighting a Reconnect menu option (not shown), and pressing the SELECT button 96. This selection automatically causes a prompt that is displayed to the user for information concerning the patient and the network. A similar message is displayed at the remote monitoring station 184. Reconfiguration and handshaking of the herein described monitoring device 20 with the wireless network is as described in the previously incorporated U.S. Pat. No. 6,544, 174. At the time network connection is restored, all trended data stored during the time the monitoring device 20 was disconnected is transmitted to the remote monitoring station 184, FIG. 6, over the wireless network.

While the wireless version of the herein described monitoring device 20 is connected over the network, patient data gathered by the monitoring device is continuously stored at the remote monitoring station 184. At the remote monitoring station 184, patient information can be accessed and administrative functions can be performed including admitting, transferring and discharging the patient from the remote central monitoring station unit, editing the patient description (name, primary care physician), and reviewing and printing patient data, including trends and waveforms.

Figure 32:
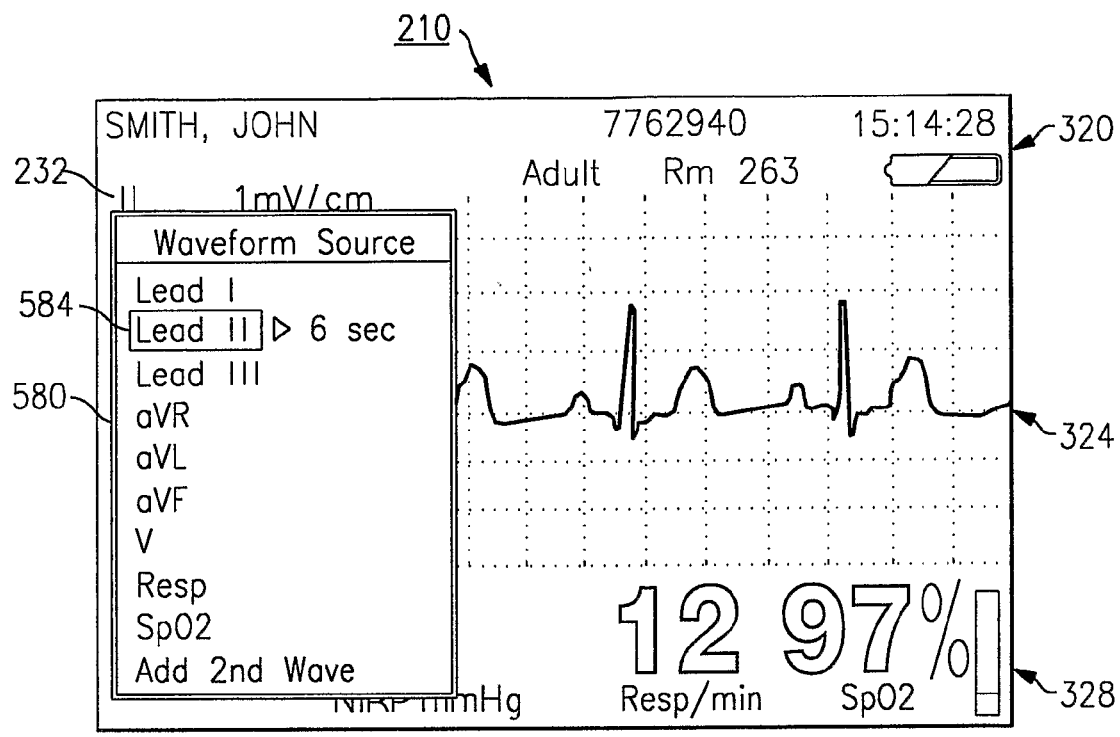
FIG. 32 is an exemplary display screen of the vital signs monitoring device of the present invention including a waveform source menu.
Figure 33:
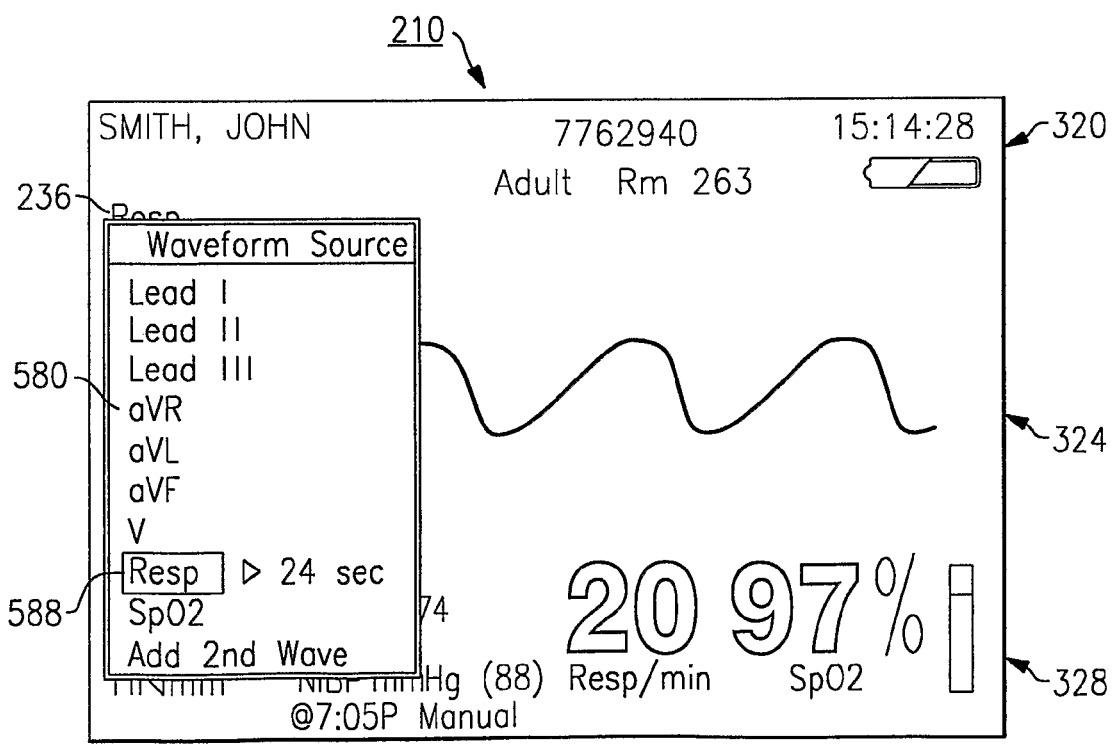
FIG. 33 is another exemplary display screen of the vital signs monitoring device depicting a different waveform source.

Other pop-up or drop-down menus are provided according to this embodiment for temporarily configuring other settings of the monitoring device 20 include a waveform source popup menu 580, see FIGS. 32, 33, that provides user selections for determining which waveform is being displayed (e.g., resp, ECG including choice of vector) and for switching, for example, between a single waveform display screen 210 and a dual waveforms display screen 332, FIG. 16. This latter menu 580 is accessed by the user by highlighting the waveform source field 232 on the display screen 210 and pressing the SELECT button 96. According to the present embodiment and for all waveforms, except respiration, the monitoring device 20 further includes means for cascading a display in order to sweep a single waveform through two panels, thereby showing or presenting a waveform covering a 2× time period (e.g., 6 seconds to 12 seconds). FIG. 32 illustrates an example ECG waveform having a default menu option 584, with FIG. 33 depicting a user option 588 for a respiration waveform using the menu 580.

Figure 34:
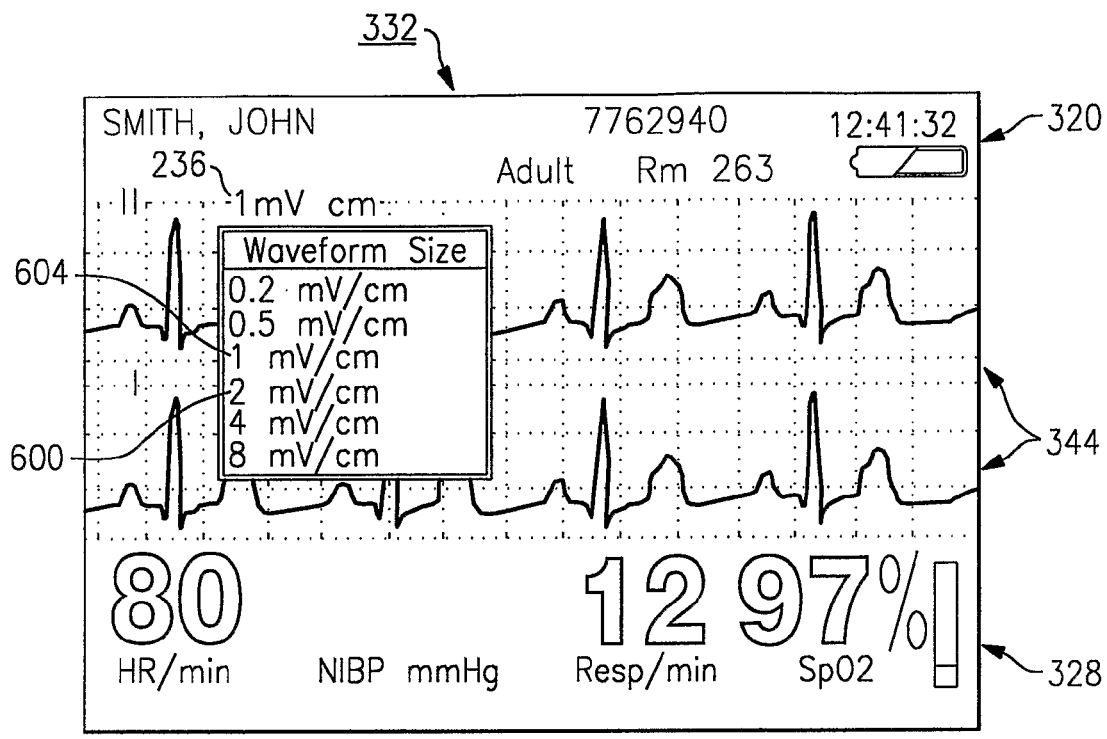
FIG. 34 is another exemplary display screen of the vital signs monitoring device including a waveform size menu.

Similarly, a waveform size drop-down menu 600, FIG. 34, permits user selection relating to the size of displayed ECG, SpO$_2$ or respiration waveforms relative to any display screen 332 by highlighting the waveform size text identifier 236, located in the waveform panel 344 and selecting a menu option 604. A sample respiration waveform 608, FIG. 37, is shown that is augmented by this size menu.

Figure 52:
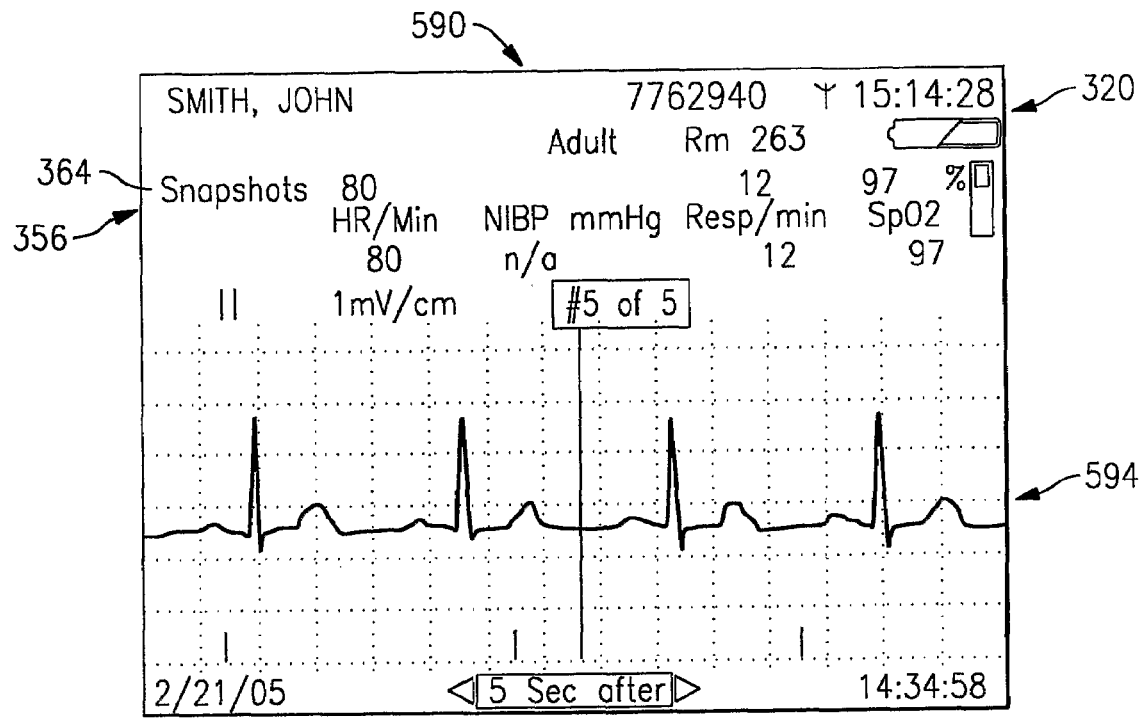
Figure 53:
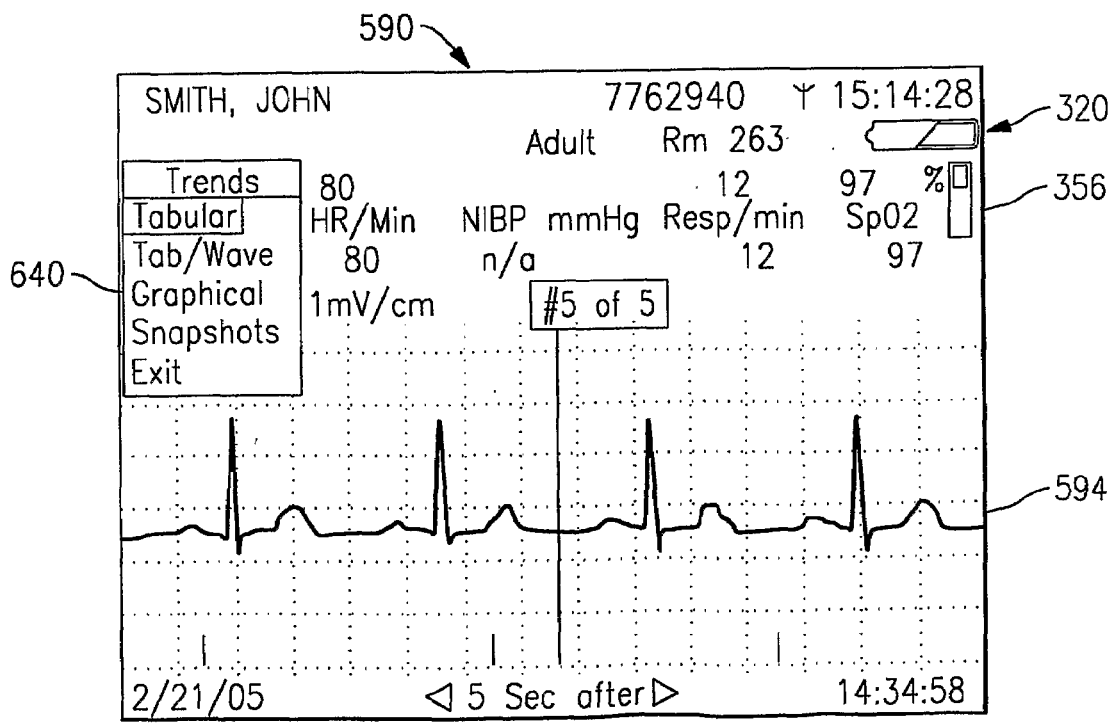
FIG. 53 depicts a snapshot display screen similar to FIGS. 50-52, but further including a trends data selection menu.

A trend display pop-up menu 640, FIG. 53, permits selection between various forms of trended data (tabular, waveform, snapshot) by highlighting the data display header 364, FIG. 52, in the trends live numerics panel 356, FIG. 52, of a trended display screen, in this instance, a snapshots display screen 590. As previously noted, tabular screens are shown in FIGS. 54-56 and a graphical trend display screen 380 is depicted in FIG. 57.

Similarly, a trend view interval popup menu 660, FIG. 55, is accessed by highlighting the Time heading in the data display panel 474, the menu permitting the time intervals between trended data listed to be selectively varied by the user.

Additional pop-up menus according to this embodiment include a snapshot waveform source popup menu, a graphical source pop-up menu and a snapshot selection pop-up menu. Each of these embedded menus are similarly accessed by highlighting the appropriate text identifier and pressing the SELECT button 96 to affect temporary configuration setting changes for the device 20. In addition, an SpO$_2$ spot check or random pop-up menu 620, FIG. 41, is also provided, details being provided for this latter feature in a succeeding section.

A "control" menu for purposes of this embodiment includes a topic name for the current context (for example, SpO$_2$, in FIG. 22), each menu being defined by a stored formatted template comprising a first display panel having a column of parameters with one of the parameters highlighted (for example, SpO$_2$ Monitoring), and a column of options, with one item in the set of options being highlighted (for example, Standby, On, 100, On, 90, Low). The primary (e.g., blue) highlighted item indicates the parameter that is currently enabled for modification, while secondary (e.g., green) highlighted items indicate each of the current settings for all parameters in the control menu. Each control menu further includes a context menu at the bottom of the control panel in order to enable navigation as well as permit confirmation or cancellation of a choice/option selected by the user, such as in the instance of the start-up display screens 400(*a*), 400(*b*), FIG. 24. Presently; the monitoring device 20 described herein includes at least nine (9) control menus that are accessible by the user.

As noted, each control menu can provide customization of the configuration of the monitoring device 20 for the current patient and to confirm choices. As in the preceding, each control menu can be accessed using the directional arrow buttons 100 to locate and highlight the item to be controlled and pressing the SELECT button 96, as previously described. It will be readily apparent that the number and arrangement of these menus is exemplary and that other variations and modifications are possible within the intended ambits of the invention. Additionally, it should further be noted that each of the following controls can be similarly modified from the remote monitoring station 184 over the wireless connection with the monitoring device 20.

Figure 31:
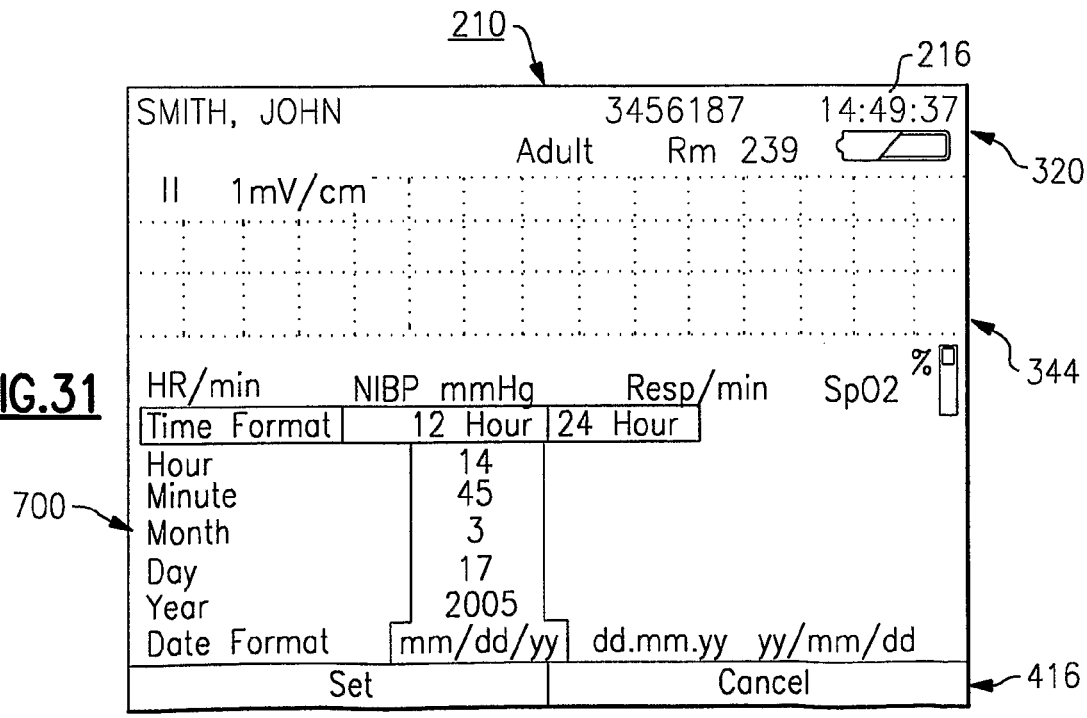
FIG. 31 is an exemplary display screen of the vital signs monitoring device of the present invention including a time/date control menu.

First, a time setup control menu 700, FIG. 31, allows the time, date and time format used by the monitoring device 20 to be locally modified by the user. More particularly and according to this embodiment, the time format (12 hour/24 hour), hour, minute, month, day, year, year and year format can be selectively adjusted by the user. The time and date can also be confirmed for correctness as the monitoring device 20 is capable of displaying time in either 12 hour (AM/PM) or 24 hour format, and displays the date in either a month/day/year, day/month/year, or other suitable format. According to this embodiment, the date does not appear in the primary display screens but does appear in both a snapshot list and associated snapshot data, details of which are described below. Highlighting the time display 216 (located in the upper right corner of a primary vital signs display screen 210 or any display screen having a status panel 320) and pressing the SELECT button 96 to accesses the Time/Date control menu 700, the screen allowing changes to be made and stored into memory by the monitoring device 20.

Additionally, a number of parameter control menus are accessible, including an NIBP control menu, an SpO$_2$ control menu, a HR/PR control menu and a respiration control menu, respectively. Each of these parameter control menus can be accessed by either selecting the parameter text identifier in any primary display screen such as 210, FIG. 15, or by selecting the alarm bell icon 268.

Figure 23:
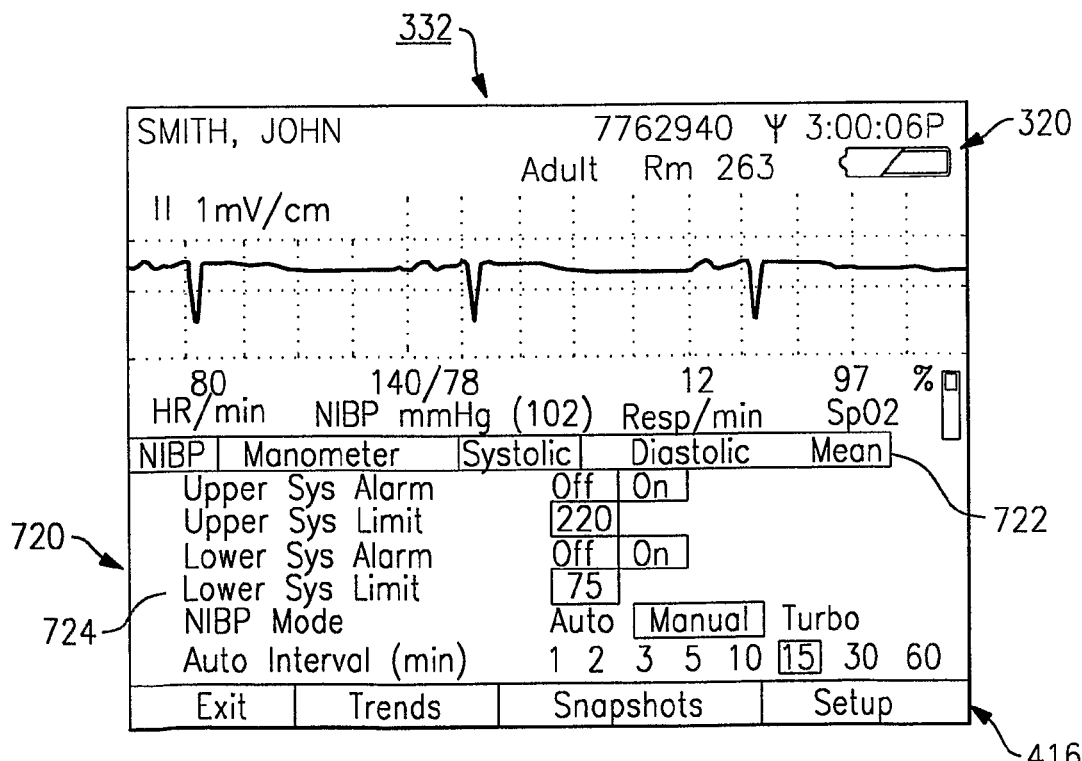
FIG. 23 depicts another exemplary control menu for the vital signs monitoring device in accordance with the present invention.

More specifically, the NIBP control menu permits the setting of upper and lower alarm limits for each of the systolic, diastolic and mean pressures as well as the selection of a digital manometer, the selection of a specific NIBP mode and the time interval used when an automatic mode is enabled. An exemplary NIBP control menu 720 is shown in FIG. 23. The NIBP control menu 720 is defined by three panels according to the present embodiment. The uppermost panel 722 includes a listing of menu options that can be elected by the user. The second field 724 includes a listing of submenu options associated with each menu option from the first panel 722. The third panel is a context menu panel 416 that includes a series of navigational options.

More specifically with regard to the herein described monitoring device 20, NIBP measurements can be taken through a user-selected automatic mode in which blood pressure readings are taken at prescribed time intervals. Following the correct positioning of a proper sized cuff 76, FIG. 1, on a patient, and screwing the hose end into the NIBP air connector fitting 48, FIG. 3, provided on the top facing side 52 of the device housing 24, FIG. 3, the automatic NIBP mode can be enabled by highlighting the NIBP text identifier in the primary vital signs display screen 210, FIG. 15, and pressing the SELECT button 96. The above selection accesses the NIBP control menu 720, shown in FIG. 23, wherein the NIBP Mode option is scrolled to and the Auto menu suboption in the second panel 724 is selected using the directional control buttons 100 to highlight the desired mode and pressing the SELECT button 96. An appropriate time interval can then be selected by highlighting the Auto Time Interval (min) suboption in the panel 724 that will provide automatic blood pressure measurements at the prescribed intervals (e.g., 3 min, 5 min, 15 min, 30 min, 60 min, etc). It should be noted that the incorrect placement or failure to place the cuff 76 on the patient will still enable automated mode, but an equipment alert will be sounded by the monitoring device 20.

The automatic NIBP mode can be disabled by highlighting the NIBP text identifier on the primary vital signs display screen 210 using the directional control buttons 100, pressing the SELECT button 96 to access the NIBP control menu, FIG. 23, and then highlighting NIBP mode from the NIBP control menu 720 and selecting the Manual menu option using the appropriate directional control buttons 100.

Otherwise, any blood pressure reading can be taken manually after positioning the correct cuff 76, FIG. 1, and hose 80, FIG. 1, relative to the patient, screwing the hose end into the NIBP air connector fitting 48, FIG. 3, provided on the top facing side 52, FIG. 3, of the housing 24 and pressing the NIBP start/stop button 112. As previously noted, all manual and other NIBP mode measurements are stored as trended data by the monitoring device 20.

In addition, an enhanced blood pressure measurement mode (herein referred to as "Turbo" mode) is provided in which the monitoring device 20 automatically initiates a blood pressure measurement reading in a conventional manner and then takes as many readings as is possible within a predetermined time period (e.g., 5 minutes), provided this option is enabled by way of default configuration settings such as through the downloaded configuration file. Turbo mode, as defined herein, can be set through the user interface 92 by highlighting the NIBP text identifier in any primary vital signs display screen 210 and pressing the SELECT button 96 to access the NIBP control menu 720, FIG. 23, as previously described. The NIBP Mode menu option can then be highlighted with the Turbo suboption then being selected using the appropriate arrow button 100. Selecting the NIBP start/stop button 112 or highlighting the NIBP Mode Manual menu option from the NIBP control menu 720 will restore the monitoring device 20 to a manual NIBP measurement mode.

Figure 44:
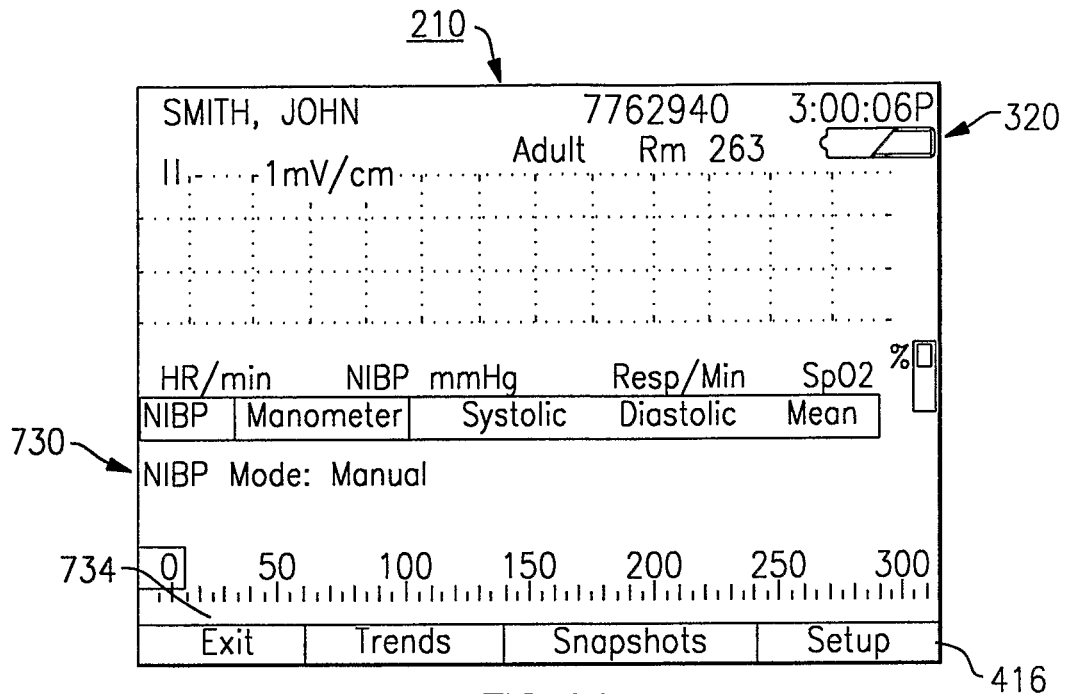
FIG. 44 is an exemplary display screen of the vital signs monitoring device illustrating a digital manometer feature.
Figure 45:
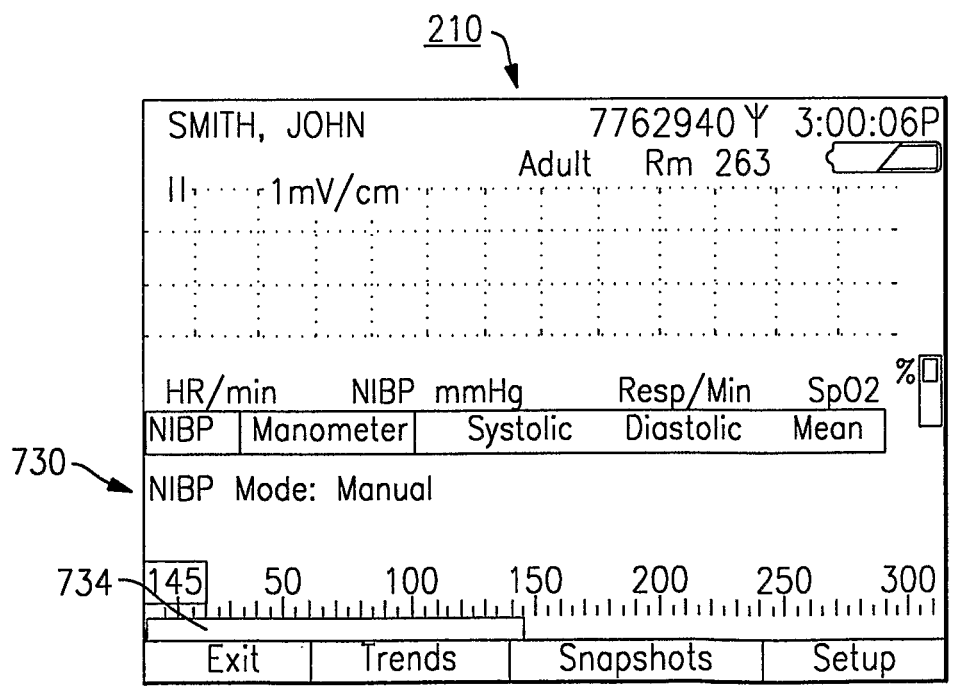
FIG. 45 is the display screen of FIG. 44 at a later time during an NIBP reading, in progress.
Figure 46:
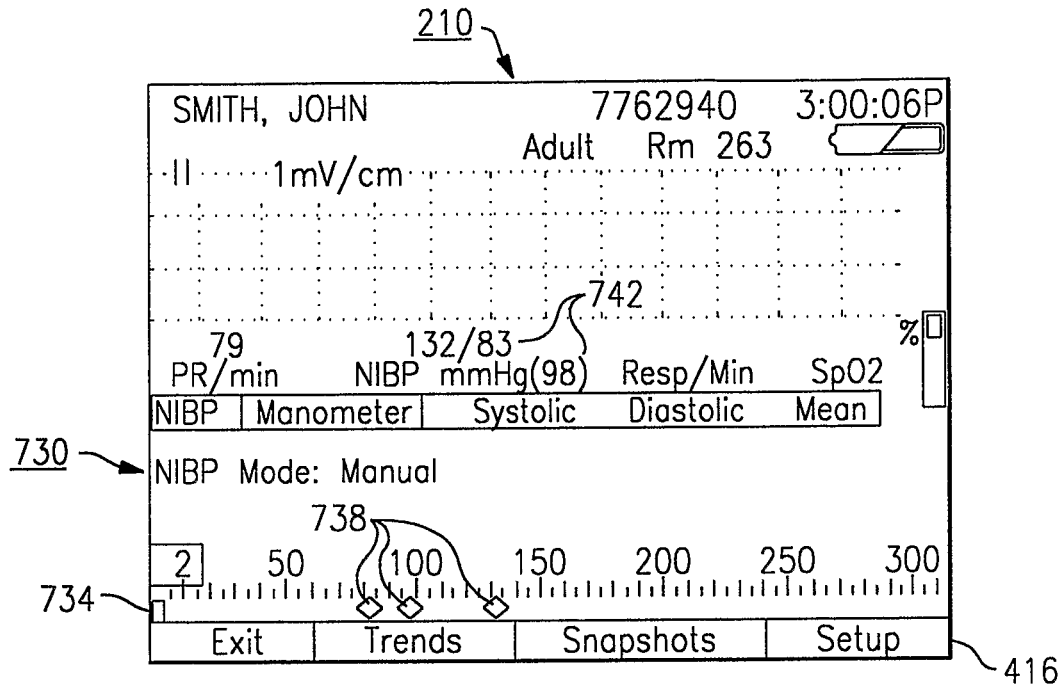
FIG. 46 is the display screen of FIGS. 44 and 45 at a later time following the NIBP measurement including depicting markers/indicators for the user with respect to systolic, diastolic and mean pressure values.

As noted generally above, the patient monitoring device 20 according to the present embodiment further includes a digital manometer that can be selectively displayed for the user during a blood pressure measurement procedure. This feature is enabled through the NIBP control menu 720 which is accessed in the manner previously described above from any of the primary vital signs display screens. In the NIBP control menu 720, FIG. 23, the Manometer option listed therein in the top panel 722 is highlighted using the directional arrow buttons 100. Pressing the SELECT button 96 causes a manometer menu 730 to appear as an overlay on the display screen 210, as shown in FIG. 44. Pressing the NIBP start/stop button 112 starts the NIBP measurement cycle as previously described. When the attached cuff 76, FIG. 1, is inflated, a manometer pressure indicator bar 734 located at the bottom of the display screen 210 dynamically displays the pressure reading, as shown in FIG. 45. When the blood pressure measurement cycle is completed, measurement numerics 742 appear below the waveform grid of the display screen 210 and each of the systolic, diastolic and MAP values for the measurement are displayed as markers 738, if valid readings are obtained for each along a defined manometer scale, as shown in FIG. 46.

Adjustment and enablement of the alarm limits and the remaining options on the control menu 720 are selected in the same manner described above. As to the context menu panel 416 options for parameter control menus and referring for example to FIG. 44, the Exit menu option, if selected by the SELECT button 96, reverts the user back to the previous primary vitals signs display screen, the Trends option changes the display screen to a trends viewer screen that causes a tabular or waveform history to be displayed, the Snapshots menu option causes a series of 21-second waveform snapshots of the current patient's vital signs to be selectively viewable, and the Setup menu option accesses the setup control menu.

Figure 22:
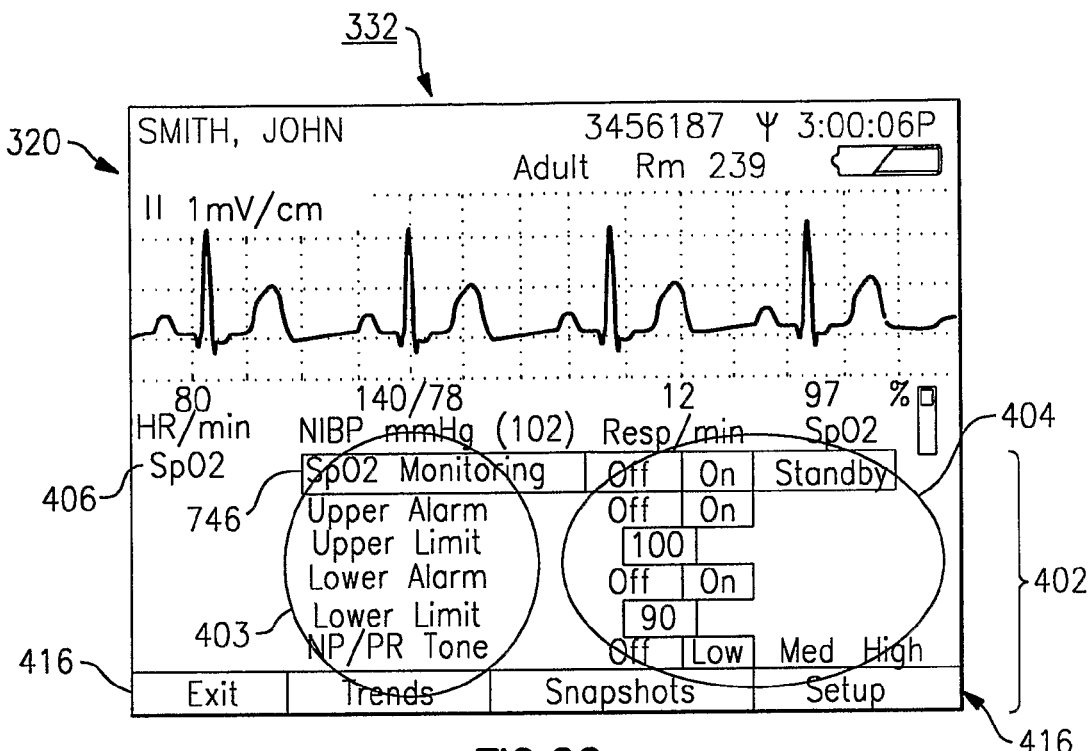
FIG. 22 is an exemplary control menu accessed through selection of the highlighted item of the display screen of FIG. 21.

The $SpO_2$ control menu 402, FIG. 22, permits setting of either continuous or a random (herein also commonly referred to as a spot-check) $SpO_2$ measurements, the setting of alarm limits and setting of the pulse tone. According to the present embodiment, continuous measurement of at least one physiologic parameter other than $SpO_2$, such as ECG, is enabled through the CPU 174 and the tethered physiologic parameter sensor assemblies, while permitting the user, by means of the user interface 92, to manually "spot check" $SpO_2$. That is to say, $SpO_2$ can be periodically or randomly checked on the patient (not shown) while simultaneously maintaining continuous monitoring of at least one other physiologic parameter.

When continuous $SpO_2$ is enabled, an alert is generated each time that $SpO_2$ readings are interrupted, such as when the sensor is disconnected from the patient after the monitoring device 20 has begun to take $SpO_2$ readings. Using the random monitoring or "spot check" feature, any number of randomly taken readings can be taken, attaching and detaching the sensor repeatedly without generating any alarms.

Figure 39:
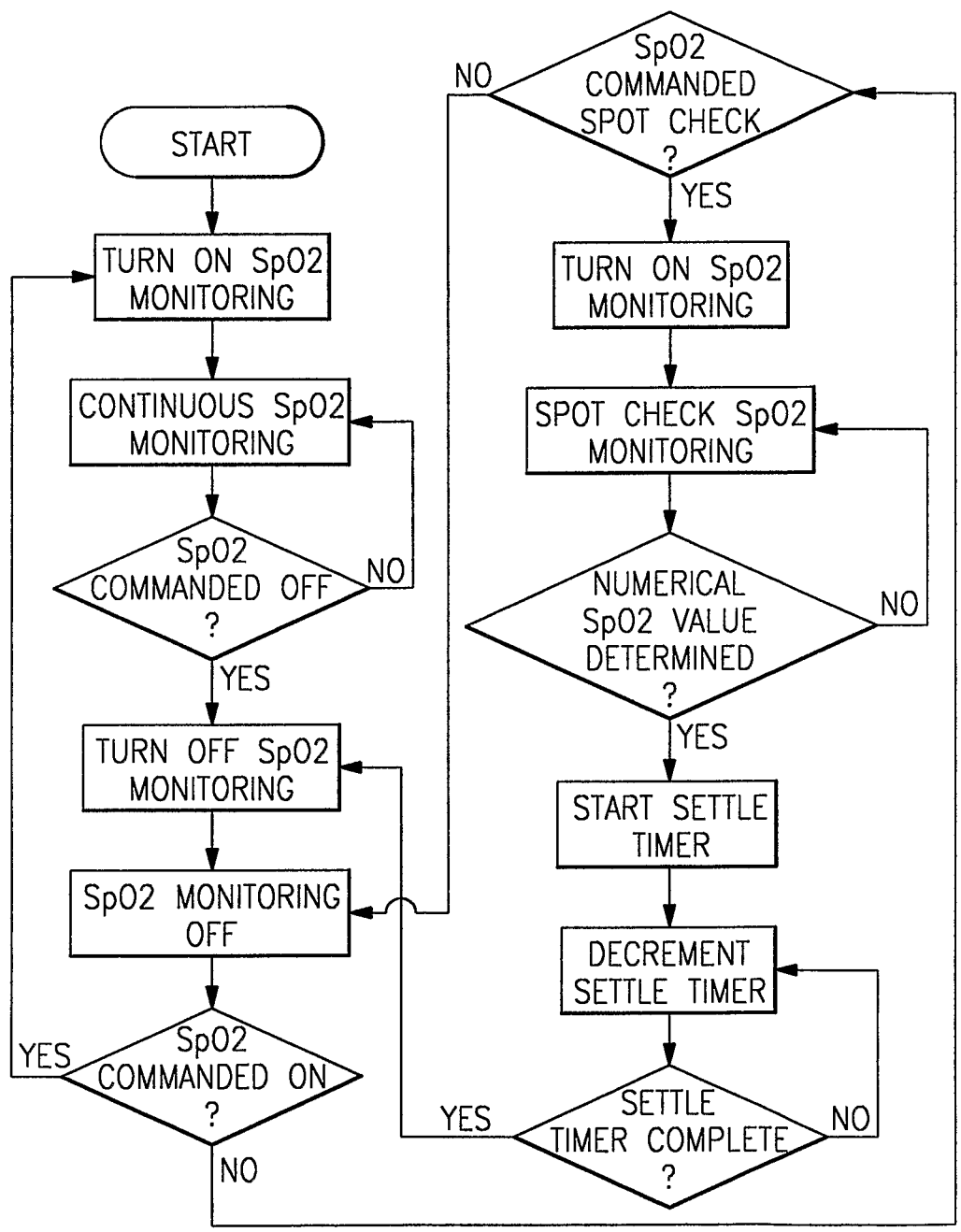
FIG. 39 is a flow chart relating to a $SpO_2$ spot checking feature of the vital signs monitoring device of FIGS. 1-3.

Referring to FIG. 39, a flowchart generally describes the herein referred to random or spot checking monitoring feature. Initially, the $SpO_2$ monitoring function of the monitoring device 20 is turned off. The user can turn the continuous $SpO_2$ monitoring function off manually with the user interface 92 by scrolling to the primary vital signs display screen, FIG. 21, and highlighting the $SpO_2$ text identifier 407 and pressing the SELECT button 96. The preceding accesses the $SpO_2$ control menu 402, FIG. 22. This control menu 402 is defined by two panels; a first panel 746 that includes a list of menu options and suboptions and a context menu panel 416 permitting navigation out of the spot-check mode. Highlighting the $SpO_2$ Monitoring menu option 403, using the left arrow button 100 to highlight the Off suboption and pressing the SELECT button 96 then turns off the continuous monitoring function and turns the spot checking feature.

When the $SpO_2$ monitoring function has been deactivated, it can then be reactivated by the user, either for continuous monitoring or for a one-time spot check reading. When a spot check is desired according to this embodiment, the pulse oximeter sensor 60, FIG. 1, is attached to the monitoring device 20 and to the patient. The user then highlights $SpO_2$ on the primary vitals sign display screen, FIG. 40, and presses the SELECT button 96. Upon pressing same, the user then highlights $SpO_2$ @ XX:XX and presses the SELECT button 96 accessing a $SpO_2$ drop-down menu 620, FIG. 41. This menu 620 that appears as an overlay onto the display screen (not shown in this view) includes On, Off and Spot Check options. The On option 622 permits the user to reenable the continuous SpO$_2$ monitoring feature. The Off option 624 disables the continuous monitoring feature and enables spot checks. The Spot check option 626 is highlighted in this instance, since the SpO$_2$ continuous monitoring function has already been disabled. The spot checking feature of the herein described monitoring device 20 is controlled through logic contained within the monitoring device 20 that allows the SpO$_2$ hardware to first initiate the sensor assembly 32, FIG. 1, and acquire a stable SpO$_2$ measurement from the patient as sensed by the apparatus. According to this embodiment and referring to FIG. 42, the primary vital signs display indicates SpO$_2$ Spot Check with a text identifier "SEARCH" 628 displayed above a Spot Check text identifier 629 to indicate that the monitoring device 20 is waiting for pulse oximetry data from the patient. After a few seconds, the SpO$_2$ indicator (if SpO$_2$ is used to determine pulse rate begins to display pulses and after approximately 30 seconds, the SEARCH text identifier 628 disappears and a pulse oximetry reading 256 appears, FIG. 43. Once a stable measurement has been acquired, the SpO$_2$ subsystem is powered down automatically. The stable SpO$_2$ reading that has been obtained is then displayed for a predetermined period of time or until a new spot check reading of SpO$_2$ is acquired. For additional spot checking, the preceding steps are then repeated wherein the SpO$_2$ sensor assembly 28 is initiated; a stable reading is acquired and then displayed for a predetermined period of time. In the meantime, any other parameters that are continuously monitored, such as ECG, are unaffected by the spot-checking functionality feature.

Each of the HR/PR and respiration control menus as well as the NIBP and pulse oximeter control menus permit the setting of upper and lower alarm limits. The HR/PR control menu (not shown) further permits adjustment of volume or enablement of the heart tone, and the preferred source (either SpO$_2$ or ECG) for heart rate wherein the current source is also highlighted. The respiration control menu (not shown) also permits the selection of the reference leadwire used from the ECG monitoring assembly.

In addition to the above parameter control menus and the time setup control menu, set-up control menus are also provided to the user in order to define the behavior of the herein described monitoring device 20. A typical set-up menu can be accessed according to this embodiment from any main display screen, such as those depicted in FIGS. 15-19, by performing the steps of: highlighting the battery indicator icon 220, HR/PR text identifier, SpO$_2$ text identifier, NIBP text identifier, respiration text identifier or the alarm icon 268; pressing the SELECT button 96 thereby accessing a parameter control menu; highlighting the setup option located in the context menu panel 416 at the bottom of the display screen 210; and pressing the SELECT button 96 again.

Figure 20:
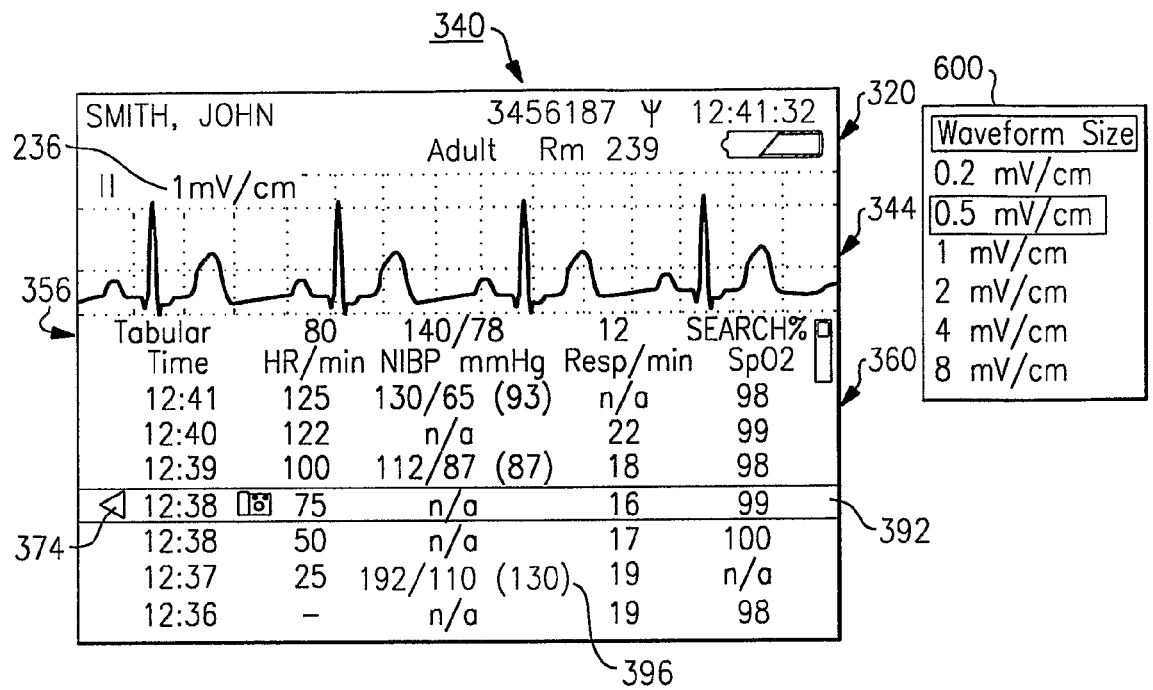
FIG. 20 illustrates another display screen showing how the display cursor is used to highlight a displayed item to permit navigation.
Figure 58:
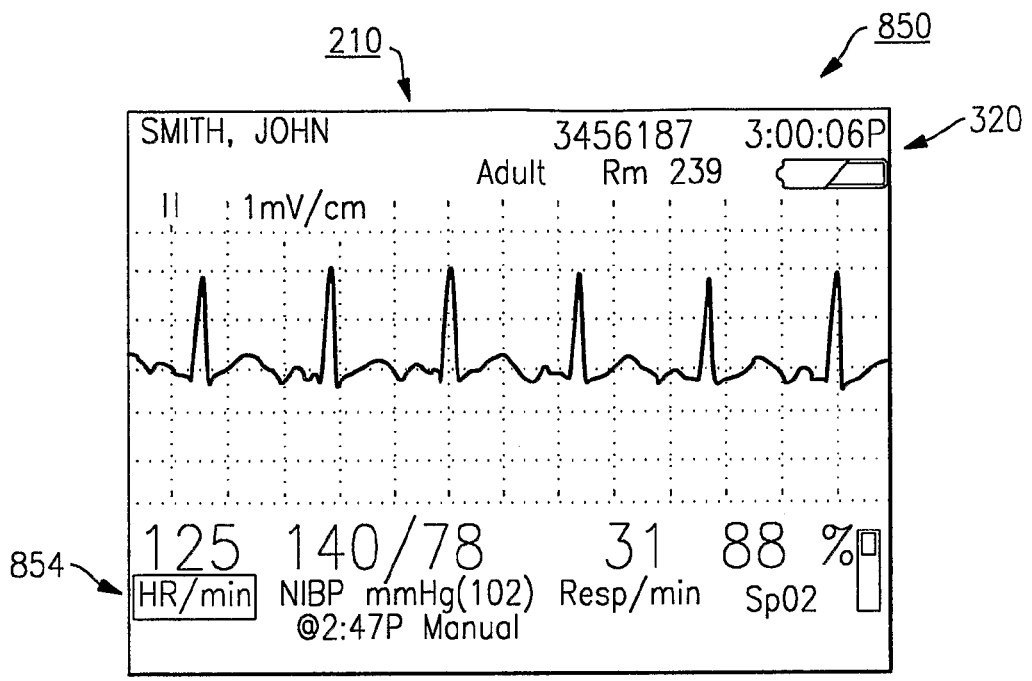
FIG. 58 depicts an exemplary alarm display screen of the vital signs monitoring device of FIGS. 1-3.

Among the items that can be configured in the respective set-up control menus according to this embodiment are the suspension and enablement of the audible alarms and adjustment of alarm tones, permitting management of same in a patient context. As previously noted, an "alarm" warns of a patient condition, such as a vital-sign reading that is outside of acceptable limits. When an "alarm condition" occurs according to the present embodiment, the red light status indicator 169, FIG. 2, on the front facing side 84 of the monitoring device 20 flashes and the numerics of the violating alarm limits shown on the display 88 turn red, such as depicted in FIG. 20. In addition, the display cursor moves automatically to the displayed item that caused the alarm and if not suspended, an audible alarm tone also may sound. A sample alarm condition 850 is shown in FIG. 58 in a single waveform display screen 210. In this instance, the heart rate for the monitored patient has exceeded a predetermined limit, as highlighted by 854. In addition to the above and in the instance that the monitoring device 20 is connected to a remote monitoring station 184, FIG. 6, notification of the alarm condition may also be transmitted to the remote monitoring station. Pressing the alarm silence/resume button 112 will silence current alarm tone for a predetermined period of time (e.g., 90 seconds).

An "alert" refers to an equipment or device condition, such as a low battery or a detached lead. When an "alert condition" occurs, the yellow light indicator 169 on the monitoring device 20 flashes and a message describing the condition appears on the display 88 in a message panel. An example of an equipment alert, in this instance, the disconnection of an ECG lead, is shown by the display screen of FIG. 59. Equipment alerts, according to this device embodiment, are indicated by a flashing yellow indicator 169 as well as a highlighted (e.g., yellow) alert message 306 provided conspicuously on the display screen of the monitoring device 20 and repeated sounding of an alert tone, in the instance that the alert is not acknowledged or the cause of the alert is not alleviated. The knowledgement is made through a context menu located at the alert window screen. Preferably, an alert tone will be distinguishable from an alarm tone to a user. In this specific instance, the depicted equipment alert is an ECG lead failure. Therefore and in addition, a diagram 302 is illustrated with an indication (in this instance a circled X) to indicate at least one disconnected lead. Alarm and alert conditions can also be detected by the remote monitoring station 184, FIG. 6, via the wireless network.

Examples of alert conditions detected by the herein described monitoring device 20 include, but are not limited to, the following: ECG Faults which can include Lead failure (single, multiple), excessive offset, or detection of unplugged ECG cable; NIBP Faults that can include an air leak, kinked hose, overpressure cuff condition, weak pulses to determine systolic/diastolic pressure, no pulses detected, detection of artifact prevents valid reading, or low battery; Network Communication Faults including the detection of a network communication problem, detection in attachment to charging cradle, low battery, or no SpO$_2$ detected; and respiration channel faults, such as a noisy signal or lead failure. Still referring to FIG. 59, acknowledgement of the alert by the user is made by highlighting the acknowledge option 864 at the bottom of the display screen and pressing the SELECT button 96, FIG. 2. Acknowledgement will remove the message panel and revert the display 88 to the previous display screen format.

Equipment faults for those situations in which the herein-described monitoring device 20 is operating on battery power as opposed to being mounted in the charging cradle have been discussed previously. In low battery conditions in which less than approximately 30 minutes of battery runtime remains, NIBP functions are disabled and the monitoring device 20 displays an appropriate message to the user that NIBP is disabled. Any attempt to press the NIBP start/stop button 112 or otherwise initiate a blood pressure measurement during a low battery condition will display an equipment alert with an appropriate message. However, placing the monitoring device 20 into the charging cradle 140 during a low battery condition will immediately enable all blood pressure monitoring features.

Figure 60:
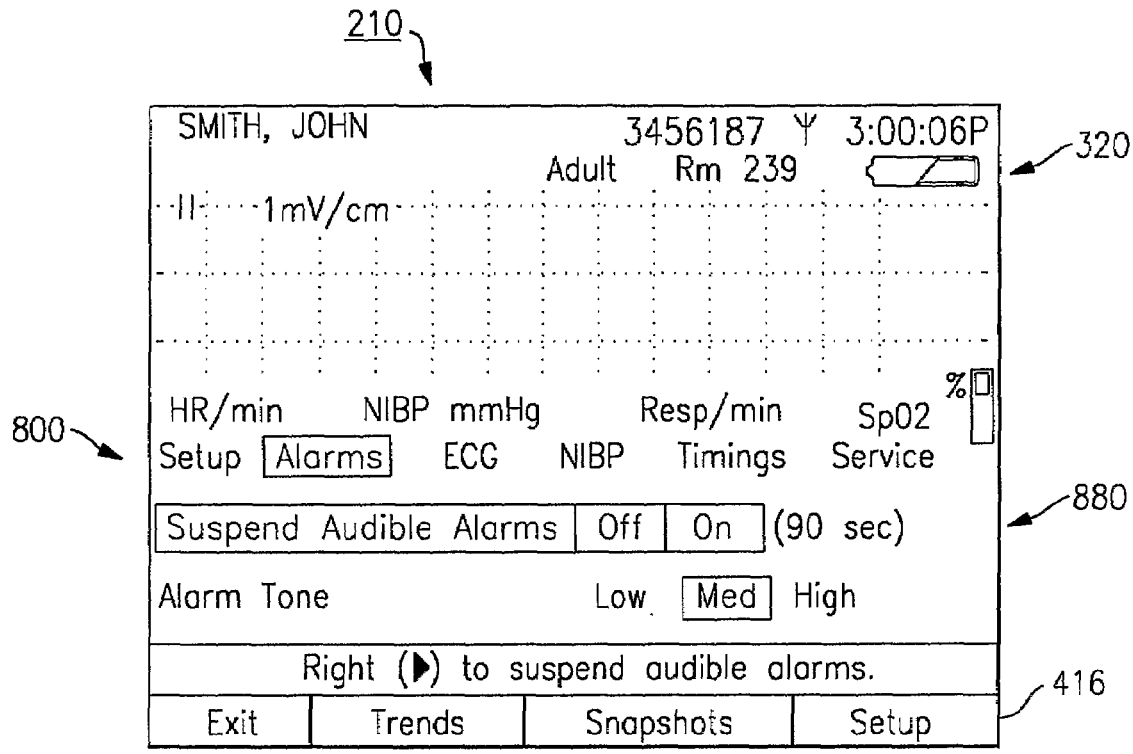
FIGS. 60 and 61 illustrate exemplary display screens for the vital signs monitoring device, including an alarms set-up menu in which audible alarms can be enabled or disabled.
Figure 61:
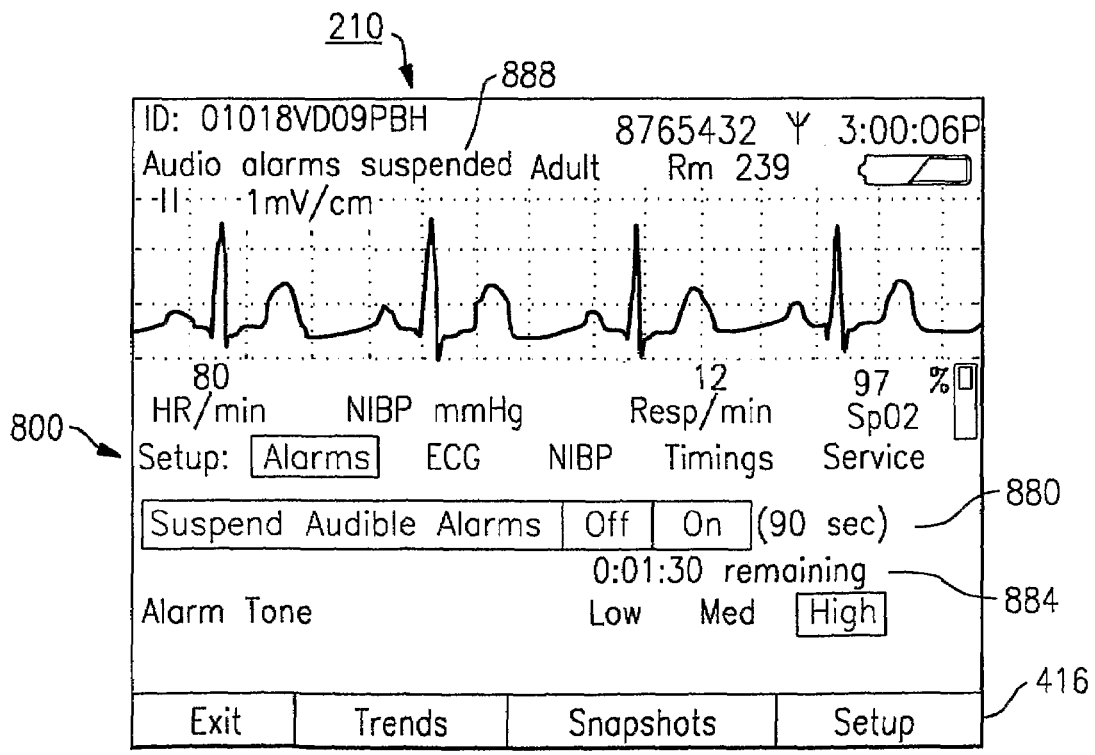

There are two techniques according to the present embodiment in order temporarily silence an alarm tone. The first technique is through pressing the alarm/silence button 108, which will silence any current alarm(s) for a predetermined period of time (e.g., 90 seconds). It should be noted, that silencing the audible tone does not affect the remaining alarm or alert indicators. The alarm tone can also, according to this particular device embodiment, be suspended for all parameters, thereby preventing the alarm tone from sounding if an alarm condition occurs while monitoring a patient. Suspension is done by the user through accessing an alarms suspend menu 880 that is provided in the set up controls menu 800, as shown in FIGS. 60, 61. If an alarm condition occurs while the alarm tones are suspended, the monitoring device 20 presents visual alarm indicators, but does not sound an audible tone.

As opposed to the interval for silencing an alarm tone, the suspension period of the alarm tone can be set during configuration of the monitoring device 20 to disable the tone for a predetermined period (i.e., 90 seconds-60 minutes). In addition, the monitoring device 20 can be so preconfigured such that the alarm tone cannot be suspended by the user, for example, through use of the configuration file that is uploaded to replace the factory settings of the monitoring device using the PC 192, FIG. 6, as previously described.

Referring to FIGS. 60, 61, and if the suspend feature is not disabled for the present monitoring device 20, the user can access the set-up control menu 800 by highlighting the text identifier of the parameter that is highlighted by the alarm. Once in the set-up control menu 800, the user can highlight the Alarms option, thereby accessing the Alarms set-up menu 880. As shown in FIG. 60 and upon accessing the Alarms setup menu 880, the display cursor highlights the Off menu option wherein a message panel appears in the display screen 210 to use the directional right arrow button 100 in order to highlight the On suboption. Once suspension has commenced, FIG. 61, a count-down timer 884 appears below the line in the set-up menu 880 as well as a highlighted indicator 888 in the upper portion of the display screen 210. When the suspension period expires, the alarm tone is again enabled. The alarms set up menu 880 further permits the volume of the alarm tone to be selectively adjusted by the user.

Typically, each medical facility defines the patient alarm limits for adult, pediatric and neonatal patients and then configures the monitoring device 20 with those alarm limits prior to putting the monitoring device into service. As previously noted herein, it was noted that the user can locally or custom adjust certain configuration settings of the herein described monitoring device 20.

Figure 62:
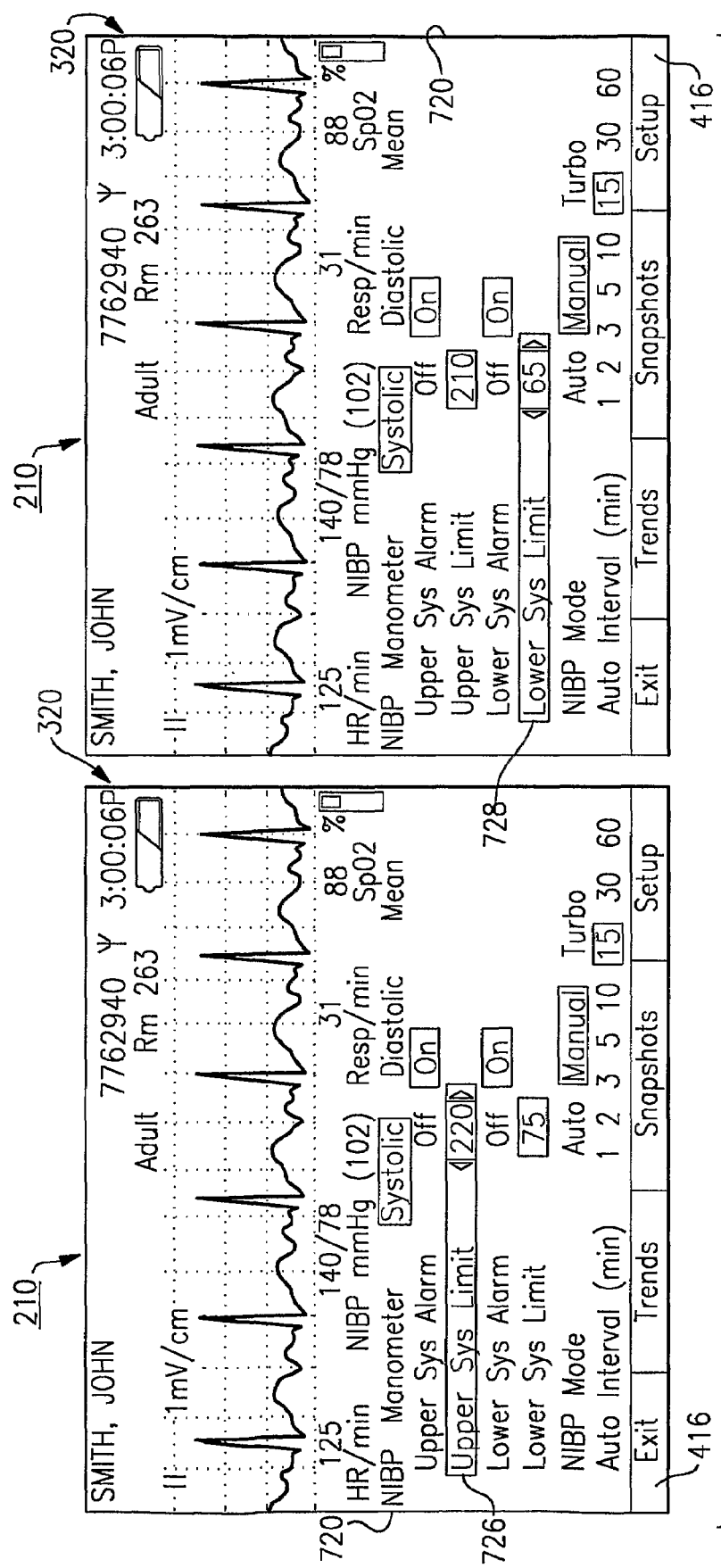
FIG. 62 illustrates examples of display screens in accordance with the present invention, including a parameter control menu wherein alarm limits can be temporarily customized for an individual patient.

According to another feature of the herein described patient monitoring device 20 and referring to FIG. 62, upper and lower alarm limits can be temporarily customized for an individual patient while the monitoring device 20 is in use. This temporary customization feature can be implemented by the user by highlighting any vital sign of interest from a primary vitals signs display screen and pressing the SELECT button 96 so as to access the control menu for that parameter; in this instance, NIBP, 720. Upper and lower alarm limits can then be selected by highlighting the current value and using the left and right directional arrow buttons 100 to set the new alarm limit(s), 726, 728. These new limit values are then stored in volatile memory of the CPU 174, FIG. 6, of the monitoring device 20 and are erased when the monitoring device is powered down unless the user specifically maintains them as part of the current patient. Alternatively, however, the device could be configured to allow a user such that the settings could be retained by the user irrespective of the patient. The monitoring device 20 is further configured to permit alarm limits to be customized for a particular patient from the remote monitoring station 184, FIG. 6, over the bidirectional wireless network using the radio card 180 and antenna 182 to receive new limit values.

In addition to the above features, the herein described monitoring device can be further configured such that the user can perform alarm management on the monitoring device 20 by permitting the user to actuate a feature provided on the user interface 92 that creates a predetermined percentage change to the alarm limits for a single parameter each time the SELECT button 96 is depressed at the time of an existing alarm. The initialization and initial percentage settings for each of the alarm parameter settings is performed according to this specific embodiment as part of the configuration of the monitoring device 20 prior to use of the monitoring device 20 through the PC 192 using the configuration file to override factory configuration settings, the new settings being stored by the CPU 174. A portion of a sample worksheet 198 is shown in FIGS. 64, 65 in which factory settings 199, shown in bold, can be adjusted for specific parameters, as listed in FIG. 64. Completing the worksheet 198 through the utility thereby provides means for completing the configuration file and assigning preset percentage amounts for adjusting alarm limits for any single parameter during a current alarm(s). The worksheet includes a menu choice 197 for enabling the alarm limit percentage option herein, also referred to as ParamSet. In essence, the user of this selective alarm management setting feature permits both upper and lower alarm limits to be preset accordingly and then used selectively by the clinician/nurse.

In summary, four (4) techniques are now provided in the present monitoring device 20 for handling or managing an existing alarm: First, the user can temporarily silence an alarm through use of the alarm silence/resume button 108 provided on the user interface 92. Turning the alarm off temporarily, however, in and of itself, does not change the limit. Therefore, if the patient's physiologic parameters are unchanged, the alarm will go off again momentarily depending on the default settings of the monitoring device 20 (e.g., 90 seconds). Second, the user can suspend the alarm tone for a patient for a predetermined period of time in the manner described above using the control menus 800. This feature also does not change any alarm limits. Third, the user can temporarily change or customize any of the alarm limits individually through features provided on the user interface 92, using the set-up control menus, as described above, such as 720 or other menu. As noted, this third technique can be accomplished by accessing the control menu for a specific parameter to highlight a specified parameter indicator (such as HR/min or NIBP, for example) and pressing the SELECT button 96. The corresponding parameter control menu, FIG. 62, is then displayed, permitting the user using the directional left and right cursor control buttons 100 to set appropriate alarm limits for the patient, the user then highlighting Exit to leave the menu window. Using the same pop-up menu or a similar menu, a fourth technique is provided by means of the presently described vital signs monitoring device 20 in which the user can also now automatically and selectively change a parameter alarm limit by a prescribed amount. Rather than incrementally changing the alarm limits, the user can change the alarm limits by a prescribed percentage amount each time the SELECT button 96 for this option is actuated as entered using worksheet 198, FIG. 64, via the configuration file. The latter feature can be accessed only during a current alarm(s). For example, upper and lower alarm limits for HR/PR can initially be set to alarm at an upper rate of 90 and a lower rate of 60. Using the latter feature, each time the SELECT button 96 is actuated for the above feature in the control menu, the alarm limits can be incremented by a predetermined percentage (e.g., 5 percent, 10 percent, or other). For example, if a five percent change were configured for the herein described monitoring device 20, the alarm limits would change to 94 (upper)/57 (lower) the first time the SELECT button 96 is depressed, 99 (upper)/54 (lower) the second time the button is depressed, and so forth. Similarly, NIBP (systolic pressure, diastolic pressure and mean pressure), SpO$_2$ and respiration rate limits can be similarly adjusted wherein the amount from factory (default) preset value alarm limit values can be adjusted, depending on the patient mode, for individual parameters as part of the pre-configuration routine using the PC 192. A tabular listing 950 is shown in FIG. 65 for appropriate percentage changes to the alarm limits according to one example.

The ECG monitoring sensor assembly 28, FIG. 1, of the present embodiment includes a respiration circuit provided in the form of an ASIC, wherein breath signals using impedance pneumography supports measurement of respiration rate as well as central apnea. The herein described monitoring device 20 can monitor heart signs (ECG) and respiration rate using either a 3-lead or a 5-lead ECG cable. Using a 3-lead ECG cable, one signal waveform for lead I, II, or III can be displayed. Using a 5-lead ECG cable, either one or two signal waveforms can be displayed by the monitoring device 20 for leads I, II, III, V, and if enabled in the configuration, aVR, aVL, or aVF. The SpO$_2$ or Resp waveform can also be displayed in place of the ECG waveform.

To monitor ECG, the appropriate ECG cable is plugged into the device housing 24 and appropriate electrode sites are selected on the body of the patient. This selection process is commonly known and does not form a significant part of the present invention. At least three (3) electrode connections are required for ECG/Resp monitoring. The monitoring device 20 provides a graphic display 302, FIG. 59, of a three or five lead ECG attachment with fixed locations being indicated. The locations of the circles shown in the diagram 302 in FIG. 59 do not indicate the exact placement of the electrodes on the patient.

Figure 59:
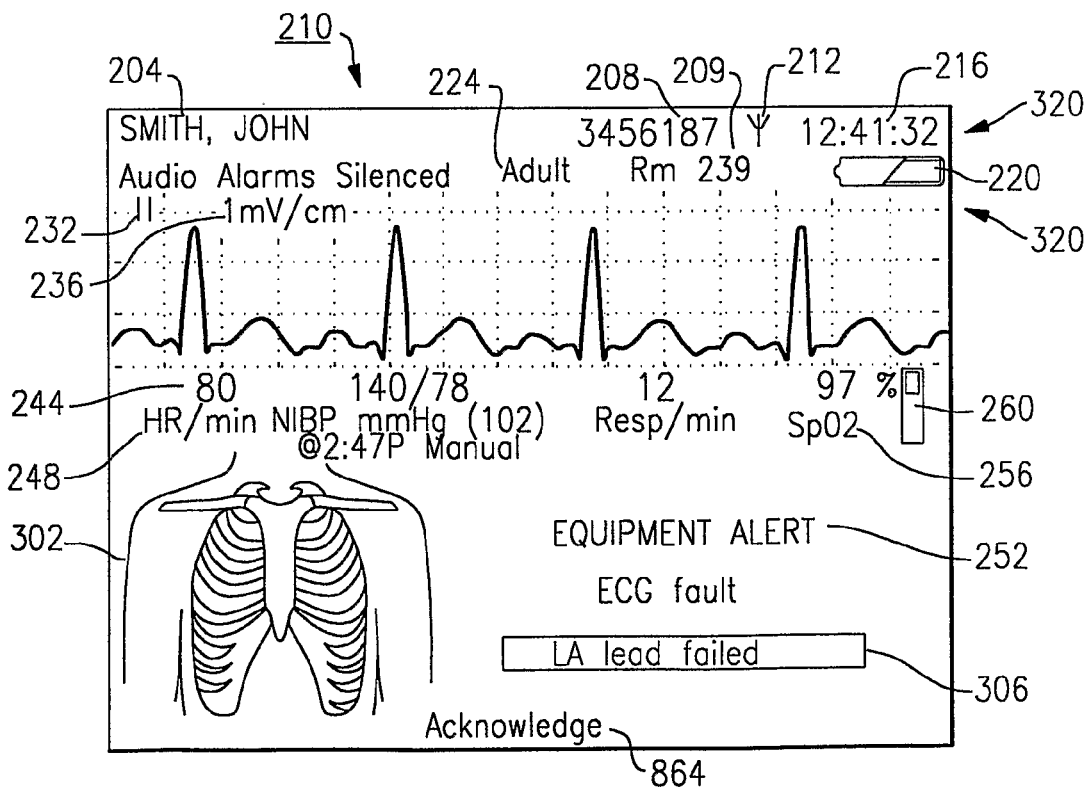
FIG. 59 depicts an exemplary equipment alert display screen of the vital signs monitoring device of FIGS. 1-3.

The monitoring device 20 is adapted to indicate whether some lead wires are not connected and to indicate an "ECG Fault" equipment alert and a chest diagram such as shown in FIG. 59, indicating the general location of the disconnected lead or leads. If the disconnected lead(s) indicate that the waveform source (Lead) used for HR determination, then the monitoring device 20 automatically reassigns, if possible, the Lead used for heart rate (HR). If the reassignment succeeds, the monitoring device 20 then displays another equipment alert with the message "ECG Lead changed".

When all leads are properly connected, returning to the primary vital signs display screen will confirm that an ECG waveform is being displayed as well as heart rate and other patient data. The waveform source can be changed, for example, from Lead I to Lead II by highlighting the waveform source selection icon using the cursor control buttons 100 and pressing the SELECT button 96. The latter will access the waveform source menu 580, FIG. 32, wherein the appropriate option 584 can be highlighted. In passing and by scrolling to the bottom of the waveform source choice menu, a second waveform can be added (or deleted). The waveform size can also be suitably varied by the user by highlighting the current waveform scale and pressing the SELECT button 96. The waveform size pop-up menu 600, FIG. 34, is accessed through the latter selection and a desired scaling factor can be highlighted.

Respiration rate is also monitored using the ECG monitoring circuit, as noted above, based on impedance pneumography, wherein respirations can be sensed from the ECG electrodes. The respiration numeric is displayed in the lower right corner of the display screen. To view the respiration waveform, the waveform source identifier 232, FIG. 15, is highlighted and the SELECT button 96 is pressed in order to access the waveform source pop-up menu 580, FIG. 33. Respiration as a menu option 588 is then highlighted and selected. Waveform size can be adjusted in the same manner described previously for the ECG waveforms.

Figure 35:
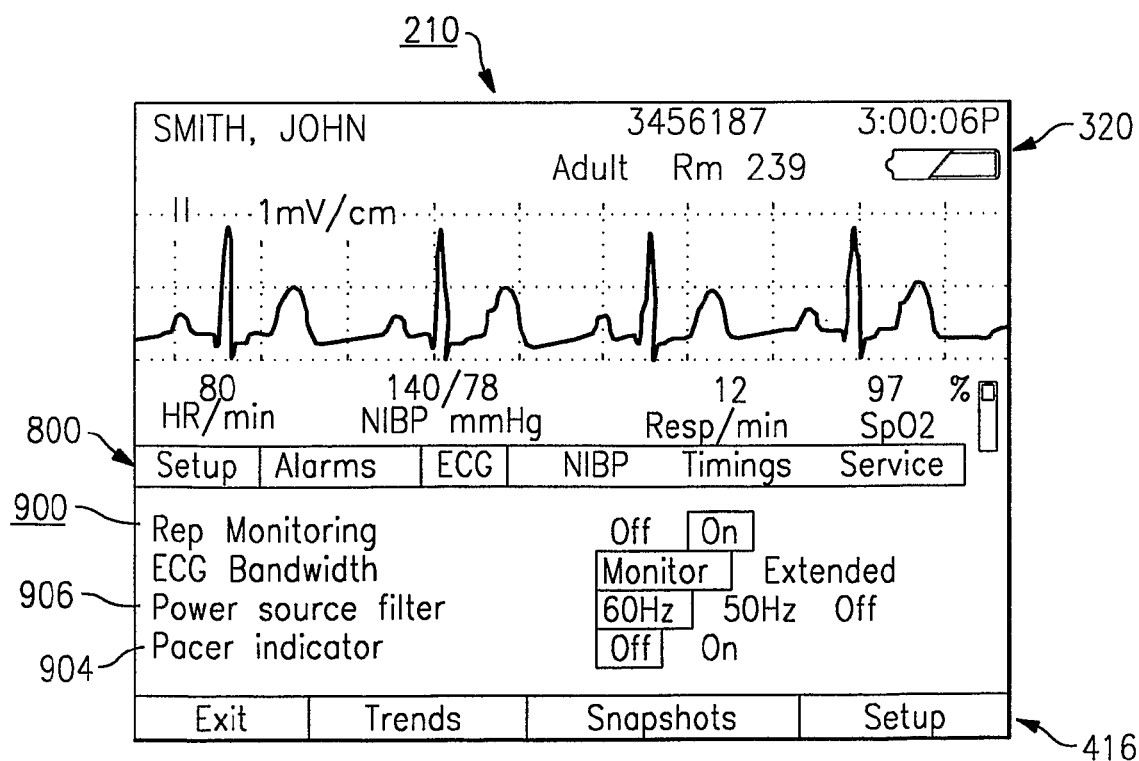
FIG. 35 is a display screen of the vital signs monitoring device depicting an ECG set-up menu in accordance with an aspect of the present invention.

In addition to monitoring the presence of the ECG waveform, the monitoring device 20 also detects the periodic signals emanating from an implanted pacemaker device. To that end, according to the present embodiment and referring to FIG. 35, if the patient being monitored has an implanted pacemaker device, the monitoring device 20 can indicate the occurrence of pacemaker or pacer signals by activation of the Pacer Indicator option 904 from the ECG set-up control menu 900, FIG. 36, if not already configured. When activated, the Pacer Indicator displays and prints vertical dashed lines to indicate pacemaker signals. If the Pacer Indicator option 904 is not enabled, the monitoring device 20 according to this embodiment continues to detect the pacemaker signals, but does not display or print the pacer markers. If the pacer signal is sufficiently strong, the monitoring device 20 displays this signal as a waveform spike, whether the Pacer Indicator option 904 is enabled or not. The present ECG circuit also detects when pacer signals/EMI pulses are occurring too frequently (outside of the periodicity of realistic pacer signals).

As previously noted, the detection of these pacer signals is commonly affected by electronic noise (such as EMI—Electromagnetic Interference) triggered, for example, from overhead lights that can hinder the ability to adequately detect a pacer signal from an implanted patient device (i.e., a pacemaker). Electrical noise from a power source can also cause an unclear or noisy waveform. According to one aspect, the invention provides the ability to select amongst the various ECG vectors, each of which has been processed for pacer pulse detection of both polarities and feeds both the pacer pulse detector and a peak/noise floor detector. An example is shown in FIG. 63. The latter detector generally captures a value 908 that is representative of the peak amplitude of real pacer pulses, and also captures a second value 912 that is representative of the peak amplitude of rapidly repetitive noise spikes, as shown in FIG. 63. Means allow selection of available ECG vectors and after obtaining a peak and noise floor level signal from each, shown as 915, 916, respectively, then picking an optimum ECG vector to continue feeding the pacer pulse detector. If the noise floor signal is made available to the user, the user can observe how the magnitude of the noise floor signal changes while moving the monitoring device 20 about in the vicinity of a possible noise source, the latter being shown magnified as 918. The reported signal level will generally increase as the monitoring device 20 is moved closer to the noise source and hence serves a directional aid in locating the source of electrical noise. Since it is already known at what level the noise spikes 912 would begin to trigger the pacer pulse detector, it may thus be determined whether a noise source was sufficiently large to cause false pulse detections. The principles described herein can be implemented by hardware, software or a combination of hardware and software.

The above circuit can further be used to validate a measurement in order to assess lead wire and electrode integrity for an ECG monitoring assembly. This measurement capability provides means for monitoring electrode performance as well as providing a means for proactively changing electrodes, as needed. As a matter of background and when lead wires of an ECG monitoring assembly are attached to a patient, the hardware drives a small current through each connected lead wire. This current is directed through the patient to a reference lead wire, also extending from the patient. As a result, each lead wire produces an offset voltage (with respect to the reference lead) based on Ohm's Law.

According to a variant of the present invention, each lead wire's offset voltage delta (that is, the voltage difference between each of its lead wires) can be determined, thereby providing a means for qualitatively "ranking" each of the lead wires and electrode assemblies. Software included within the monitoring device can then be utilized in order to provide an assessment of the electrodes and the lead wires based on the computed deltas, at least to determine the "qualitative state" of the electrodes, (e.g., if one lead wire has a much higher offset than the remaining leads, the most likely cause is an electrode contact issue such as a dry electrode or loss of contact with the patient). By comparing ratios of these voltage differentials, it is therefore possible to anticipate or become proactive relative to the life of portions of the ECG monitoring assembly.

In addition to the above, the monitoring device 20 also includes a power source filter that can be enabled from the ECG set-up control menu 900, FIG. 36. The settings for the power source filter should be applied depending on the power source in the facility. To that end, the power source filter option 906 according to this embodiment includes settings of 60 Hz and 50 Hz.

Many factors can adversely affect a blood pressure (NIBP) measurement including cardiac arrhythmias, sudden changes in blood pressure, patient motion such as convulsions or shivering, sudden cuff movement, vibration, vehicle motion, or a weak pulse, among others. According to the present embodiment, and when NIBP and ECG are each being monitored with regard to a patient, the herein described monitoring device 20 can be further equipped with the selective use of a motion artifact filter, such as the Smartcuf artifact filter manufactured by Welch Allyn, Inc., in order to increase the measurement accuracy in the presence of moderate motion artifacts or diminished pulses. Specific details relating to the specific motion artifact filter utilized by this device are described in U.S. Pat. No. 6,405,076 B1, the entire contents of which have been previously incorporated by reference.

Enablement of an artifact filter feature would include the steps of mounting each of the ECG and NIBP assemblies to the monitoring device 20 and to the patient respectively and as previously described, and then simultaneously monitoring the patient using each of the above physiologic sensor assemblies. The set-up control menu 800 would be accessed in the manner described above from a primary vital signs display screen. Upon accessing the set-up control menu 800, the NIBP menu option would be highlighted to access the NIBP setup control menu and then a Smartcuf suboption (not shown) would be highlighted and selected. Under some conditions in which the artifact filter feature is enabled and motion artifacts are too severe that measurement accuracy is still affected, the blood pressure measurement could be marked with an identifiable symbol on the display screen and on printouts. During certain types of arrhythmias and other situations in which a valid ECG signal cannot be obtained, the motion artifact filter could also be selectively disabled by accessing the control menu in the same manner described above, highlighting the NIBP option and disabling the Smartcuf sub-option.

The buttons of the user interface 96 and the display and/or backlight of the herein described monitoring device 20 can be locked out to prevent unauthorized access or use. This lock out feature can be accomplished in several different ways. According to one technique and if the feature is initially enabled using the PC configuration utility, the user can simultaneously hold down the left arrow, the right arrow and the up button simultaneously for a continuous period of time (e.g., 5 seconds). All buttons, including the Power ON/Off button 56 are locked. The buttons are automatically unlocked when an alert or an alarm condition occurs. Similarly, the display 88 and/or backlight can also be locked out by the user using a selective combination of buttons if no operator activity (e.g., no buttons are pressed) has occurred for a predetermined amount of time. The backlight lockout and the display lockout features would again be disabled immediately after an alarm or alert condition occurs.

The remaining set up control menus that are available to the user according to this specific embodiment include that relating to the Demo Mode (Disabled, Low, High). In addition to the set-up control menus, the monitoring device 20 incorporates additional control menus according to this embodiment including a Device Status Control Menu; and a Message Control Menu. The Device Status Control Menu permits the user to see a displayed information screen 420(*a*), 420(*b*), such as shown in FIG. 26. The information screen 420(*a*), 420(*b*) includes separate panels 422, 424 including the facility name, department name, and other associated information. The Message Control Menu is used, for example, with regard to changing of ECG leads in the event of a lead failure, requiring the reassignment of channels. At the bottom of each of the control menus are context menu panels 416, allowing the user to navigate, the context menus for the set-up control menus being identical to those of the parameter control menus.

A more specific example of using a control menu is now herein described with reference to the display screen depicted in FIG. 22. In this example, it is desired to alter (i.e., raise) the SpO$_2$ lower alarm limit to 95 and to shut off the HR/PR tone. To perform the first step and with "SpO$_2$" highlighted, the down arrow button 100 is used to scroll to highlight Lower Limit and the right arrow button 100 is then pressed as many times as necessary in order to increment the limit to the intended limit value; in this instance 95. It should be pointed out the herein described monitoring device 20 is programmed such that the upper alarm limit cannot be decreased to a level that is lower than the lower alarm limit for the parameter. Similarly, a lower alarm limit cannot be raised to a level that is greater than or equal to the upper alarm limit.

To adjust the HR/PR tone, the down arrow button 100 is pressed to scroll down to the HR/PR Tone field and the left or right arrow button is pressed as many times as is necessary in order to highlight OFF. Pressing the SELECT button or the display button 104 will exit the control menu screen and return the display to the previous vital signs display screen.

When the control menu is exited, the values that are displayed at the time the menu is exited are the new default values for the monitoring device 20. If a parameter is changed therefore, a decision must be made by the user prior to leaving the display screen whether or not to keep the previous setting values. If so, these parameters must be returned prior to exiting the control menu.

In summary and for purposes of menu and display navigation of the herein described monitoring device 20, the directional arrow buttons 100 are therefore used to perform any of the following functions: highlight an item on display, selection of options from a control menu, set-up menu or displayed "pop-up" menu, and changing the values of numeric parameters.

According to this embodiment, the display button 104 in addition to cycling though the configured display formats as shown in FIG. 19 can also be used to return to a primary vital signs display screen from a control menu and for closing a "pop-up" menu.

Finally, the SELECT button 96 is used to perform the following operations: display the control menu for a primary highlighted item, return from a control menu to a primary vital signs display screen, provide access to a set up menu when setup is highlighted by the display cursor, display of tabular and graphical trends when trends is highlighted, display of snapshots when snapshot is highlighted, turn on the display or the back light if either has been turned off by a power save feature of the monitoring device 20, and displaying a pop-up menu.

The herein described monitoring device 20 in addition to displaying current numerics and waveforms and the most recent measurements also stores a predetermined amount of patient data. According to this specific embodiment, up to 24 hours (at one-minute intervals) of trends (graphical and/or numeric) information for the patient being monitored can be stored, as well as NIBP and $SpO_2$ "spot checks" and "snapshots", as taken selectively by the user in connection with the patient and accessible from the Trends option of the context menu of any control menu, as described below. When data storage is at capacity, the data from each new reading overwrites the data from the oldest data stored. The features relating to the taking of $SpO_2$ and NIBP spot checks have previously been discussed at length.

As previously noted, a snapshot request is made by pressing the snapshot button 116, FIG. 7, which is provided on the front facing side 84 of the device housing 24. Upon depression of the snapshots button 116, the CPU 174 is programmed to provide a graphical display 298 of a default waveform (ECG, respiration) for a selected lead for a predetermined time period along with additional information, such as shown in the exemplary display screen of FIG. 50. In the sample snapshot display screen depicted in FIG. 50 and according to this embodiment, for example, 21 seconds of stored ECG data (7 seconds after the snapshot button 116 is pressed and 14 seconds before the snapshot button is pressed) is presented along with a time and data stamp for each waveform, the waveform source detected, the waveform scale (size) used and the corresponding number of the snapshot. According to the present embodiment, up to twenty (20) snapshots can be stored by the monitoring device 20 wherein any new snapshots overwrite the oldest stored versions thereof. It should be readily apparent that the number of snapshots can be suitably varied.

Figure 51:
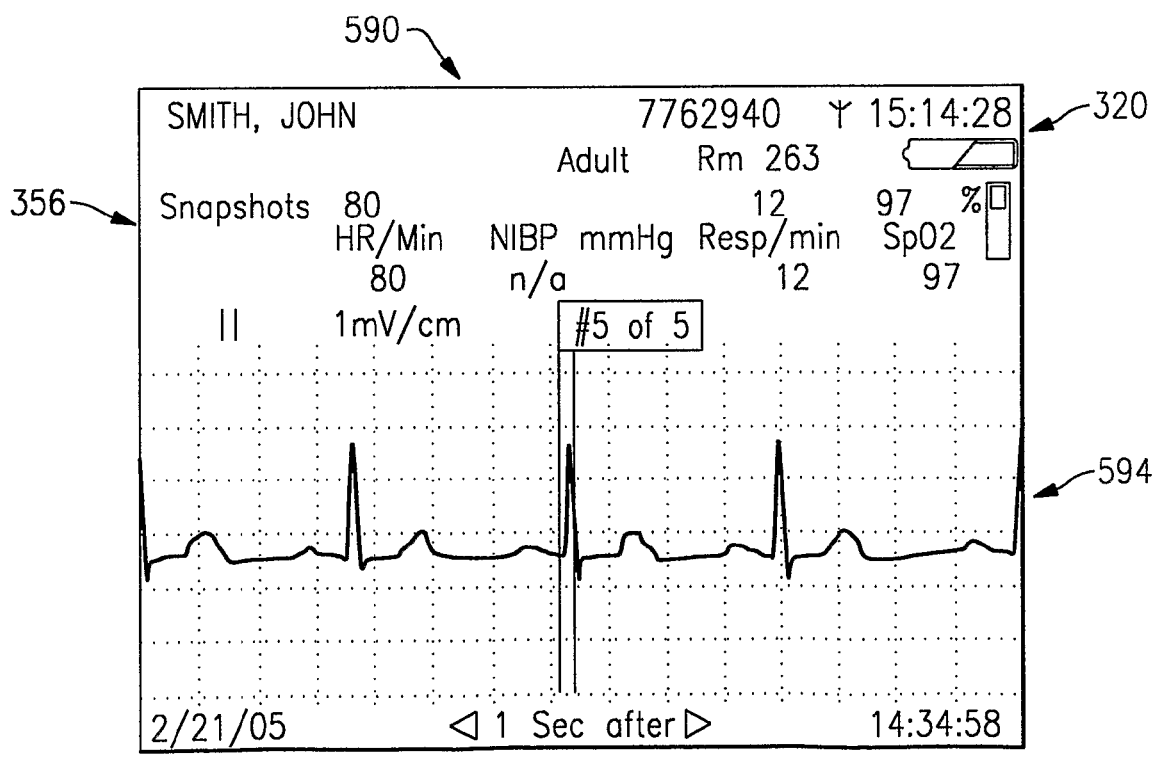

This data can be reviewed at the monitoring device 20. To review a snapshot and from any primary vital signs display screen, the user highlights any of the parameter text identifiers (HR/PR, $SpO_2$, etc) and then accesses a control menu for that parameter. The user then highlights the context menu panel 416 for that control menu and selects the snapshots option and confirms the selection by pressing the SELECT button 96. Highlighting the Snapshots option causes a Snapshots display screen to be displayed, examples of which is depicted in FIG. 51-53. Each of the up to twenty snapshots can then be viewed by the user. In the example shown in FIGS. 51-53, five (5) snapshots were taken. The snapshot display screen 590 includes a status panel 320 at the top of the display screen, a live numerics panel 356 and a snapshot display panel 594, respectively. The snapshot display panel 594 displays the stored snapshot for viewing and includes controls for selecting the snapshot file, the data source, the scale of the display and scroll controls. A vertical line indicates the center of the display. The waveform and numeric vitals signs data during the 21 seconds can be viewed by the user by highlighting time interval provided at the bottom of the display screen 590 and using the directional (left/right) cursor buttons 100 to scroll the display to the desired time. An example is shown in FIG. 52, for five seconds after the trigger point of the snapshot as opposed to FIG. 51, which is taken one second following the trigger point. The waveform source and size of the snapshot can also be selectively changed by the user for any captured snapshot by highlighting the appropriate icon on the display screen and accessing an associated drop-down menu 580, 600, as shown in FIG. 32, 33. In this example, the user can optionally switch to another type of display or can exit and return to a primary vital signs display screen by highlighting Snapshots in the upper left corner of the display screen and pressing the SELECT button 96. The preceding accesses a Trends menu 640, FIG. 53, wherein highlighting the appropriate option allows the user to navigate to another display screen.

As noted, the monitoring device 20 also stores trend data that is viewable in a plurality of user selectable formats. Trend data can be reviewed in a manner similar to that of waveform data by highlighting any parameter icon from any primary vitals signs display screen, FIG. 53, and pressing the SELECT button 96. Highlighting Trends from the resulting pop-up menu and pressing the SELECT button 96 accesses the Trends display screen 470, an example of which is shown in FIG. 54. The trends display screen 470 displays tabular trend data as well as live numerics for the monitored patient, the screen having a format consisting of a status panel 320, a trends live numerics panel 356 and trends panel 474, respectively. The status panel 320 is similar to that previously described with respect to FIG. 15 and the live numerics panel is similar to that depicted in FIG. 18. The trends panel 474 includes a tabular listing taken at one minute intervals with current vital sign readings for the monitored patient at the top of the display screen above the tabular list. As shown in this example, the reading time, HR/min, blood pressure (systolic/diastolic/mean), Respiration rate/min, and pulse oximeter ($SpO_2$) readings are provided. The user can scroll through the displayed tabular list using the directional (up/down) cursor buttons 100. The listing can include indications to show those readings that have already been captured in terms of snapshots, and any readings (if any) that are outside of permissible limits. Referring to FIG. 54, the user can selectively change the time interval for the displayed trend data by highlighting the Time text identifier 476 in the display screen 470 and accessing a view interval "pop-up" menu 660, permitting the user to selectively change the time (e.g., 5 minutes, 15 minutes, 30 minutes, 60 minutes) as needed by highlighting same and pressing the SELECT button 96.

FIG. 56 represents a sample display screen similar to FIG. 54, but indicating readings that have either exceeded alarm limits or appear suspect.

When attached to the charging cradle 140 and the PC 192, as shown in FIG. 6, all captured snapshots are caused to be automatically printed, if the monitoring device 20 is on for subsequent printing by the printer 195 through the USB data link with the PC 192 and the charging cradle 140. The data is uploaded to the PC 192, either manually or automatically through software loaded into the PC. According to the one version, all stored patient data is automatically printed when a powered monitoring device 20 is placed into a charging cradle 140. If the monitoring device 20 is off when placed in the charging cradle 140, then the autoprint feature is disabled. To enable the autoprint feature, the user must power up the monitoring device 20 and select Continue Patient in the start-up display screen 400(b), FIG. 24. Tabular trend data and snapshots stored within the monitoring device 20 are printed.

Figure 47:
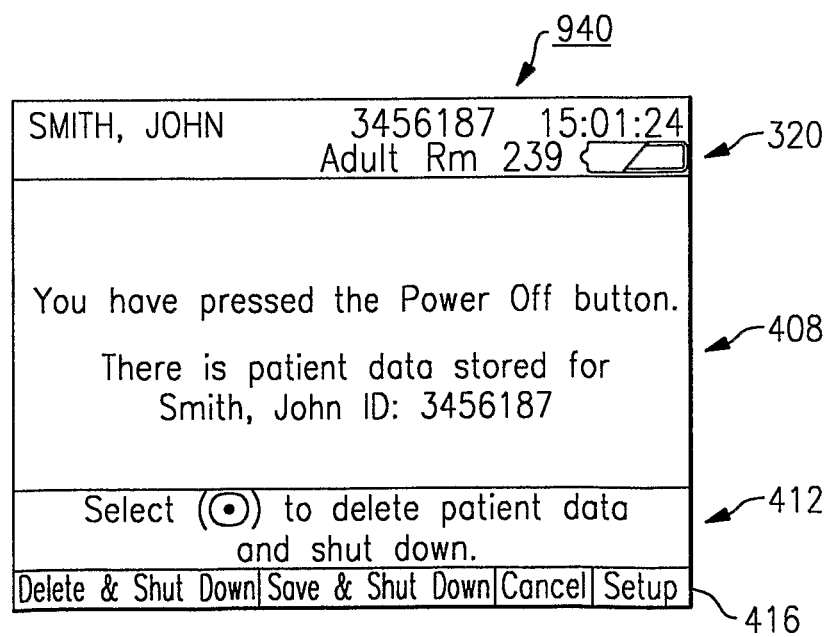
FIG. 47 is an exemplary Power Off display screen of the vital signs monitoring device.

Pressing the Power On/Off button 56 accesses a Power Off display screen as shown in FIG. 47. The format of the Power-Off display screen 940 includes a status panel 320, a notice panel 408, a short message panel 412 and a context menu panel 416, as read from the top of the display screen. If there is an intent to monitor the same patient when the monitoring device 20 is turned on again, then it may be desired to save the stored vitals signs data and monitoring device settings. As such, two options are provided in the context menu panel 416 at the bottom of the display screen 940—to either delete the stored data and settings and shut down or to save the stored data and shut down. Highlighting either of these options using the directional arrow buttons 100 and pressing the SELECT button 96 will cause the monitoring device 20 to shut down and either save or delete the stored data and settings. Alternatively, if the Power Off button 56 is pressed and the user wishes to continue monitoring the same patient, then a Cancel option is also provided in the Context menu panel 416 of the display screen 940. Failure to act within a predetermined time period according to this embodiment, as measured by an internal timer, will revert the display screen 940 to the previous screen or the default display screen as configured by the monitoring device 20.

Variations of the herein described monitoring device and associated hardware and software are possible within the intended scope of the inventive concepts in accordance with the following claims.

What is claimed is:

1. A multi-parametric patient monitoring device comprising:
a device housing that retains a portable power supply, a CPU, and a display for permitting the monitoring device to operate in a first stand-alone mode wherein a plurality of physiological sensors are attached to said device housing and in which parameter data received from said sensors is processed by said CPU within said device housing;
a wireless transceiver enabling said monitoring device to operate in a second mode in which patient-related data is transmitted to a remote station and in which said monitoring device is further configured to be separately operated in a separate charging mode wherein said device can still operate simultaneously in the second remote wireless transmitting mode while in said charging mode, said device further including a wired transceiver to permit patient-related data transfer remotely in said charging mode, and in which said device simultaneously transfers data over each of said wired and said wireless transceivers,
wherein a plurality of physiological parameters are continuously monitored by said monitoring device, said monitoring device further comprising a pulse oximeter assembly in which said monitoring device is programmed to continuously monitor at least one of said plurality of physiological parameters while said pulse oximeter assembly is enabled to selectively operate in each of a continuous monitoring mode and a spot-check monitoring mode and in which the at least one of said plurality of physiological parameters is continuously monitored independent of the monitoring mode selected for the pulse oximeter assembly.

2. A device according to claim 1, in which the monitoring device is placed in a charging cradle in the charging mode, the charging cradle including a data port to permit communication between said patient monitoring device and at least one peripheral device.

3. A device as recited in claim 1, wherein said monitoring device is patient wearable in said first and second modes.

4. A device as recited in claim 2, in which the peripheral device is a large display wherein patient-related data is further transmitted in real time to said display in said charging mode using said data port.

5. A device as recited in claim 2, in which the peripheral device is a computing device.

6. A device as recited in claim 5, in which the computing device sends a configuration file to the patient monitoring device providing default settings for said monitoring device.

7. A device as recited in claim 5, in which said computing device automatically receives stored data from said patient monitoring device when said monitoring device is attached to said charging cradle.

8. A device as recited in claim 2, wherein said CPU includes memory for storing and trending patient-related data, said device further including a user interface that permits snapshots of data to be selectively taken, wherein all trended data and snapshot data is automatically transmitted when said patient monitoring device is attached to said charging cradle.

9. A device as recited in claim 1, including a user interface defined on said housing having a plurality of user-actuable buttons for operating said device, and in which said buttons can selectively be locked out.

10. A device as recited in claim 1, including a display having a backlight, and in which said display and the backlight can be selectively powered off to prevent unauthorized access.

11. A device as recited in claim 10, wherein at least one of the display and the backlight can be powered down based on inactivity of said device.

12. A device as recited in claim 1, including an ECG assembly, said ECG assembly including a pacer detection circuit for determining pacer spikes.

13. A device as recited in claim 12, wherein said ECG assembly determines an appropriate ECG vector for electrical noise detection using pacer spikes from the pacer detection circuit.

14. A device as recited in claim 1, wherein the wireless transceiver can be selectively powered down if the transceiver is out of range of an access point.

15. A device as recited in claim 9, wherein said user interface includes a plurality of buttons that are used with a display screen to navigate using drop-down menus that are accessed through the user interface.

16. A device as recited in claim 15, wherein said user interface can access a disconnected wireless mode menu in which the device can be selectively switched between a disconnected wireless mode and said wireless mode.

17. A device as recited in claim 1, wherein enabling said monitoring device in said spot-check monitoring mode permits a sensor of said pulse oximeter assembly to be continually removed and attached from a patient without alarm generation.

18. A device as recited in claim 17, wherein enabling said monitoring device in said continuous monitoring mode generates an alert each time said sensor of said pulse oximeter assembly is removed from the patient.

* * * * *